(12) United States Patent
Distefano et al.

(10) Patent No.: US 7,897,765 B2
(45) Date of Patent: Mar. 1, 2011

(54) THERAPEUTIC COMPOUNDS AND USES THEREOF

(75) Inventors: Peter Distefano, Southboro, MA (US); Andrew Napper, Salem, MA (US); Rory Curtis, Ashland, MA (US); Jay Luly, Wellesley, MA (US); Manuel A. Navia, Lexington, MA (US); Russell J. Thomas, Siena (IT); Jean-Francois Pons, Abingdon (GB); Jeffrey O. Saunders, Acton, MA (US)

(73) Assignee: Elixir Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/367,585

(22) Filed: Feb. 9, 2009

(65) Prior Publication Data
US 2009/0264410 A1 Oct. 22, 2009

Related U.S. Application Data

(63) Continuation of application No. 10/982,997, filed on Nov. 4, 2004, now Pat. No. 7,504,506.

(60) Provisional application No. 60/517,058, filed on Nov. 4, 2003.

(51) Int. Cl.
*C07D 401/00* (2006.01)
(52) U.S. Cl. .................................................. 546/17
(58) Field of Classification Search ................ 546/17
See application file for complete search history.

(56) References Cited

U.S. PATENT DOCUMENTS

| | | | |
|---|---|---|---|
| 5,492,916 A | 2/1996 | Morriello et al. |
| 5,492,920 A | 2/1996 | Chen et al. |
| 5,494,919 A | 2/1996 | Morriello et al. |
| 5,536,716 A | 7/1996 | Chen et al. |
| 5,559,128 A | 9/1996 | Chakravarti et al. |
| 5,578,593 A | 11/1996 | Chen et al. |
| 5,622,973 A | 4/1997 | Morriello et al. |
| 5,652,235 A | 7/1997 | Chen et al. |
| 5,721,250 A | 2/1998 | Morriello et al. |
| 5,721,251 A | 2/1998 | Chen et al. |
| 5,723,616 A * | 3/1998 | Houghton et al. ............. 546/18 |
| 5,767,124 A | 6/1998 | Draper et al. |
| 5,783,582 A | 7/1998 | Guo et al. |
| 5,830,433 A | 11/1998 | Dean et al. |
| 5,877,182 A | 3/1999 | Nargund et al. |
| 5,880,125 A | 3/1999 | Nargund |
| 6,358,951 B1 | 3/2002 | Carpino |
| 6,420,376 B1 | 7/2002 | Tata et al. |

FOREIGN PATENT DOCUMENTS

WO    WO 2005/097788    10/2005

OTHER PUBLICATIONS

Elliot, J.M., et al., "Serine Derived NK1 Antagonist 1: The effects of Modification to the Serine Substituents," *Bioorganic & Medicinal Chem. Letters* vol. 8: 1845-1850 (1998).
Supplementary Partial European Search Report from corresponding EP application No. EPP290691 dated May 6, 2009.

* cited by examiner

*Primary Examiner*—Nizal S Chandrakumar
(74) *Attorney, Agent, or Firm*—Lando & Anastasi, LLP

(57) ABSTRACT

Compounds of formula (I) are described herein

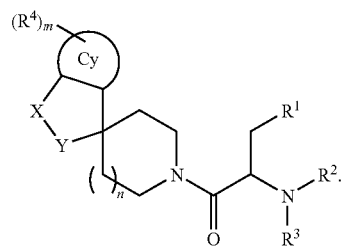

The compounds can be used, for example, to modulate growth hormone secretagogue receptor (GHS-R). In some instances, the compounds can be used to treat obesity.

35 Claims, 3 Drawing Sheets

THERAPEUTIC COMPOUNDS AND USES THEREOF

CROSS-REFERENCE TO RELATED APPLICATIONS

This application is a continuation application of U.S. patent application Ser. No. 10/982,997, filed Nov. 4, 2004 now U.S. Pat. No. 7,504,506, which claims priority under 35 USC §119(e) to U.S. Patent Application Ser. No. 60/517,058, filed on Nov. 4, 2003. The contents of the prior applications are hereby incorporated by reference in their entirety for all purposes.

BACKGROUND

The growth hormone secretagogue receptor (GHS-R) regulates a number of physiological processes, including growth hormone (GH) release, metabolism, and appetite. Ghrelin is a 28 amino acid peptide that is an endogenous ligand for the growth hormone secretagogue receptor (GHS-R) also known as the ghrelin receptor. Ghrelin has been shown to stimulate feeding in humans. In rodents, ghrelin induces body weight gain and adiposity. See, e.g., Asakawa (2003) Gut 52:947. In addition to regulating feeding, ghrelin can stimulate GH secretion by activating GHS-R, particularly in somatotrophic tissue.

Accordingly, compounds that modulate GHS-R activity are at least useful for controlling disorders associated with GHS-R physiology.

SUMMARY

The invention relates, inter alia, to useful compounds and compositions that modulate GHS-R, as well as methods of using and making the compounds. The compounds are spirocyclic compounds. The compounds can be used in therapeutic applications, including modulation of disorders, diseases or disease symptoms in a subject (e.g., mammal, human, dog, cat, horse). The compounds include useful GHS-R antagonists. Such antagonists can be used, e.g., to reduce feeding in a subject.

The compounds (including stereoisomers thereof) can be created either singly, in small clusters, or in a combinatorial fashion to give structurally diverse libraries of compounds.

In some embodiments, the invention features a compound of formula (I) or a pharmaceutically acceptable salt thereof:

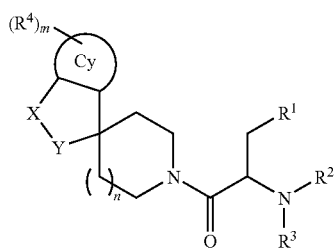

formula (I)

wherein, $R^1$ is H, $C_1$-$C_{10}$ alkyl, aryl, aryl($C_1$-$C_6$ alkyl), heteroaryl, heteroaryl($C_1$-$C_6$ alkyl), cycloalkyl, cycloalkyl($C_1$-$C_6$ alkyl), heterocyclyl, heterocyclyl($C_1$-$C_6$ alkyl), ($C_1$-$C_6$ alkyl)-K-($C_0$-$C_6$ alkyl), aryl($C_0$-$C_6$ alkyl)-K-($C_0$-$C_6$ alkyl), heteroaryl ($C_0$-$C_6$ alkyl)-K-($C_0$-$C_6$ alkyl), cycloalkyl($C_0$-$C_6$ alkyl)-K-($C_0$-$C_6$ alkyl), or heterocyclyl($C_0$-$C_6$ alkyl)-K-($C_0$-$C_6$ alkyl);

wherein $R^1$ can be taken together with one or both of $R^2$ and $R^3$ and the carbon to which it is attached to form a heterocyclyl or heteroaryl ring structure; wherein K is O, S, SO, $SO_2$, $N(R^5)C(O)$, $C(O)N(R^5)$, OC(O), C(O)O, $CR^5$=$CR^5$, or C≡C; wherein each alkyl can be independently substituted with at least one halo, $C_1$-$C_6$ alkyl, acetyl, $SO_2R^6$, $OR^6$, $CO_2R^6$; and wherein each aryl, heteroaryl, cycloalkyl or heterocyclyl can be independently substituted with aryl, aryloxy, $C_1$-$C_6$ alkyl, halo, $OR^6$, $SO_2R^6$, $CF_3$, $OCF_3$, $NO_2$, $N(R^5)_2$, $N(R^5)C(O)(R^5)$, $C(O)OR^6$, $OC(O)R^5$, $C(O)N(R^5)_2$, $SO_2N(R^5)_2$, or $N(R^5)SO_2(R^5)$;

$R^2$ is $SO_2R^8$; and wherein $R^2$ can be taken together with one or both of $R^1$ and $R^3$ and the nitrogen to which it is attached to form a heterocyclyl or heteroaryl ring structure;

$R^3$ is H, $C_1$-$C_6$ alkyl, acetyl, or aryl ($C_1$-$C_6$ alkyl), wherein aryl can be optionally substituted with $R^6$ or $OR^6$; and wherein $R^3$ can be taken together with one or both of $R^1$ and $R^2$ and the nitrogen to which it is attached to form a heterocyclyl or heteroaryl ring structure;

each $R^4$ is independently halo, $C_1$-$C_6$ alkyl, alkoxy, CN, $N(R^6)_2$, acetyl, $CF_3$ or $OCF_3$, $OCH_2CF_3$;

each $R^5$ is independently H, $C_1$-$C_6$ alkyl, acetyl, cycloalkyl, aryl, aryl ($C_1$-$C_6$ alkyl), heteroaryl, or heteroaryl ($C_1$-$C_6$ alkyl); each of which is substituted with one or more $R^4$;

each $R^6$ is independently H or $C_1$-$C_6$ alkyl;

each $R^8$ is independently cycloalkyl, cycloalkyl ($C_1$-$C_6$ alkyl), heterocyclyl, heterocyclyl ($C_1$-$C_6$ alkyl), aryl, aryl ($C_1$-$C_6$ alkyl), heteroaryl, heteroaryl ($C_1$-$C_6$ alkyl), $C_1$-$C_6$ alkyl, $C_2$-$C_6$ alkenyl, $C_2$-$C_6$ alkynyl; each of which is independently substituted with $R^9$, halo, $C_1$-$C_6$ alkyl, $OR^5$, CN, $NO_2$, $N(R^5)_2$, $C(O)R^5$, $C(O)OR^5$, $OC(O)R^5$, $N(R^5)C(O)R^5$, $N(R^5)C(O)OR^5$, $C(O)N(R^5)_2$, $SR^5$, $SO_2R^5$, $S(O)R^5$, or $SO_2N(R^5)_2$;

X is $CHC(O)OR^9$, $CHC(O)R^9$, $CHC(O)N(R^9)_2$, $NSO_2R^9$, $CHN(R^9)_2$, CO, $CHN(R^9)SO_2R^9$, $CHCH_2OR^9$, $CHR^9$, $NR^9$, $NC(O)R^9$, $NC(O)OR^9$, $NC(O)NR^3R^9$, or when taken together with Y is $CR^9$=$CR^9$;

Y is $(CH_2)_8$, $CHC_1$-$C_8$ alkyl, O, CO, or when taken together with X is $CR^9$=$CR^9$, wherein when Y is O, X is C;

each $R^9$ is independently H, $C_1$-$C_6$ alkyl, aryl ($C_1$-$C_6$) alkyl, cycloalkyl ($C_0$-$C_6$)alkyl, heterocyclyl ($C_0$-$C_6$)alkyl, aryl ($C_0$-$C_6$)alkyl, or heteroaryl ($C_0$-$C_6$)alkyl; each of which can be independently substituted with one or more $R^{10}$;

each $R^{10}$ is independently H, $C_1$-$C_6$ alkyl, aryl ($C_1$-$C_6$) alkyl, cycloalkyl ($C_0$-$C_6$)alkyl, heterocyclyl ($C_0$-$C_6$)alkyl, aryl ($C_0$-$C_6$)alkyl, or heteroaryl ($C_0$-$C_6$)alkyl, halo, $OR^5$, $NR^4SO_2R^5$, $N(R^5)_2$, CN, $C(O)OR^5$, $OC(O)R^5$, $COR^5$, $NO_2$, $SO_2N(R^5)_2$, $SO_2R^5$, $S(O)R^5$, $SR^5$, $CF_3$, $CH_2CF_3$ or $OCF_3$;

Cy is aryl or heteroaryl;

m is 0-6;

n is 0, 1, or 2; and p is 1, 2 or 3;

wherein $R^8$ is not di-chlorophenyl when $R^1$ is benzyloxy.

In some embodiments, $R^1$ is aryl, aryl($C_1$-$C_6$ alkyl), heteroaryl($C_1$-$C_6$ alkyl), heteroaryl, aryl($C_0$-$C_6$ alkyl)-K-($C_1$-$C_6$ alkyl), or heteroaryl($C_0$-$C_6$ alkyl)-K-($C_0$-$C_6$ alkyl); wherein K is O, N, or S; wherein each alkyl can be independently substituted with at least one halo, $C_1$-$C_6$ alkyl, acetyl, $SO_2R^6$, $OR^6$, $CO_2R^6$; and wherein each aryl, heteroaryl, cycloalkyl or heterocyclyl can be independently substituted with aryl, aryloxy, $C_1$-$C_6$ alkyl, halo, $OR^6$, $SO_2R^6$, $CF_3$, $OCF_3$, $NO_2$, $N(R^5)_2$, $N(R^5)C(O)(R^5)$, $C(O)OR^6$, $OC(O)R^5$, $C(O)N(R^5)_2$, $SO_2N(R^5)_2$, or $N(R^5)SO_2(R^5)$.

In some embodiments, $R^1$ is aryl($C_0$-$C_6$ alkyl)-K-($C_1$-$C_6$ alkyl).

In some embodiments, wherein $R^1$ is benzyloxy.

In some embodiments, wherein $R^1$ is aryl($C_1$-$C_6$ alkyl).

In some embodiments, $R^1$ is benzyl.

In some embodiments, $R^8$ is $C_1$-$C_6$ alkyl substituted with $R^9$ or $N(R^5)_2$.

In some embodiments, $R^9$ is heterocyclyl.

In some embodiments, $R^9$ is a nitrogen containing heterocyclyl.

In some embodiments, the nitrogen containing heterocyclyl is substituted with $C_1$-$C_4$ alkyl.

In some embodiments, $R^9$ is pyrrolidyl, piperidyl, piperizinyl, or morpholinyl.

In some embodiments, $R^8$ is substituted with $N(R^5)_2$, and each $R^5$ is independently H or $C_1$-$C_6$ alkyl.

In some embodiments, each $R^5$ is independently H, methyl, ethyl, isopropyl, or t-butyl.

In some embodiments, $N(R^5)_2$ is selected from the group consisting of

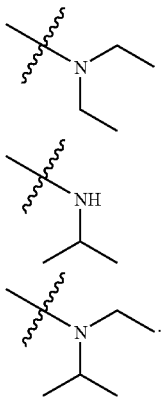 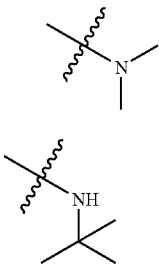 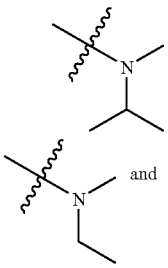

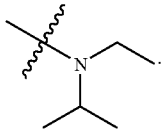 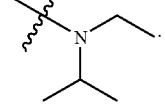  and

.

In some embodiments, the nitrogen containing heterocyclyl is a bridged heterocyclyl.

In some embodiments, $R_8$ is $C_2$ or $C_3$ alkyl substituted with $R^9$ or $N(R^5)_2$.

In some embodiments, $N(R^5)_2$ is selected from the group consisting of

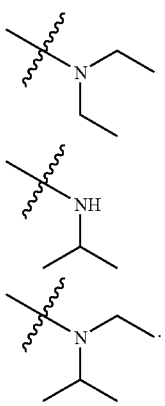 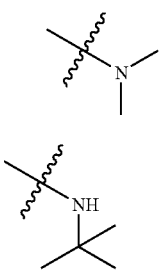 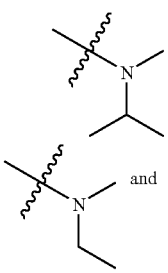

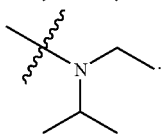 and similar groups

In some embodiments, X and Y taken together are $CR^9$=$CR^9$.

In some embodiments, Cy is phenyl.

In some embodiments, X is $NSO_2R^9$ and Y is $CH_2$.

In some embodiments, X is $NSO_2CH_3$, Y is $CH_2$, Cy is phenyl, m is 0, and n is 1.

In some embodiments, X and Y taken together are $CR^9$=$CR^9$, Cy is phenyl, m is 0, and n is 1.

In some embodiments, $R^3$ is H or methyl.

In some embodiments;
$R^1$ is aryl($C_0$-$C_6$ alkyl)-K-($C_1$-$C_6$ alkyl), aryl($C_1$-$C_6$ alkyl), or heteroaryl;
$R^2$ is $R^8$ is $C_1$-$C_6$ alkyl substituted with $R^9$ or $N(R^5)_2$;
$R^3$ is H or Me;
X is $NSO_2CH_3$, or taken together with Y is $CR^9$=$CR^9$;
Y is $CH_2$, or taken together with x is $CR^9$=$CR^9$;
Cy is phenyl; and
n is 1.

In some embodiments, $R_8$ is $C_2$ or $C_3$ alkyl substituted with $R^9$ or $N(R^5)_2$.

In some embodiments, $R^8$ is substituted with a nitrogen containing heterocyclyl, or a substituent selected from the group consisting of

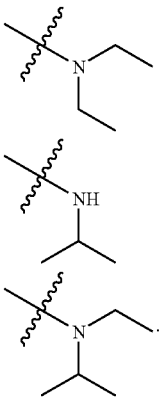 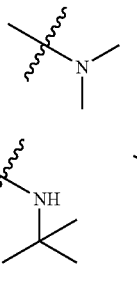 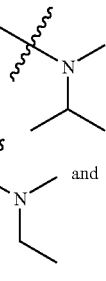

and additional groups

In some embodiments, $R^1$ is benzyloxy or benzyl.

In some embodiments, m is 0.

In some embodiments,
$R^1$ is benzyloxy;
$R^8$ is $C_1$-$C_6$ alkyl substituted with $R^9$ or $N(R^5)_2$;
$R^3$ is H or Me;
X is $NSO_2CH_3$, or taken together with Y is $CR^9$=$CR^9$;
Y is $CH_2$, or taken together with x is $CR^9$=$CR^9$;
Cy is phenyl; and
n is 1.

In some embodiments,
$R^1$ is aryl($C_0$-$C_6$ alkyl)-K-($C_1$-$C_6$ alkyl), aryl($C_1$-$C_6$ alkyl), or heteroaryl;
$R^8$ is $C_2$-$C_3$ alkyl substituted with heterocyclyl or $N(R^5)_2$;
$R^3$ is H or Me;
X is $NSO_2CH_3$, or taken together with Y is $CR^9$=$CR^9$;
Y is $CH_2$, or taken together with x is $CR^9$=$CR^9$;
Cy is phenyl; and
n is 1.

In some embodiments, $R^8$ is substituted with $N(R^5)_2$ or a nitrogen containing heterocyclyl.

In some embodiments, $N(R^5)_2$ is selected from the group consisting of

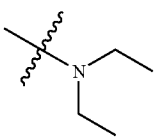 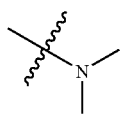 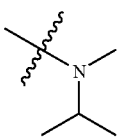

-continued

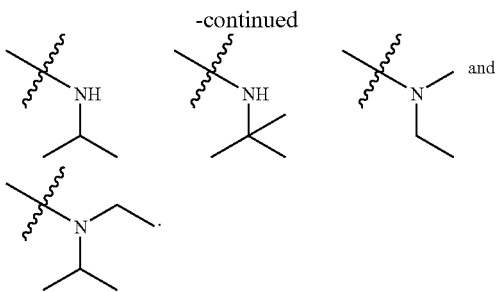

In some embodiments,
$R^1$ is aryl($C_0$-$C_6$ alkyl)-K-($C_1$-$C_6$ alkyl), aryl($C_1$-$C_6$ alkyl), or heteroaryl;
$R^8$ is $C_1$-$C_6$ alkyl substituted with $R^9$ or $N(R^5)_2$;
$R^3$ is H or Me;
X is $NSO_2CH_3$;
Y is $CH_2$;
Cy is phenyl; and
n is 1.

In some embodiments,
$R^1$ is aryl($C_0$-$C_6$ alkyl)-K-($C_1$-$C_6$ alkyl), aryl($C_1$-$C_6$ alkyl), or heteroaryl;
$R^8$ is $C_1$-$C_6$ alkyl substituted with $R^9$ or $N(R^5)_2$;
$R^3$ is H or Me;
X and Y taken together are $CR^9$=$CR^9$;
Cy is phenyl;
$R^9$ is H; and
n is 1.

In some embodiments,
$R^1$ is aryl($C_0$-$C_6$ alkyl)-K-($C_1$-$C_6$ alkyl), aryl($C_1$-$C_6$ alkyl), or heteroaryl;
$R^8$ is $C_2$-$C_3$ alkyl substituted with heterocyclyl or $N(R^5)_2$;
$R^3$ is H or Me;
X is $NSO_2CH_3$, or taken together with Y is $CR^9$=$CR^9$;
Y is $CH_2$, or taken together with x is $CR^9$=$CR^9$;
Cy is phenyl;
m is 0; and
n is 1.

In one aspect, the invention features a compound of formula (I)

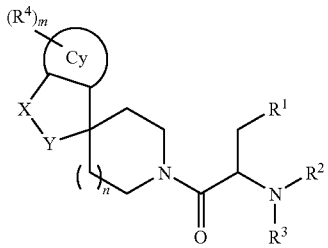

formula (I)

wherein $R^1$ is H, $C_1$-$C_{10}$ alkyl, aryl, aryl($C_1$-$C_6$ alkyl), heteroaryl, heteroaryl($C_1$-$C_6$ alkyl), cycloalkyl, cycloalkyl($C_1$-$C_6$ alkyl), heterocyclyl, heterocyclyl($C_1$-$C_6$ alkyl), ($C_1$-$C_6$ alkyl)-K-($C_0$-$C_6$ alkyl), aryl($C_0$-$C_6$ alkyl)-K-($C_0$-$C_6$ alkyl), heteroaryl($C_0$-$C_6$ alkyl)-K-($C_0$-$C_6$ alkyl), cycloalkyl($C_0$-$C_6$ alkyl)-K-($C_0$-$C_6$ alkyl), or heterocyclyl($C_0$-$C_6$ alkyl)-K-($C_0$-$C_6$ alkyl); wherein $R^1$ can be taken together with one or both of $R^2$ and $R^3$ and the carbon to which it is attached to form a heterocyclyl or heteroaryl ring structure; wherein K is O, S, SO, $SO_2$, $N(R^5)C(O)$, $C(O)N(R^5)$, $OC(O)$, $C(O)O$, $CR^5$=$CR^5$, or C≡C; wherein each alkyl can be independently substituted with at least one halo, $C_1$-$C_6$ alkyl, acetyl, $SO_2R^6$, $OR^6$, $CO_2R^6$; and wherein each aryl, heteroaryl, cycloalkyl or heterocyclyl can be independently substituted with aryl, aryloxy, $C_1$-$C_6$ alkyl, halo, $OR^6$, $SO_2R^6$, $CF_3$, $OCF_3$, $NO_2$, $N(R^5)_2$, $N(R^5)C(O)(R^5)$, $C(O)OR^6$, $OC(O)R^5$, $C(O)N(R^5)_2$, $SO_2N(R^5)_2$, or $N(R^5)SO_2(R^5)$;

$R^2$ is $(CH_2)_mR^7$, $COR^8$, $SO_2R^8$, $CONR^3R^8$, or $CSNR^3R^8$; and wherein $R^2$ can be taken together with one or both of $R^1$ and $R^3$ and the nitrogen to which it is attached to form a heterocyclyl or heteroaryl ring structure;

$R^3$ is H, OH, ($C_1$-$C_6$ alkyl)oxy, $C_1$-$C_6$ alkyl, acetyl, or aryl ($C_1$-$C_6$ alkyl), wherein aryl can be optionally substituted with $R^6$ or $OR^6$; and wherein $R^3$ can be taken together with one or both of $R^1$ and $R^2$ and the nitrogen to which it is attached to form a heterocyclyl or heteroaryl ring structure;

each $R^4$ is independently halo, $C_1$-$C_6$ alkyl, alkoxy, CN, $N(R^6)_2$, acetyl, $CF_3$ or $OCF_3$, $OCH_2CF_3$;

each $R^5$ is independently H, $C_1$-$C_6$ alkyl, acetyl, cycloalkyl, aryl, aryl ($C_1$-$C_6$ alkyl), heteroaryl, or heteroaryl ($C_1$-$C_6$ alkyl); each of which is substituted with one or more $R^4$;

each $R^6$ is independently H or $C_1$-$C_6$ alkyl;

$R^7$ is H, halo, $C_1$-$C_6$ alkyl, aryl, heteroaryl, cycloalkyl, heterocyclyl, $OR^5$, $N(R^5)_2$, $SR^5$, $S(O)R^5$, $SO_2R^5$, $CO_2R^5$, $N(R^5)C(O)R^5$, $C(O)N(R^5)_2$; wherein aryl, heteroaryl, cycloalkyl, and heterocyclyl can each be independently substituted with $C_1$-$C_6$ alkyl, halo, $OR^5$, CN, $NO_2$, $N(R^5)_2$, $CO_2R^5$, $N(R^5)C(O)R^5$, $C(O)N(R^5)_2$, $SR^5$, $SO_2R^5$, $S(O)R^5$, or $SO_2N(R^5)_2$;

each $R^8$ is independently cycloalkyl, cycloalkyl ($C_1$-$C_6$ alkyl), heterocyclyl, heterocyclyl ($C_1$-$C_6$ alkyl), aryl, aryl ($C_1$-$C_6$ alkyl), heteroaryl, heteroaryl ($C_1$-$C_6$ alkyl), $C_1$-$C_6$ alkyl, $C_2$-$C_6$ alkenyl, $C_2$-$C_6$ alkynyl; each of which is independently substituted with $R^9$, halo, $C_1$-$C_6$ alkyl, $OR^5$, CN, $NO_2$, $N(R^5)_2$, $C(O)R^5$, $C(O)OR^5$, $OC(O)R^5$, $N(R^5)C(O)R^5$, $N(R^5)C(O)R^5$, $C(O)N(R^5)_2$, $SR^5$, $SO_2R^5$, $S(O)R^5$, or $SO_2N(R^5)_2$;

X is $CHC(O)OR^9$, $CHC(O)R^9$, $CHC(O)N(R^9)_2$, $NSO_2R^9$, $CHN(R^9)_2$, CO, $CHN(R^9)SO_2R^9$, $CHCH_2OR^9$, $CHR^9$, $NR^9$, $NC(O)R^9$, $NC(O)OR^9$, $NC(O)NR^3R^9$, or when taken together with Y is $CR^9$=$CR^9$;

Y is $(CH_2)_p$, $CHC_1$-$C_8$ alkyl, O, CO, or when taken together with X is $CR^9$=$CR^9$, wherein when Y is O, X is C;

each $R^9$ is independently H, $C_1$-$C_6$ alkyl, aryl ($C_1$-$C_6$) alkyl, cycloalkyl ($C_0$-$C_6$)alkyl, heterocyclyl ($C_0$-$C_6$)alkyl, aryl ($C_0$-$C_6$)alkyl, or heteroaryl ($C_0$-$C_6$)alkyl; each of which can be independently substituted with one or more $R^{10}$;

each $R^{10}$ is independently H, $C_1$-$C_6$ alkyl, aryl ($C_1$-$C_6$) alkyl, cycloalkyl ($C_0$-$C_6$)alkyl, heterocyclyl ($C_0$-$C_6$)alkyl, aryl ($C_0$-$C_6$)alkyl, or heteroaryl ($C_0$-$C_6$)alkyl, halo, $OR^5$, $NR^4SO_2R^5$, $N(R^5)_2$, CN, $C(O)OR^5$, $OC(O)R^5$, $COR^5$, $NO_2$, $SO_2N(R^5)_2$, $SO_2R^5$, $S(O)R^5$, $SR^5$, $CF_3$, $CH_2CF_3$ or $OCF_3$;

Cy is aryl or heteroaryl;
m is 0-6;
n is 0, 1, or 2; and
p is 1, 2 or 3.

In one embodiment, the compound of formula (I) has one or more of the following functions: a) antagonizes GHS-R, e.g., having a $K_i$<1 mM; b) decreases appetite in a fast refeed model for at least 0.5, 1, 2, 4, 6, 8, 12, or 24 hours; c) effectively decreases appetite in a subject; or d) effectively ameliorates at least one symptom of a disorder described herein.

In still another embodiment, $R^2$ is $SO_2R^8$, wherein $R^8$ is not di-chloropheny when $R^8$ is benzyloxy.

In another embodiment, R¹ is aryl(C₁-C₆ alkyl), heteroaryl(C₁-C₆ alkyl), cycloalkyl(C₁-C₆ alkyl), heterocyclyl(C₁-C₆ alkyl), (C₁-C₆ alkyl)-K-(C₁-C₆ alkyl), aryl(C₀-C₆ alkyl)-K-(C₁-C₆ alkyl), heteroaryl(C₀-C₆ alkyl)-K-(C₀-C₆ alkyl), cycloalkyl(C₀-C₆ alkyl)-K-(C₀-C₆ alkyl), or heterocyclyl(C₀-C₆ alkyl)-K-(C₀-C₆ alkyl); wherein K is O, N, or S; wherein each alkyl can be independently substituted with at least one halo, $C_1$-$C_6$ alkyl, acetyl, $SO_2R^6$, $OR^6$, $CO_2R^6$; and wherein each aryl, heteroaryl, cycloalkyl or heterocyclyl can be independently substituted with aryl, aryloxy, $C_1$-$C_6$ alkyl, halo, $OR^6$, $SO_2R^6$, $CF_3$, $OCF_3$, $NO_2$, $N(R^5)_2$, $N(R^5)C(O)(R^5)$, $C(O)OR^6$, $OC(O)R^5$, $C(O)N(R^5)_2$, $SO_2N(R^5)_2$, or $N(R^5)SO_2(R^5)$; and R² is $SO_2R^8$, wherein R⁸ is not di-chlorophenyl when R¹ is benzyloxy.

In still another embodiment, R¹ is aryl, heteroaryl, aryl(C₁-C₆ alkyl), heteroaryl(C₁-C₆ alkyl), cycloalkyl(C₁-C₆ alkyl), heterocyclyl(C₁-C₆ alkyl), (C₁-C₆ alkyl)-K-(C₁-C₆ alkyl), aryl(C₀-C₆ alkyl)-K-(C₁-C₆ alkyl), heteroaryl(C₀-C₆ alkyl)-K-(C₀-C₆ alkyl), cycloalkyl(C₀-C₆ alkyl)-K-(C₀-C₆ alkyl), or heterocyclyl(C₀-C₆ alkyl)-K-(C₀-C₆ alkyl); wherein K is O, N, or S; wherein each alkyl can be independently substituted with at least one halo, $C_1$-$C_6$ alkyl, acetyl, $SO_2R^6$, $OR^6$, $CO_2R^6$; and wherein each aryl, heteroaryl, cycloalkyl or heterocyclyl can be independently substituted with aryl, aryloxy, $C_1$-$C_6$ alkyl, halo, $OR^6$, $SO_2R^6$, $CF_3$, $OCF_3$, $NO_2$, $N(R^5)_2$, $N(R^5)C(O)(R^5)$, $C(O)OR^6$, $OC(O)R^5$, $C(O)N(R^5)_2$, $SO_2N(R^5)_2$, or $N(R^5)SO_2(R^5)$;

R² is $SO_2R^8$; and

R⁸ is alkyl substituted with R⁹.

In another embodiment, R¹ is aryl, heteroaryl, aryl(C₀-C₆ alkyl)-K-(C₁-C₆ alkyl), or heteroaryl(C₀-C₆ alkyl)-K-(C₀-C₆ alkyl);

R² is $SO_2R^8$; and

R⁸ is alkyl, substituted with $N(R^9)_2$ or heterocyclyl.

In one embodiment, R¹ is aryl(C₀-C₆ alkyl)-K-(C₁-C₆ alkyl), heteroaryl(C₀-C₆ alkyl)-K-(C₀-C₆ alkyl), cycloalkyl(C₀-C₆ alkyl)-K-(C₀-C₆ alkyl), or heterocyclyl(C₀-C₆ alkyl)-K-(C₀-C₆ alkyl); wherein K is O, N, S, SO₂, or SO; wherein each alkyl can be independently substituted with at least one halo, $C_1$-$C_6$ alkyl, acetyl, $SO_2R^6$, $OR^6$, $CO_2R^6$; and wherein each aryl, heteroaryl, cycloalkyl or heterocyclyl can be independently substituted with aryl, aryloxy, $C_1$-$C_6$ alkyl, halo, $OR^6$, $SO_2R^6$, $CF_3$, $OCF_3$, $NO_2$, $N(R^5)_2$, $N(R^5)C(O)(R^5)$, $C(O)OR^6$, $OC(O)R^5$, $C(O)N(R^5)_2$, $SO_2N(R^5)_2$, or $N(R^5)SO_2(R^5)$;

R² is $COR^8$; and

R⁸ is cycloalkyl, or heterocyclyl; each of which is independently substituted with R⁹, halo, $C_1$-$C_6$ alkyl, $OR^5$, CN, $NO_2$, $N(R^5)_2$, $C(O)R^5$, $C(O)OR^5$, $OC(O)R^5$, $N(R^5)C(O)R^5$, $N(R^5)C(O)OR^5$, $C(O)N(R^5)_2$, $SR^5$, $SO_2R^5$, $S(O)R^5$, or $SO_2N(R^5)_2$.

In another embodiment, R¹ is benzyloxy.

In still another embodiment, R² is $COR^8$; and R⁸ is cycloalkyl or heterocyclyl, wherein heterocyclyl is a 5 or 6 member nitrogen containing moiety, and wherein each cycloalkyl or heterocyclyl is independently substituted with R⁹, halo, $C_1$-$C_6$ alkyl, $OR^5$, CN, $NO_2$, $N(R^5)_2$, $C(O)R^5$, $C(O)OR^5$, $OC(O)R^5$, $N(R^5)C(O)R^5$, $N(R^5)C(O)OR^5$, $C(O)N(R^5)_2$, $SR^5$, $SO_2R^5$, $S(O)R_5$, or $SO_2N(R^5)_2$.

In another instance, R² is $COR^8$; and R⁸ is morpholinyl, piperidinyl, piperazinyl, tetrahydro-pyridinyl, pyrrolidinyl, or dihydropyrrolidinyl, each of which is optionally substituted with halo or $C_1$-$C_6$ alkyl.

In another instance, R² is $COR^8$ and R⁸ is cycloalkyl substituted with $N(R^9)_2$.

In one instance, R² is

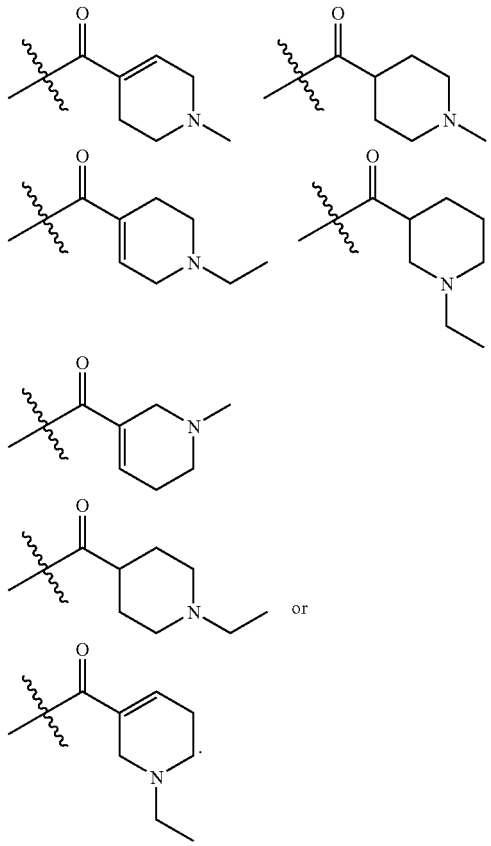

In yet another instance, R¹ is aryl(C₀-C₆ alkyl)-K-(C₁-C₆ alkyl), heteroaryl(C₀-C₆ alkyl)-K-(C₀-C₆ alkyl), cycloalkyl(C₀-C₆ alkyl)-K-(C₀-C₆ alkyl), or heterocyclyl(C₀-C₆ alkyl)-K-(C₀-C₆ alkyl); wherein K is O, S, SO₂, or SO; wherein each alkyl can be independently substituted with at least one halo, $C_1$-$C_6$ alkyl, acetyl, $SO_2R^6$, $OR^6$, $CO_2R^6$; and wherein each aryl, heteroaryl, cycloalkyl or heterocyclyl can be independently substituted with aryl, aryloxy, $C_1$-$C_6$ alkyl, halo, $OR^6$, $SO_2R^6$, $CF_3$, $OCF_3$, $NO_2$, $N(R^5)_2$, $N(R^5)C(O)(R^5)$, $C(O)OR^6$, $OC(O)R^5$, $C(O)N(R^5)_2$, $SO_2N(R^5)_2$, or $N(R^5)SO_2(R^5)$;

R² is $COR^8$;

X is $NSO_2CH_3$;

Y is $CH_2$;

Cy is phenyl;

m is 0; and n is 1.

In still another instance, R¹ is aryl(C₀-C₆ alkyl)-K-(C₁-C₆ alkyl), heteroaryl(C₀-C₆ alkyl)-K-(C₀-C₆ alkyl), cycloalkyl(C₀-C₆ alkyl)-K-(C₀-C₆ alkyl), or heterocyclyl(C₀-C₆ alkyl)-K-(C₀-C₆ alkyl); wherein K is O, S, SO₂, SO, or CO; wherein each alkyl can be independently substituted with at least one halo, $C_1$-$C_6$ alkyl, acetyl, $SO_2R^6$, $OR^6$, $CO_2R^6$; and wherein each aryl, heteroaryl, cycloalkyl or heterocyclyl can be independently substituted with aryl, aryloxy, $C_1$-$C_6$ alkyl, halo, $OR^6$, $SO_2R^6$, $CF_3$, $OCF_3$, $NO_2$, $N(R^5)_2$, $N(R^5)C(O)(R^5)$, $C(O)OR^6$, $OC(O)R^5$, $C(O)N(R^5)_2$, $SO_2N(R^5)_2$, or $N(R^5)SO_2(R^5)$;

R² is COR⁸;

R⁸ is heterocyclyl substituted with R⁹, halo, C₁-C₆ alkyl, OR⁵, CN, NO₂, N(R⁵)₂, C(O)R⁵, C(O)OR⁵, OC(O)R⁵, N(R⁵)C(O)R⁵, N(R⁵)C(O)OR⁵, C(O)N(R⁵)₂, SR⁵, SO₂R⁵, S(O)R⁵, or SO₂N(R⁵)₂;

X is NSO₂R¹⁰, NR⁹, NC(O)R⁹, or taken together with Y is CH=CH;

Y is CH₂, or taken together with X is CH=CH;

Cy is phenyl; and n is 1.

In yet another instance, R¹ is aryl(C₁-C₆ alkyl), heteroaryl(C₁-C₆ alkyl), cycloalkyl(C₁-C₆ alkyl), heterocyclyl(C₁-C₆ alkyl), (C₁-C₆ alkyl)-K-(C₁-C₆ alkyl), aryl(C₀-C₆ alkyl)-K-(C₁-C₆ alkyl), heteroaryl(C₀-C₆ alkyl)-K-(C₀-C₆ alkyl), cycloalkyl(C₀-C₆ alkyl)-K-(C₀-C₆ alkyl), or heterocyclyl(C₀-C₆ alkyl)-K-(C₀-C₆ alkyl); wherein K is O; wherein each alkyl can be independently substituted with at least one halo, C₁-C₆ alkyl, acetyl, SO₂R⁶, OR⁶, CO₂R⁶; and wherein each aryl, heteroaryl, cycloalkyl or heterocyclyl can be independently substituted with aryl, aryloxy, C₁-C₆ alkyl, halo, OR⁶, SO₂R⁶, CF₃, OCF₃, NO₂, N(R⁵)₂, N(R⁵)C(O)(R⁵), C(O)OR⁶, OC(O)R⁵, C(O)N(R⁵)₂, SO₂N(R⁵)₂, or N(R⁵)SO₂(R⁵);

R² is COR⁸;

R⁸ is heterocyclyl or cycloalkyl; each of which is optionally substituted with substituted with R⁹, halo, C₁-C₆ alkyl, OR⁵, CN, NO₂, N(R⁵)₂, C(O)R⁵, C(O)OR⁵, OC(O)R⁵, N(R⁵)C(O)R⁵, N(R⁵)C(O)OR⁵, C(O)N(R⁵)₂, SR⁵, SO₂R⁵, S(O)R⁵, or SO₂N(R⁵)₂;

X is NSO₂CH₃;

Y is CH₂;

Cy is phenyl;

m is 0; and n is 1.

In another instance,

R¹ is aryl, heteroaryl, aryl(C₀-C₆ alkyl)-K-(C₁-C₆ alkyl), heteroaryl(C₀-C₆ alkyl)-K-(C₀-C₆ alkyl);

R² is COR⁸;

R³ is H, or C₁-C₆ alkyl;

R⁸ is heterocyclyl, the heterocyclyl having at least one ring nitrogen and the heterocyclyl being substituted with R⁹, halo, C₁-C₆ alkyl, OR⁵, CN, NO₂, N(R⁵)₂, C(O)R⁵, C(O)OR⁵, OC(O)R⁵, N(R⁵)C(O)R⁵, N(R⁵)C(O)OR⁵, C(O)N(R⁵)₂, SR⁵, SO₂R⁵, S(O)R⁵, or SO₂N(R⁵)₂; wherein when R¹ is phenyl or chlorosubstituted phenyl, R² is not

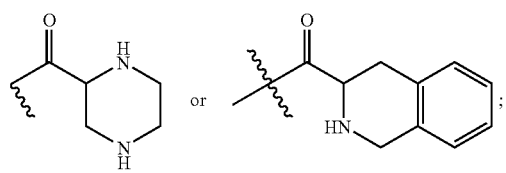

X is NSO₂R¹⁰;

Y is CH₂;

Cy is phenyl;

m is 0; and n is 1.

Still another embodiment features a compound of formula (II),

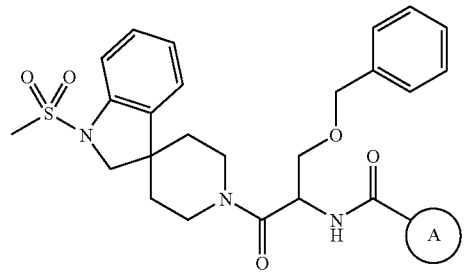

wherein A is cycloalkyl or a nitrogen containing heterocyclyl optionally substituted with aryl, aryloxy, C₁-C₆ alkyl, halo, OR, SO₂R, CF₃, OCF₃, NO₂, N(R⁵)₂, N(R⁵)C(O)(R⁵), C(O)OR⁵, OC(O)R⁵, C(O)N(R⁵)₂, SO₂N(R⁵)₂, N(R⁵)SO₂ aryl, N(R⁵)SO₂ alkyl, N(R⁵)SO₂(R⁵).

In some instances, A is

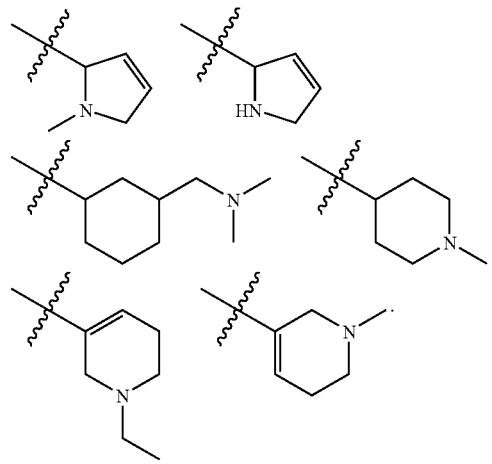

In another instance, R¹ is aryl(C₀-C₆ alkyl)-K-(C₁-C₆ alkyl), heteroaryl(C₀-C₆ alkyl)-K-(C₀-C₆ alkyl); R² is COR⁸; and R⁸ is aryl, heteroaryl, aryl (C₁-C₆ alkyl), or heteroaryl (C₁-C₆ alkyl), each being optionally substituted with R⁹, halo, C₁-C₆ alkyl, OR⁵, CN, NO₂, N(R⁵)₂, C(O)R⁵, C(O)OR⁵, OC(O)R⁵, N(R⁵)C(O)R⁵, N(R⁵)C(O)OR⁵, C(O)N(R⁵)₂, SR⁵, SO₂R⁵, S(O)R⁵, or SO₂N(R⁵)₂.

Yet another instance features a compound of formula (III), formula (III)

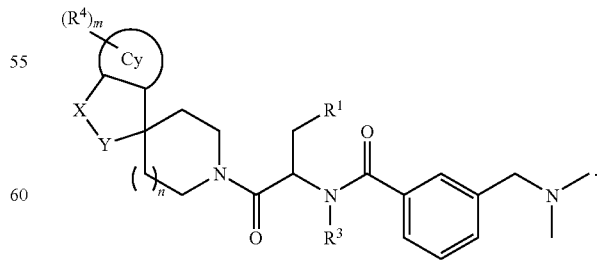

In one instance, R² is CONR³R⁸ or CSNR³R⁸; and each R⁸ is independently cycloalkyl, cycloalkyl (C₁-C₆ alkyl), heterocyclyl, or heterocyclyl (C₁-C₆ alkyl), wherein each is independently substituted with R⁹, halo, C₁-C₆ alkyl, $OR^5$, CN, $NO_2$, $N(R^5)_2$, $C(O)R^5$, $C(O)OR^5$, $OC(O)R^5$, $N(R^5)$ $C(O)R^5$, $N(R^5)C(O)OR^5$, $C(O)N(R^5)_2$, $SR^5$, $SO_2R^5$, $S(O)R^5$, or $SO_2N(R^5)_2$.

In still another embodiment, $R^1$ is aryl, heteroaryl, aryl($C_1$-$C_6$ alkyl), heteroaryl($C_1$-$C_6$ alkyl), cycloalkyl($C_1$-$C_6$ alkyl), heterocyclyl($C_1$-$C_6$ alkyl), ($C_1$-$C_6$ alkyl)-K-($C_1$-$C_6$ alkyl), aryl($C_0$-$C_6$ alkyl)-K-($C_1$-$C_6$ alkyl), heteroaryl($C_0$-$C_6$ alkyl)-K-($C_0$-$C_6$ alkyl), cycloalkyl($C_0$-$C_6$alkyl)-K-($C_0$-$C_6$ alkyl), or heterocyclyl($C_0$-$C_6$ alkyl)-K-($C_0$-$C_6$ alkyl); wherein K is O, N, or S; and wherein each aryl, heteroaryl, cycloalkyl or heterocyclyl can be independently substituted with aryl, aryloxy, $C_1$-$C_6$ alkyl, halo, $OR^6$, $SO_2R^6$, $CF_3$, $OCF_3$, $NO_2$, N($R^5$)$_2$, $N(R^5)C(O)(R^5)$, $C(O)OR^6$, $OC(O)R^5$, $C(O)N(R^5)_2$, $SO_2N(R^5)_2$, or $N(R^5)SO_2(R^5)$; and $R^2$ is $CONR^3R^8$ or $CSNR^3R^8$.

In yet another embodiment, $R^1$ is aryl, heteroaryl, aryl($C_0$-$C_6$ alkyl)-K-($C_1$-$C_6$ alkyl), or heteroaryl($C_0$-$C_6$ alkyl)-K-($C_0$-$C_6$ alkyl);

$R^2$ is $CONR^3R^8$ or $CSNR^3R^8$; and each $R^8$ is independently cycloalkyl, cycloalkyl ($C_1$-$C_6$ alkyl), heterocyclyl, or heterocyclyl ($C_1$-$C_6$ alkyl), each of which is independently substituted with $R^9$, halo, $C_1$-$C_6$ alkyl, $OR^5$, CN, $NO_2$, $N(R^5)_2$, $C(O)R^5$, $C(O)OR^5$, $OC(O)R^5$, $N(R^5)C(O)R^5$, $N(R^5)C(O)OR^5$, $C(O)N(R^5)_2$, $SR^5$, $SO_2R^5$, $S(O)R^5$, or $SO_2N(R^5)_2$.

In another instance, $R^2$ is $(CH_2)_m R^7$;

$R^7$ is cycloalkyl, heterocyclyl, or alkyl substituted with cycloalkyl, heterocyclyl, or $N(R^5)_2$; and m is 0-2.

In still another instance, $R^1$ is aryl, heteroaryl, aryl($C_1$-$C_6$ alkyl), heteroaryl($C_1$-$C_6$ alkyl), cycloalkyl($C_1$-$C_6$ alkyl), heterocyclyl($C_1$-$C_6$ alkyl), ($C_1$-$C_6$ alkyl)-K-($C_1$-$C_6$ alkyl), aryl($C_0$-$C_6$ alkyl)-K-($C_1$-$C_6$ alkyl), heteroaryl($C_0$-$C_6$ alkyl)-K-($C_0$-$C_6$ alkyl), cycloalkyl($C_0$-$C_6$ alkyl)-K-($C_0$-$C_6$ alkyl), or heterocyclyl($C_0$-$C_6$ alkyl)-K-($C_0$-$C_6$ alkyl); wherein K is O, N, or S; and wherein aryl, heteroaryl, cycloalkyl, and heterocyclyl can each be independently substituted with $C_1$-$C_6$ alkyl, halo, $OR^5$, CN, $NO_2$, $N(R^5)_2$, $CO_2R^5$, $N(R^5)C(O)R^5$, $C(O)N(R^5)_2$, $SR^5$, $SO_2R^5$, $S(O)R^5$, or $SO_2N(R^5)_2$;

$R^2$ is $(CH_2)_m R^7$; and $R^7$ is cycloalkyl, heterocyclyl, or alkyl substituted with cycloalkyl, heterocyclyl, or $N(R^5)_2$.

Still another embodiment features a compound of formula (IV)

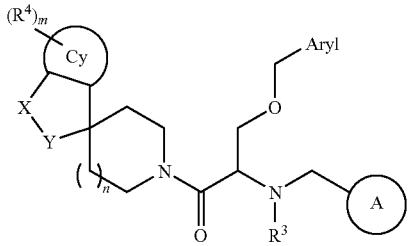

formula (IV)

wherein:

A is cycloalkyl or a nitrogen containing heterocyclyl optionally substituted with aryl, aryloxy, $C_1$-$C_6$ alkyl, halo, OR, $SO_2R$, $CF_3$, $OCF_3$, $NO_2$, $N(R^5)_2$, $N(R^5)C(O)(R^5)$, $C(O)$ $OR^5$, $OC(O)R^5$, $C(O)N(R^5)_2$, $SO_2N(R^5)_2$, $N(R^5)SO_2$ aryl, $N(R^5)SO_2$ alkyl, $N(R^5)SO_2(R^5)$).

In another aspect, the invention features a compound of formula (V)

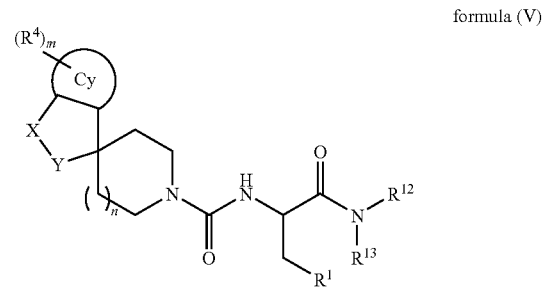

formula (V)

wherein:

$R^1$ is H, $C_1$-$C_{10}$alkyl, aryl, aryl($C_1$-$C_6$ alkyl), heteroaryl, heteroaryl($C_1$-$C_6$ alkyl), cycloalkyl, cycloalkyl($C_1$-$C_6$ alkyl), heterocyclyl, heterocyclyl($C_1$-$C_6$ alkyl), ($C_1$-$C_6$ alkyl)-K-($C_1$-$C_6$ alkyl), aryl($C_0$-$C_6$ alkyl)-K-($C_0$-$C_6$ alkyl), heteroaryl ($C_0$-$C_6$ alkyl)-K-($C_0$-$C_6$ alkyl), cycloalkyl($C_0$-$C_6$ alkyl)-K-($C_0$-$C_6$ alkyl), or heterocyclyl($C_0$-$C_6$ alkyl)-K-($C_0$-$C_6$ alkyl); wherein K is O, S, SO, $SO_2$, $N(R^5)C(O)$, $C(O)N(R^5)$, OC(O), C(O)O, $CR^5$=$CR^5$, or C≡C; wherein $R^1$ can be taken together with one or both of $R^{12}$ and $R^{13}$ and the carbon to which it is attached to form a heterocyclyl or heteroaryl ring structure; wherein each alkyl can be independently substituted with at least one halo, $C_1$-$C_6$ alkyl, acetyl, $SO_2R^6$, $OR^6$, $CO_2R^6$; and wherein each aryl, heteroaryl, cycloalkyl or heterocyclyl can be independently substituted with aryl, aryloxy, $C_1$-$C_6$ alkyl, halo, $OR^6$, $SO_2R^6$, $CF_3$, $OCF_3$, $NO_2$, $N(R^5)_2$, $N(R^5)C(O)(R^5)$, $C(O)OR^6$, $OC(O)R^5$, $C(O)N(R^5)_2$, $SO_2N$ ($R^5$)$_2$, or $N(R^5)SO_2(R^5)$;

each $R^4$ is independently halo, $C_1$-$C_6$ alkyl, alkoxy, CN, acetyl, $CF_3$ or $OCF_3$;

each $R^5$ is independently H, $C_1$-$C_6$ alkyl, acetyl, cycloalkyl, aryl, aryl ($C_1$-$C_6$ alkyl), heteroaryl, or heteroaryl ($C_1$-$C_6$ alkyl); each of which is substituted with one or more $R^4$;

each $R^6$ is H or $C_1$-$C_6$ alkyl;

X is $CHC(O)OR^9$, $CHC(O)R^9$, $CHC(O)N(R^9)_2$, $NSO_2R^9$, $CHN(R^9)_2$, CO, $CHN(R^9)SO_2R^9$, $CHCH_2OR^9$, $CHR^9$, $NR^9$, $NC(O)R^9$, $NC(O)OR^9$, $NC(O)NR^3R^9$, or when taken together with Y is $CR^9$=$CR^9$;

Y is $(CH_2)_p$, $CHC_1$-$C_8$alkyl, O, CO, or when taken together with X is $CR^9$=$CR^9$, wherein when Y is O, X is C;

$R^9$ is H, $C_1$-$C_6$ alkyl, aryl ($C_1$-$C_6$) alkyl, cycyl ($C_0$-$C_6$) alkyl, heterocyclyl ($C_0$-$C_6$)alkyl, aryl ($C_0$-$C_6$)alkyl, or heteroaryl ($C_0$-$C_6$)alkyl; each of which can be independently substituted with one or more $R^{10}$;

$R^{10}$ is H, $C_1$-$C_6$ alkyl, aryl ($C_1$-$C_6$) alkyl, cycyl ($C_0$-$C_6$) alkyl, heterocyclyl ($C_0$-$C_6$)alkyl, aryl ($C_0$-$C_6$)alkyl, or heteroaryl ($C_0$-$C_6$)alkyl, halo, $OR^5$, $NHSO_2R^5$, $N(R^5)_2$, CN, $CO_2R^5$, $COR^5$, $NO_2$, $SO_2N(R^5)_2$, $SO_2R^5$, $S(O)R^5$, $SR^5$, $CF_3$, or $OCF_3$;

Cy is aryl or heteroaryl;

$R^{12}$ is cycloalkyl, cycloalkyl ($C_1$-$C_6$ alkyl), heterocyclyl, heterocyclyl ($C_1$-$C_6$ alkyl), aryl, aryl ($C_1$-$C_6$ alkyl), heteroaryl, heteroaryl ($C_1$-$C_6$ alkyl), $C_1$-$C_6$ alkyl, $C_2$-$C_6$ alkenyl, $C_2$-$C_6$alkynyl; wherein $R^{12}$ can be taken together with one or both of $R^1$ and $R^{13}$ and the nitrogen to which it is attached to form a heterocyclyl or heteroaryl ring structure; and wherein each of which is substituted with halo, $C_1$-$C_6$ alkyl, hydroxy, $C_1$-$C_6$ alkoxy, CN, $NO_2$, $N(R^5)_2$, $CO_2R^6$, $COR^5$, $N(R^5)C(O)$ $R^5$, $C(O)N(R^5)_2$, $SR^5$, $SO_2R^5$, $S(O)R^5$, $SR^5$, or $SO_2N(R^5)_2$;

$R^{13}$ is H, OH, ($C_1$-$C_6$ alkyl)oxy, $C_1$-$C_6$ alkyl, acetyl, aryl ($C_1$-$C_6$ alkyl); wherein $R^{12}$ can be taken together with one or both of $R^1$ and $R^{12}$ and the nitrogen to which it is attached to form a heterocyclyl or heteroaryl ring structure;

m is 0-4; n is 0, 1, or 2; and p is 1, 2 or 3.

In one embodiment, the compound has one or more of the following functions: a) antagonizes GHS-R, e.g., having a $K_i$<1 mM; b) decreases appetite in a fast refeed model for at least 0.5, 1, 2, 4, 6, 8, 12, or 24 hours; c) effectively decreases appetite in a subject; or d) effectively ameliorates at least one symptom of a disorder described herein.

In one embodiment, $R^1$ is aryl, aryl($C_1$-$C_6$ alkyl), heteroaryl, heteroaryl($C_1$-$C_6$ alkyl), heterocyclyl, heterocyclyl ($C_1$-$C_6$ alkyl), aryl($C_0$-$C_6$ alkyl)-K-($C_1$-$C_6$ alkyl), heteroaryl ($C_0$-$C_6$alkyl)-K-($C_0$-$C_6$ alkyl), or heterocyclyl($C_0$-$C_6$ alkyl)-K-($C_0$-$C_6$ alkyl); wherein K is O, S, SO, $SO_2$; wherein each aryl, heteroaryl, cycloalkyl or heterocyclyl can be independently substituted with aryl, aryloxy, $C_1$-$C_6$ alkyl, halo, OR, $SO_2R$, $CF_3$, $OCF_3$, $NO_2$, $N(R^5)_2$, $N(R^5)C(O)(R^5)$, $C(O)OR^5$, $OC(O)R^5$, $C(O)N(R^5)_2$, $SO_2N(R^5)_2$, $N(R^5)SO_2$ aryl, $N(R^5)SO_2$ alkyl, $N(R^5)SO_2(R^5)$; and $R^{12}$ is cycloalkyl, cycloalkyl ($C_1$-$C_6$ alkyl), heterocyclyl, heterocyclyl ($C_1$-$C_6$ alkyl), aryl, aryl ($C_1$-$C_6$ alkyl), heteroaryl, heteroaryl ($C_1$-$C_6$ alkyl), or a saturated, unsaturated or partially saturated heterocyclic ring when taken together with $R^{13}$ and the nitrogen to which it is attached.

In one embodiment, the compound has formula (VI)

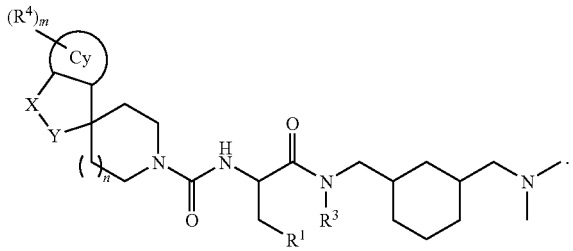

formula (VI)

In one aspect, the invention features a compound that has a structure of formula I or formula V or other structure described herein, and the compound competes with ghrelin for binding to GHS-R.

In another aspect, the invention features a compound that has a structure of formula I or formula V or other structure described herein, and the compound is effective for altering appetite of a subject or for altering feeding behavior of the subject.

In another aspect, the invention features a method of treating obesity in a subject using a compound described herein. The method includes administering to the subject a compound described herein or a pharmaceutically acceptable salt thereof.

In another aspect, the invention features a method of treating diabetes in a subject. The method includes administering to the subject a compound described herein or a pharmaceutically acceptable salt thereof. In some instances, the diabetes is type I diabetes or type II diabetes. In some instances, the subject is identified as being at risk of diabetes. For example, the subject can be identified as being at risk of diabetes by having impaired glucose tolerance by having fasting hyperglycemia.

In another aspect, the invention features a method of treating metabolic syndrome in a subject. The method includes administering to the subject a compound described herein or a pharmaceutically acceptable salt thereof. In some instances, the subject has atherogenic dyslipidemia. In some instances, the subject is obese.

In another aspect, the invention features a compound that has a structure of formula I or formula V or other structure described herein, and the compound is effective for modulating resistin, leptin, or adiponectin mRNA in white adipose tissue (WAT) or for modulating levels of insulin, IGF-1, GH, cortisol, triglycerides, free fatty acids, cholesterols (e.g., VLDL or HLDL particles) or glucose, e.g., in the blood.

In another aspect, the invention features a compound that has a structure of formula I or formula V or other structure described herein, and the compound is effective for inhibiting growth of a neoplastic cell, e.g., a cell of a ghrelin-sensitive neoplastic disorder or a GHS-R antagonist-sensitive neoplastic disorder.

In another aspect, the invention features a compound listed in Table 1.

In another aspect, the invention features an organic compound that antagonizes GHS-R activity, the compound having a molecular weight of less than 700 Daltons, and having fewer than four L- or D-amino acids (e.g., and any salt thereof). For example, the compound may, in certain embodiments, associate with, bind, or otherwise include a metal cation.

In one embodiment, the organic compound includes a spirocyclic moiety. In one embodiment, the compound has a molecular weight less than [D-Lys-3]-GHRP-6 or L-756,867 or within 2, 1.5, 1.4, 1.2, 1.1, 0.8, 0.6, or 0.5 fold that of [D-Lys-3]-GHRP-6 or L-756,867. In one embodiment, the compound includes a structure compatible with the GHS-R.

In another aspect, the invention features a pharmaceutical composition that includes a compound described herein, e.g., a compound listed in Table 1 or described above, and a pharmaceutically acceptable carrier.

In another aspect, the invention features a method of decreasing GHS-R activity in a subject. The method includes administering the compound described herein to the subject in an amount effective to decrease GHS-R activity in the subject. In one embodiment, the subject is a mammal, e.g., a human, a primate, a dog, a cat, or an agricultural mammal. In one embodiment, the subject is overweight or obese.

In one embodiment, GHS-R activity is modulated in one or more of the following tissues: pituitary, brain, spinal cord, uterus, spleen, pancreas, kidney, adrenal gland, skeletal muscle, thyroid, liver, hypothalamus, heart, lung, pancreas, intestine, and adipose tissue.

In another aspect, the invention features a method that includes: identifying a subject as having obesity, being at risk for obesity using established clinical criteria (e.g., NIH Clinical Guidelines on the Identification and Evaluation, and Treatment of Overweight and Obesity in Adults" (1998)), having insulin resistance, or being overweight; and administering a compound described herein, to the subject, in an amount effective to prevent weight gain, reduce fat content, increase metabolic activity, reduce blood glucose concentration or reduce weight.

In another aspect, the invention features a method of treating or preventing an insulin-related disorder, e.g., diabetes. The method includes administering a compound described herein, to the subject, in an amount effective to treat or prevent insulin resistance in the subject.

In another aspect, the invention features a method that includes: administering a compound described herein, to the subject, in an amount effective to reduce GHS-R activity in the subject. In one embodiment, the subject is diagnosed with or has a disorder selected from the group consisting of: feeding disorder, cancer, diabetes, neurological disorder, obesity, age-associated disorder, neoplastic disorder, non-neoplastic disorder, cardiovascular disorder, metabolic disorder, or dermatological disorder.

For example, the compound is administered orally, or parenterally, e.g., by injection, and so forth. In one embodiment, the compound is administered at a plurality of intervals, e.g., regular intervals. In one embodiment, the method further includes monitoring the subject for GH or IGF-1 activity; monitoring the subject for gene or protein regulated by GHS-R (e.g., resistin, leptin, or adiponectin) or monitoring the subject for blood or plasma levels of ghrelin, insulin, leptin and/or IGF-1.

In another aspect, the invention features a method of treating or preventing a disorder characterized by ghrelin levels or GHS-R mediated signalling levels that exceed a desired or normal level. The method includes: administering the compound of class A, C, or D, to a subject, in an amount effective to attenuate, inhibit, or block GHS-R mediating signalling in the subject.

In another aspect, the invention features a method of treating or preventing a disorder characterized by ghrelin levels or GHS-R mediated signalling levels that are below a desired or normal level. The method includes: administering the compound of class B or D, to a subject, in an amount effective to increase GHS-R mediating signalling in the subject, e.g., in one or more of the following tissues pituitary, brain, spinal cord, uterus, spleen, pancreas, kidney, adrenal gland, skeletal muscle, thyroid, liver, small intestine, and heart.

In another aspect, the invention features a method of treating or preventing a GHS-R sensitive neoplastic disorder. The method includes: administering the compound of class A, C, or D, to a subject, in an amount effective to ameliorate the neoplastic disorder (e.g., to inhibit proliferation, kill cells, or reduce or inhibit growth or an activity of neoplastic cells) in the subject.

In another aspect, the invention features a method of modulating feeding behavior in a subject. The method includes: administering the compound of class B or D, to a subject, in an amount effective to modulate a feeding behavior of the subject, e.g., to increase appetite in the subject. In one embodiment, the compound is administered prior to (e.g., at least 0.5, 1, 2, or 4 hours prior to) a mealtime or expected time at which food would be made available. In a related aspect, the method includes administering the compound of class A, C, or D, to a subject, in an amount effective to modulate a feeding behavior of the subject, e.g., to decrease appetite in the subject. In one embodiment, the compound is administered prior to (e.g., at least 0.5, 1, 2, or 4 hours prior to) a mealtime or expected time at which food would be made available.

In another aspect, the invention features a method of treating or preventing a neoplastic disorder in a subject. The method includes: determining if the neoplastic disorder is mediated by cells that are sensitive to ghrelin or a GHS-R agonist or to a GHS-R antagonist, and selecting a GHS-R interacting compound of class A or C if the cells are sensitive to a GHS-R antagonist and selecting a GHS-R compound of class B if the cells are sensitive to a GHS-R agonist; and administering the selected compound to the subject.

In another aspect, the invention features a method of treating or preventing a neurodegenerative disorder. The method includes: administering the compound of class A, C, or D, to a subject, in an amount effective to ameliorate the neurodegenerative disorder in the subject.

In another aspect, the invention features a method of treating or preventing a metabolic disorder. The method includes: administering the compound of class A, C, or D, to a subject, in an amount effective to ameliorate the metabolic disorder in the subject.

In another aspect, the invention features a method of treating or preventing a cardiovascular disorder. The method includes: administering the compound of class A, C, or D, to a subject, in an amount effective to ameliorate the cardiovascular disorder in the subject.

In another aspect, the invention features a kit that includes a compound described herein; and instructions for administering the compound to treat a disorder described herein, e.g., an eating disorder, a metabolic disorder characterized by undesired GHS-R activity, a cardiovascular disorder, a neurodegenerative disorder, and a disorder associated with altered GH/IGF-1 activity.

In another aspect, the invention features a kit that includes (1) a compound described herein; and (2) one or more reagents for monitoring expression of one or more genes regulated by GHS-R, e.g., resistin, leptin, or adiponectin, or one or more reagents for monitoring plasma levels of a metabolic regulator such as ghrelin, insulin, IGF-1 or leptin.

In one aspect, the invention features a method of modulating IGF-1 levels (e.g., circulating IGF-1 levels) in a subject. The method includes administering a compound described herein. In one embodiment, a compound of classification A, B, C, or D is administered to the subject in an amount effect to modulate IGF-1 levels (e.g., increase or decrease IGF-1 levels). In particular, antagonists (such as compounds of class A or C) are believed to be effective for decreasing IGF-1 levels, and agonists (such as compounds of class B) are believed to be effective for increasing IGF-1 levels.

In one aspect, the invention features a method of modulating insulin levels (e.g., circulating insulin levels) in a subject. The method includes administering a compound described herein. In one embodiment, a compound of classification A, B, C, or D is administered to the subject in an amount effect to modulate insulin levels (e.g., increase or decrease insulin levels). In particular, antagonists (such as compounds of class A or C) are believed to be effective for decreasing insulin levels, and agonists (such as compounds of class B) are believed to be effective for increasing insulin levels.

In one aspect, the invention features a method of modulating glucose levels (e.g., circulating or blood glucose levels) in a subject. The method includes administering a compound described herein. In one embodiment, a compound of classification A, B, C, or D is administered to the subject in an amount effect to modulate glucose levels (e.g., increase or decrease glucose levels). In particular, agonists are believed to be effective for increasing glucose levels, and antagonists are believed to be effective for decreasing glucose levels.

The term "halo" refers to any radical of fluorine, chlorine, bromine or iodine. The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. The term "lower alkyl" refers to a $C_1$-$C_8$alkyl chain. In the absence of any numerical designation, "alkyl" is a chain (straight or branched) having 1 to 10 (inclusive) carbon atoms in it. The term "alkoxy" refers to an —O-alkyl radical. The term "alkylene" refers to a divalent alkyl (i.e., —R—). The term "aminoalkyl" refers to an alkyl substituted with an amino. The term "mercapto" refers to an —SH radical. The term "thioalkoxy" refers to an —S-alkyl radical.

The term "alkenyl" refers to a hydrocarbon chain that may be a straight chain or branched chain having one or more carbon-carbon double bonds. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 10 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 10 (inclusive) carbon atoms in it.

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkenyl" refers to an alkenyl substituted with an aryl. The term "arylalkynyl" refers to an alkynyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkenyl" refers to an alkenyl substituted with a heteroaryl. The term "heteroarylalkynyl" refers to an alkynyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. The term "heterocyclylalkyl" refers to an alkyl substituted with a heterocyclyl.

The term "sulfonyl" refers to a sulfur attached to two oxygen atoms through double bonds. An "alkylsulfonyl" refers to an alkyl substituted with a sulfonyl.

The term "amino acid" refers to a molecule containing both an amino group and a carboyxl group. Suitable amino acids include, without limitation, both the D- and L-isomers of the 20 naturally occurring amino acids found in peptides (e.g., A, R, N, C, D, Q, E, G, H, I, L, K, M, F, P, S, T, W, Y, V (as known by the one letter abbreviations)) as well as unnaturally occurring amino acids prepared by organic synthesis or other metabolic routes.

The term "amino acid side chain" refers to any one of the twenty groups attached to the α-carbon in naturally occurring amino acids. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, aryl, aralkyl, alkoxy, thioalkoxy, aryloxy, amino, alkoxycarbonyl, amido, carboxy, alkanesulfonyl, alkylcarbonyl, and cyano groups.

GHS-R can regulate the secretion of GH. GH itself is a regulator of IGF-1 production. Thus, compounds, e.g., compounds described herein, that modulate GHS-R activity can be used to modulate (e.g., increase or decrease) activity of the GH/IGF-1 axis. For example, agonists of GHS-R can be used to increase GH activity and/or IGF-1 activity. Antagonists of GHS-R can be used to decrease GH activity and/or IGF-1 activity. This application also incorporates by reference U.S. Ser. No. 10/656,530, the contents of which include uses for which a compound described herein may be used, e.g., as a modulator of the GH/IGF-1 axis.

The GH/IGF-1 axis includes a series of extracellular and intracellular signalling components that have as a downstream target, the transcription factor Forkhead. Major components of the GH/IGF-1 axis can be divided into three categories: pre-IGF-1, IGF-1, and post-IGF-1 components. "Pre-IGF-1 components" include GH, GH-R, ghrelin, GHS-R, GHRH, GHRH-R, SST, and SSTR. "Post-IGF-1 components" include IGF-1-R and intracellular signalling components including PI(3) kinase, PTEN phosphatase, $PI(3,4)P_2$, 14-3-3 protein, and $PI(3,4,5)P_3$ phosphatidyl inositol kinases, AKT serine/threonine kinase (e.g., AKT-1, AKT-2, or AKT-3), or a Forkhead transcription factor (such as FOXO-1, FOXO-3, or FOXO-4). A "somatotroph axis signalling pathway component" refers to a protein that is one of the following: (i) a protein that is located in a somatotroph and that regulates GH release by the somatotroph, or (ii) a protein that directly binds to a protein in class (i). Exemplary somatotroph axis signalling pathway components of class (i) include cell surface receptors such as GHS-R, GHRH-R, and SST-R. Exemplary somatotroph axis signalling pathway components of class (ii) include GHRH, ghrelin, and SST.

A compound that modulates GH levels, e.g., by altering GHS-R activity can have downstream effects. For example, the compound can alter (e.g., increase or decrease) the levels or activity of an IGF-1 receptor signaling pathway effector. A "IGF-1 Receptor signalling pathway effector" refers to a protein or other biologic whose levels are directly regulated by a Forkhead transcription factor in response to IGF-1. For example, expression of the gene encoding the protein can be directly regulated by a Forkhead transcription factor such as FOXO-1, FOXO-3a, or FOXO-4. Exemplary IGF-1 Receptor signalling pathway effector can include: GADD45, PA26, Selenoprotein P, Whip1, cyclin G2, and NIP3.

As used herein, "activity of the GH/IGF-1 axis" refers to the net effect of the axis components with respect to ability to stimulate GH secretion, increase IGF-1 levels, or increase IGF-1 receptor signalling. Accordingly, "downregulating the GH/IGF-1 axis" refers to modulating one or more components such that one or more of the following is reduced, e.g., decreased GH, decreased IGF-1, or decreased IGF-1 receptor signalling. For example, in some instances, GH levels are maintained but its action is inhibited; thus IGF-1 levels are decreased without decreasing GH levels. In some instances, both GH and IGF-1 levels are decreased.

An "antagonist" of a particular protein includes compounds that, at the protein level, directly bind or modify the subject component such that an activity of the subject component is decreased, e.g., by competitive or non-competitive inhibition, destabilization, destruction, clearance, or otherwise. For example, the decreased activity can include reduced ability to respond to an endogenous ligand. For example, an antagonist of GHS-R can reduce the ability of GHS-R to respond to ghrelin.

An "agonist" of a particular protein includes compounds that, at the protein level, directly bind or modify the subject component such that an activity of the subject component is increased, e.g., by activation, stabilization, altered distribution, or otherwise.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

Certain compounds that agonize GHS-R to a lesser extent than ghrelin can function in assays as antagonists as well as agonists. These compounds antagonize activation of GHS-R by ghrelin because they prevent the full effect of ghrelin-receptor interaction. However, the compounds also, on their own, activate some receptor activity, typically less than a corresponding amount of ghrelin. Such compounds may be referred to as "partial agonists of GHS-R" and may include compounds designated as class D in Table 1.

A subject with "normal" GH levels is one who would return a normal result using the glucose tolerance test in which glucose is ingested and blood levels of GH are measured by radioimmunoassay (RIA) or polyclonal immunoassay. A normal result for this test is characterized by less than 1 ng/mL of GH within 1 to 2 hours of an oral glucose load. However, GH levels of a subject with excessive GH, as in one with acromegaly may not decrease below 1 ng/mL after ingesting glucose. Because GH levels oscillate every twenty to thirty minutes and varies in level according to the time of day, stress level, exercise, etc., a standard means of determining if GH levels are excessive is to administer glucose. This approach normalizes GH and is less affected by the pulsatility of GH, age, gender, or other factors. Alternatively or as a confirmation, since IGF-1 levels are invariably increased in acromegalic individuals, IGF-1 levels can be measured and compared to age and gender matched normal controls.

The term "an indicator of GH/IGF-1 axis activity" refers to a detectable property of the GH/IGF-1 axis that is indicative of activity of the axis. Exemplary properties include circulating GH concentration, circulating IGF-1 concentration, frequency of GH pulses, amplitude of GH pulses, GH concentration in response to glucose, IGF-1 receptor phosphorylation, and IGF-1 receptor substrate phosphorylation. A compound that modulates activity of GHS-R can alter one or more indicators of GH/IGF-1 axis activity.

Abbreviations:

GH, Growth Hormone; GH-R, Growth Hormone Receptor; IGF, Insulin-like Growth Factor; GHRH, GH Releasing Hormone; GHRH-R, GH Releasing Hormone Receptor; GHS, GH Secretagogue; GHS-R, GH Secretagogue Receptor; SST, Somatostatin; SST-R, Somatostatin Receptor; PI, phosphoinositol; AGRP, agouti related protein; ARC, arcuate nucleus; ICV, intra-third cerebroventricular(ly); NPY, neuropeptide Y; WAT, white adipose tissue. Bn, benzyl; Boc, $^t$Butyloxycarbonyl; Cbz, Benzyloxycarbonyl; DCM, dichloromethane; DIPEA, diisopropylethylamine; DMF, dimethylformamide; EDC, 1-(3-dimethylaminopropyl)-3-ethylcarbodiimide hydrochloride; EtOAc, ethyl acetate; h, hours; HOBT, hydroxybenzotriazole; Ms, methanesulfonyl; Prep LC, preparative high pressure liquid chromatography; RT, room temperature; TFA, trifluoroacetic acid; THF, tertrahydrofuran The details of one or more embodiments of the invention are set forth in the accompanying drawings and the description below. Other features, objects, and advantages of the invention will be apparent from the description and drawings, and from the claims.

DETAILED DESCRIPTION

Figure 1:
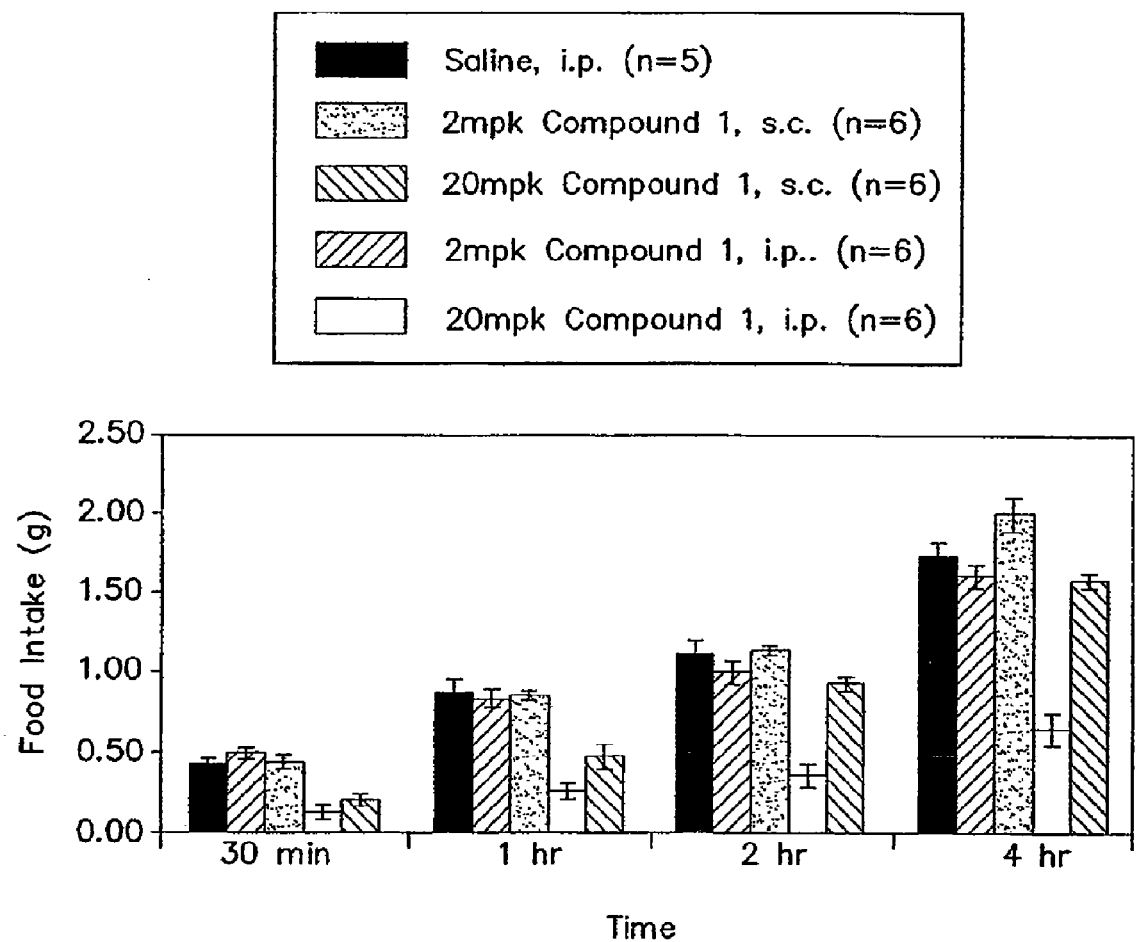
FIG. 1 depicts Cumulative Food Intake in Lean Male C57Bl/6 Mice Following Acute Dosing with Compound 1 (Fast Refeed Model).
Figure 2:
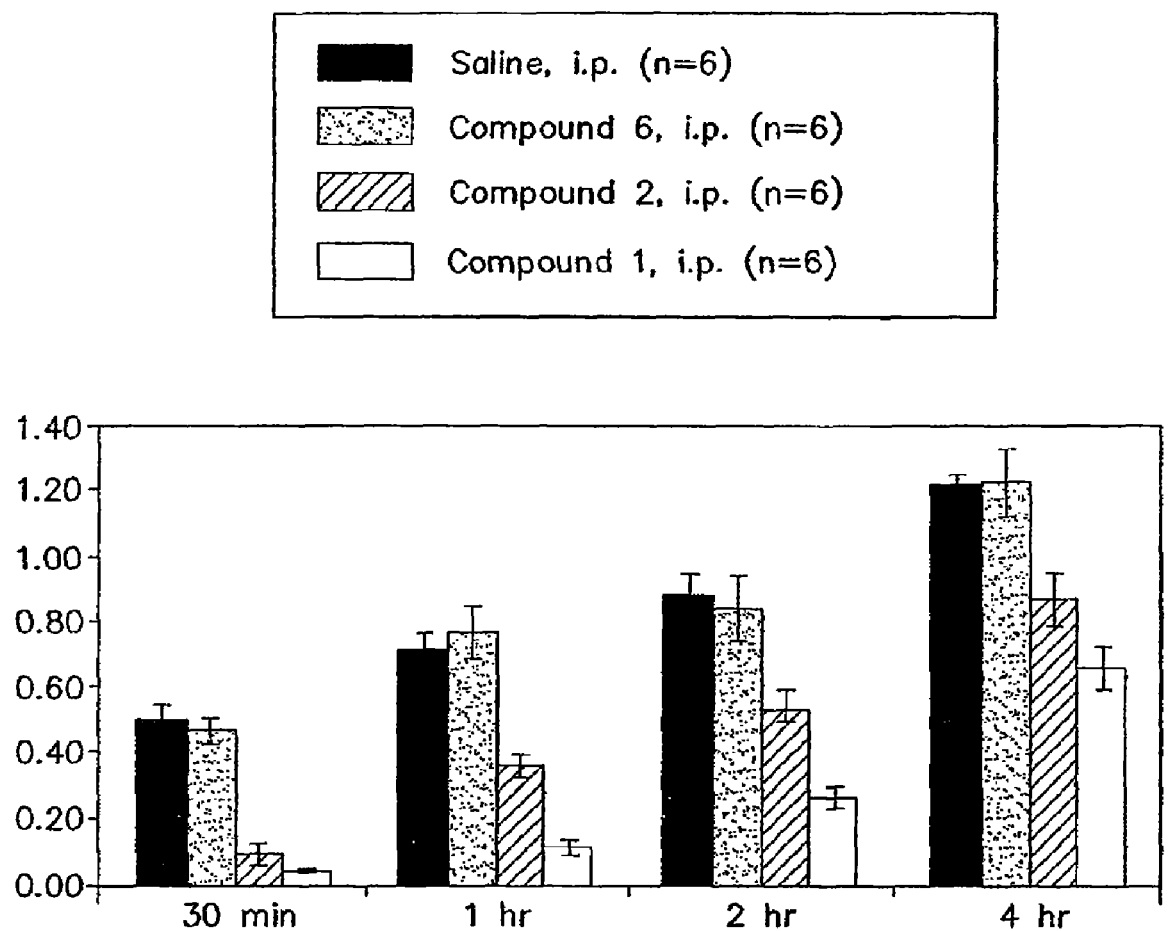
FIG. 2 depicts Cumulative Food Intake in Lean Male C57Bl/6 Mice Following Acute Dosing with Compound 1, 2, and 6 (Fast-Refeed Model).
Figure 3:
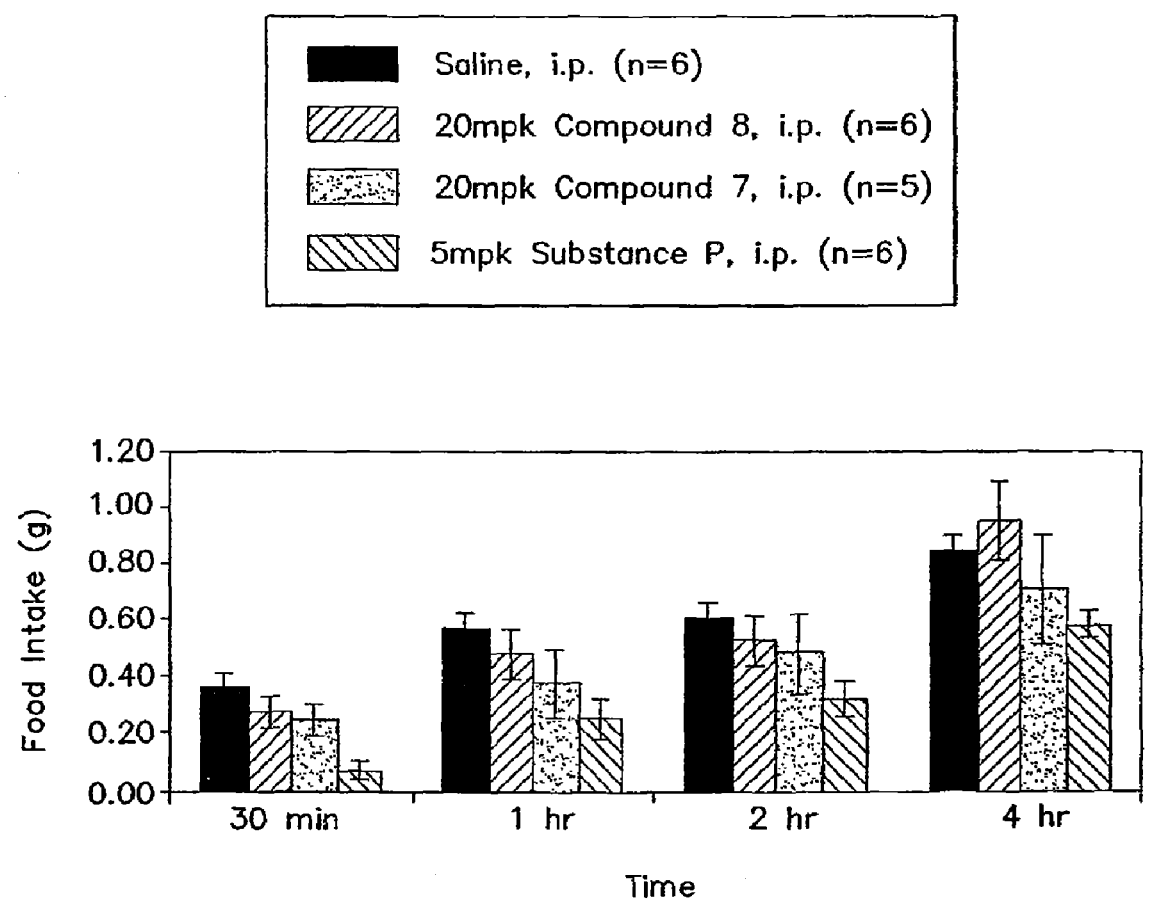
FIG. 3 depicts Cumulative Food Intake in Lean Male C57Bl/6 Mice Following Acute Dosing with Compound 7 and 8 (Fast-Refeed Model).

The compounds described herein can be used for a variety of purposes, e.g., therapeutic purposes. Many of the compounds antagonize GHS-R activity and can be used to reduce GHS-R activity, e.g., in a subject. Still other compounds agonize GHS-R and can be used to increase GHS-R activity, e.g., in a subject. Some of the disclosed compounds may also provide useful biological effects by modulating the activity of cellular components other than GHS-R.

Representative compounds of the invention are depicted below in Table 1. Other exemplary compounds are within the scope set forth in the Summary or are described elsewhere herein.

TABLE 1

Representative compounds of the invention[A, B, C, D]

| Number | Structure | | Activity |
|---|---|---|---|
| 1 | 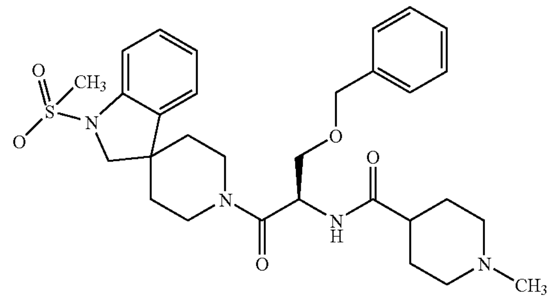 | | A |
| 2 | 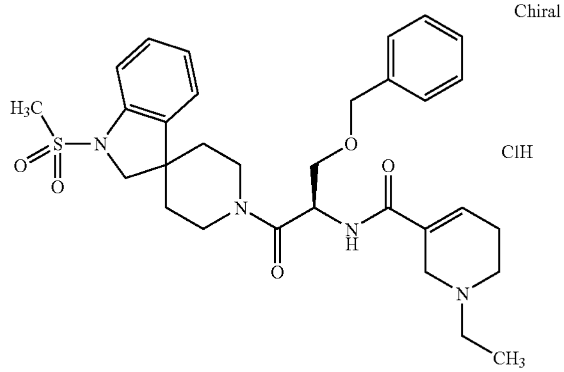 | Chiral ClH | D |
| 3 | 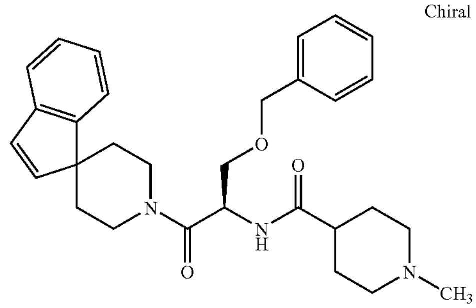 | Chiral | A |
| 4 | 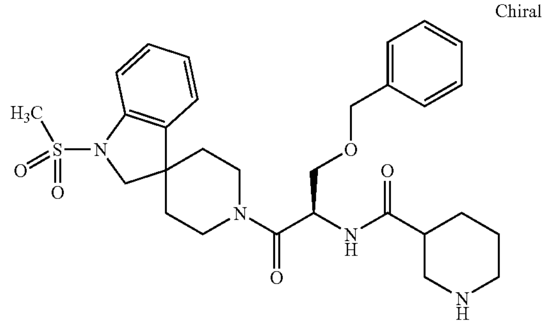 | Chiral | D |

TABLE 1-continued

Representative compounds of the invention[A, B, C, D]

| Number | Structure | | Activity |
|---|---|---|---|
| 5 | 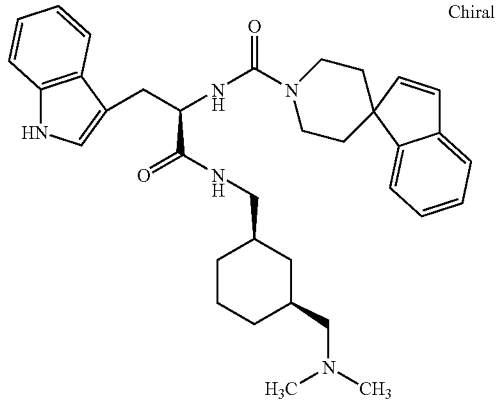 | Chiral | A |
| 6 | 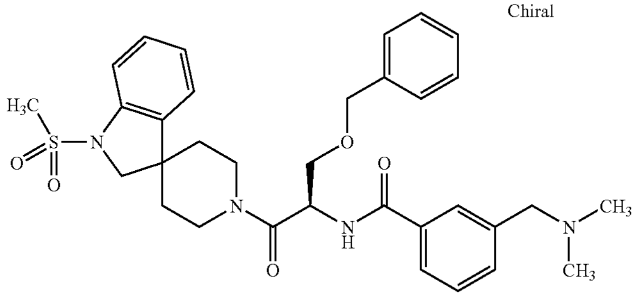 | Chiral | A |
| 7 | 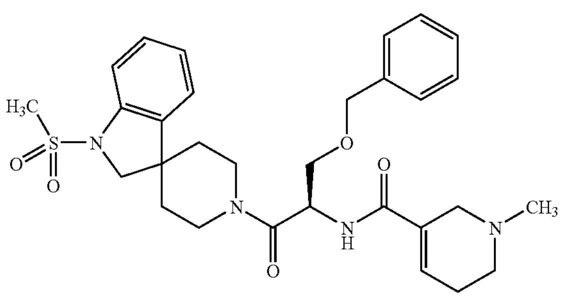 | | D |
| 8 | 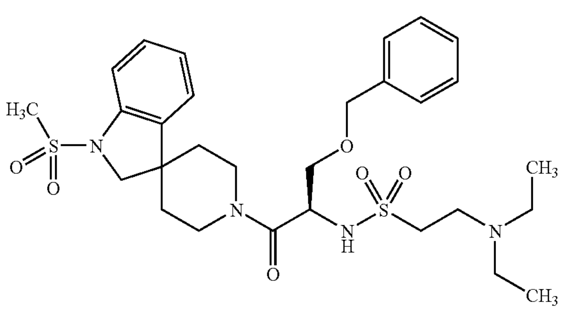 | | D |

TABLE 1-continued
Representative compounds of the invention[A, B, C, D]
| Number | Structure | Activity |
|---|---|---|
| 9 | 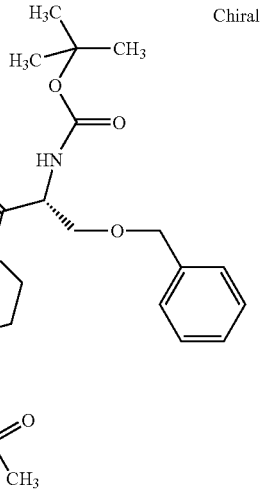 Chiral | A |
| 10 | 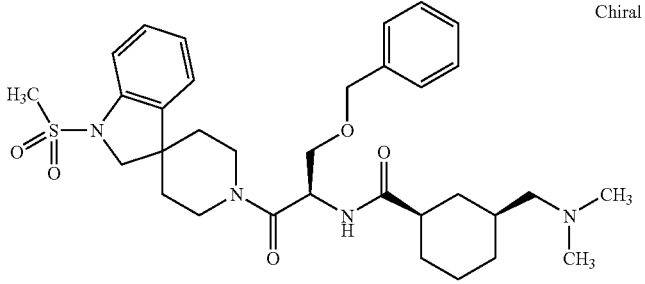 Chiral | D |
| 11 | 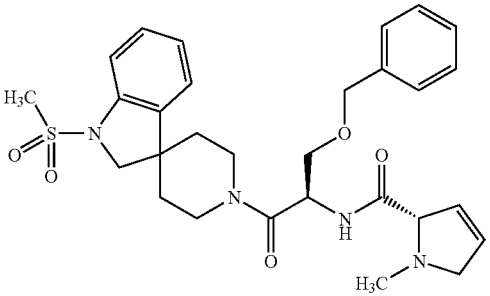 Chiral | A |
| 12 | 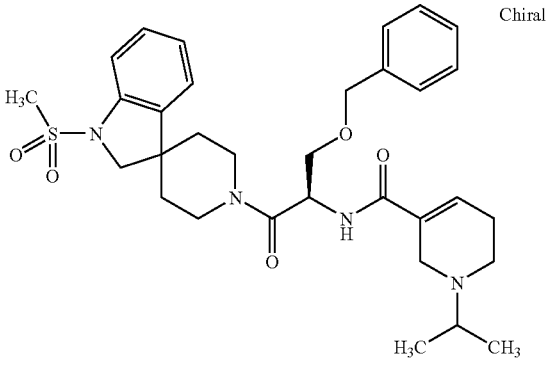 Chiral | A |

TABLE 1-continued

Representative compounds of the invention[A, B, C, D]

| Number | Structure | Activity |
|---|---|---|
| 13 | Chiral | A |
| 14 | 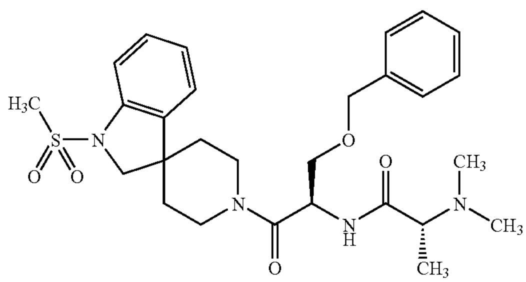 | A |
| 15 | Chiral | C |
| 16 | 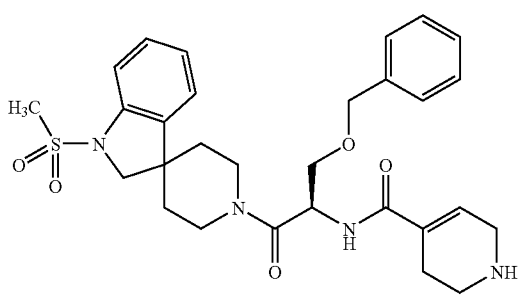 | C |
| 17 | 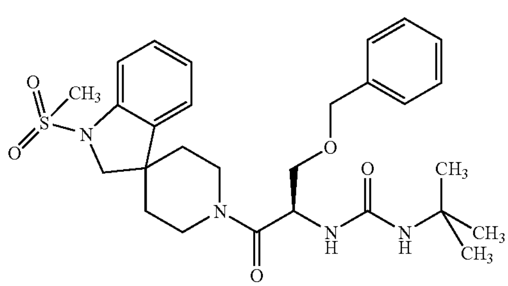 | C |

TABLE 1-continued

Representative compounds of the invention[A, B, C, D]

| Number | Structure | Activity |
|---|---|---|
| 18 | Chiral | C |
| 19 | 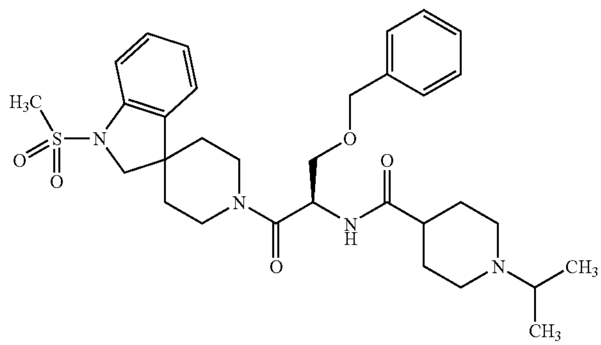 | C |
| 20 | 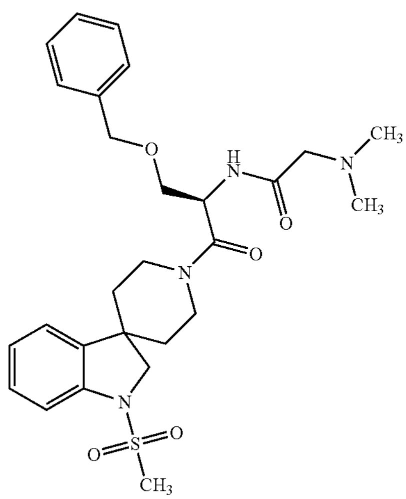 | C |
| 21 | 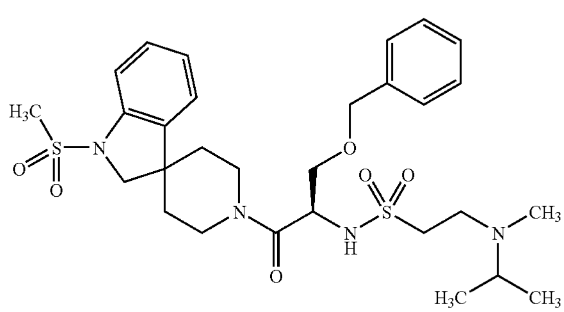 | C |

TABLE 1-continued
Representative compounds of the invention[A, B, C, D]
| Number | Structure | | Activity |
|---|---|---|---|
| 22 | 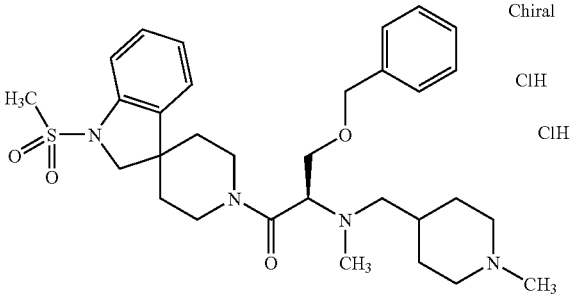 | Chiral<br><br>ClH<br><br>ClH | C |
| 23 | 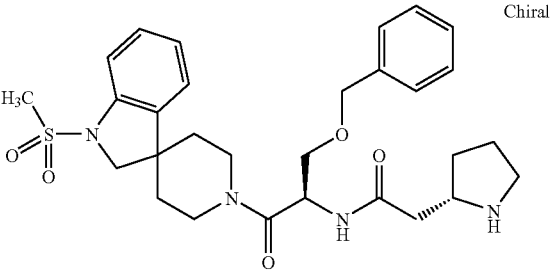 | Chiral | C |
| 24 | 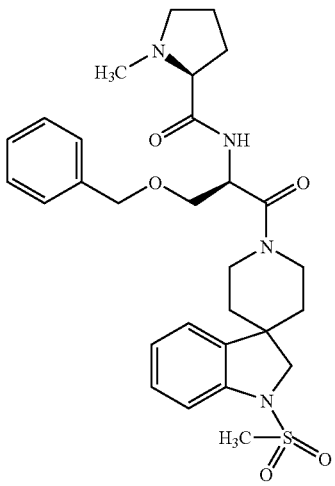 | | C |
| 25 | 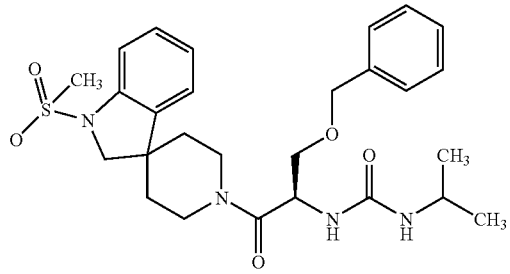 | | C |

TABLE 1-continued
Representative compounds of the invention[A, B, C, D]
| Number | Structure | Activity |
|---|---|---|
| 26 | 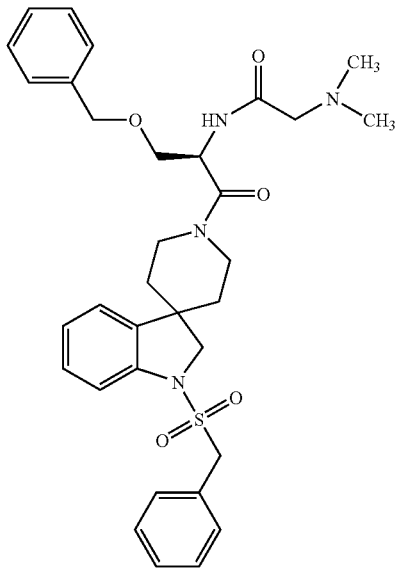 | C |
| 27 | 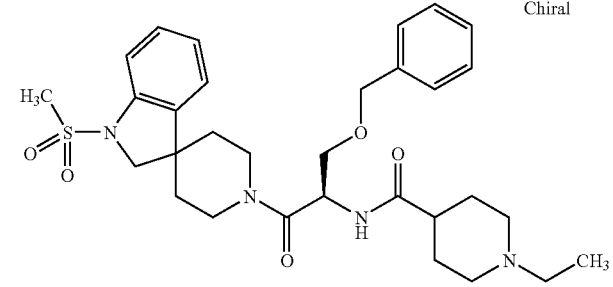 Chiral | C |
| 28 | 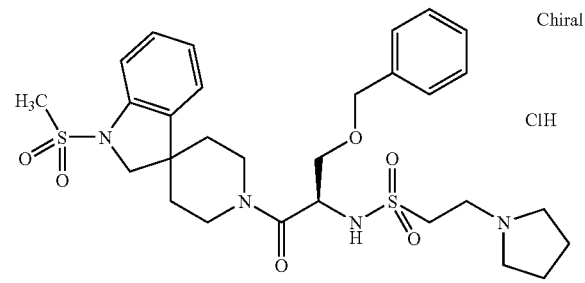 Chiral ClH | C |
| 29 | 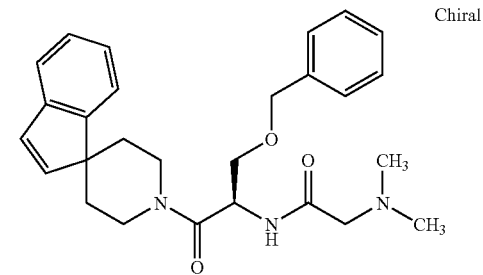 Chiral | C |

TABLE 1-continued
Representative compounds of the invention[A, B, C, D]
| Number | Structure | Activity |
|---|---|---|
| 30 | 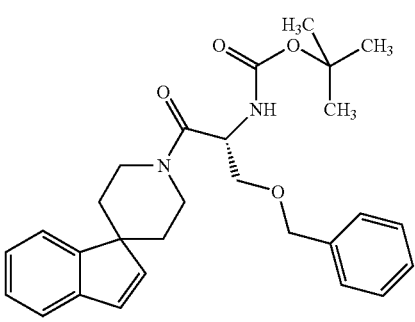 Chiral | C |
| 31 | 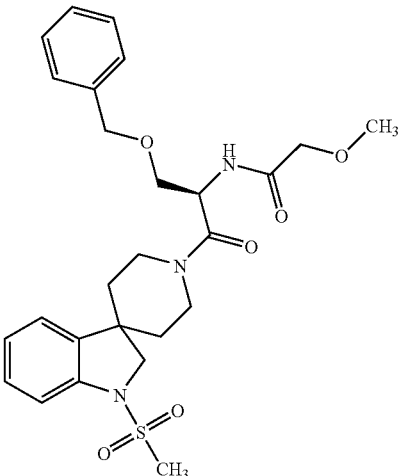 | C |
| 32 | 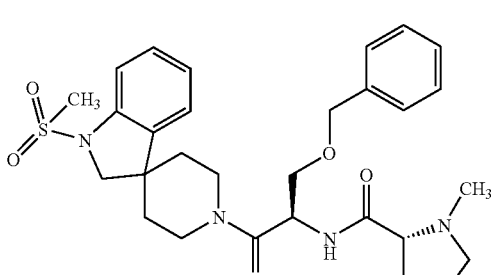 | C |
| 33 | 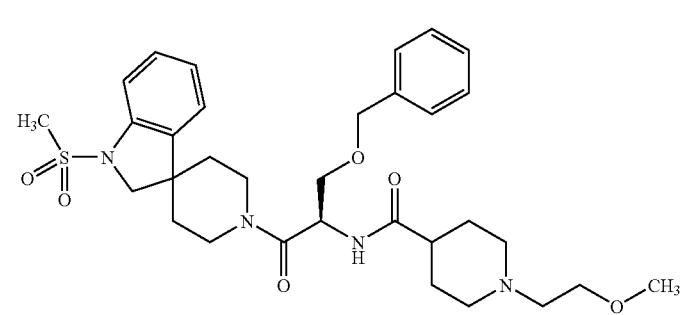 | C |

TABLE 1-continued

Representative compounds of the invention[A, B, C, D]

| Number | Structure | Activity |
|--------|-----------|----------|
| 34 | 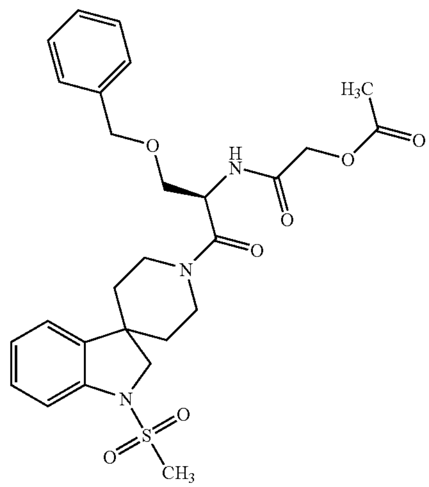 | C |
| 35 | 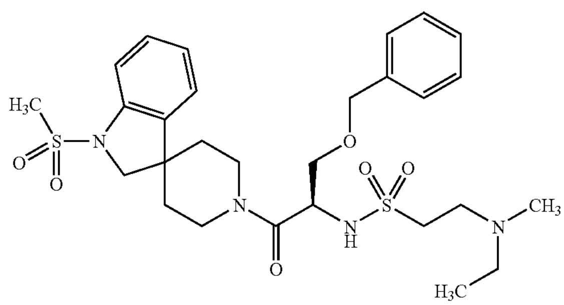 | C |
| 36 | Chiral | C |
| 37 | Chiral ClH | C |

TABLE 1-continued
Representative compounds of the invention[A, B, C, D]
| Number | Structure | Activity |
|---|---|---|
| 38 | 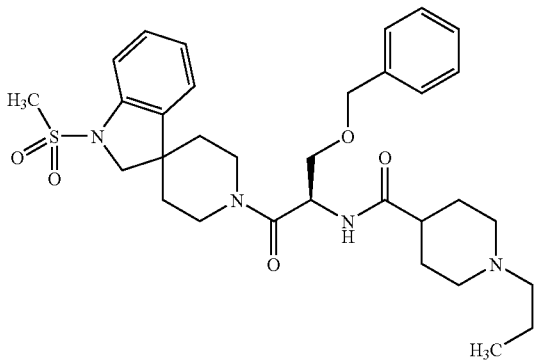 | C |
| 39 | 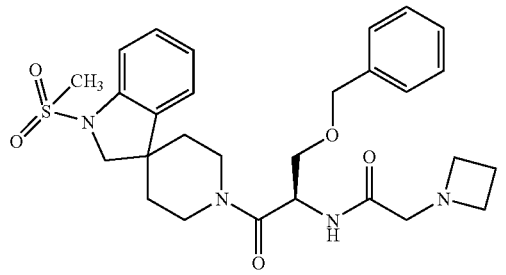 | C |
| 40 | 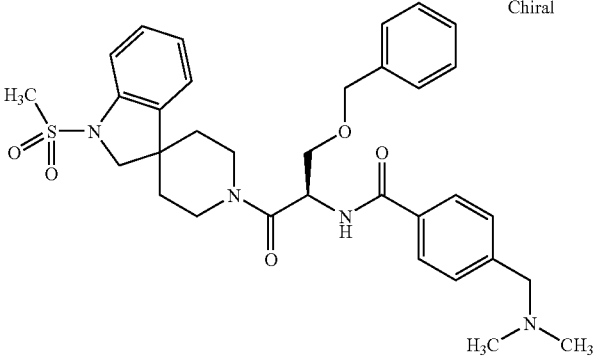 Chiral | C |
| 41 | 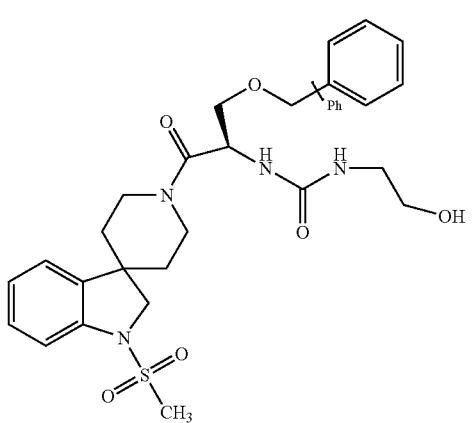 | C |

TABLE 1-continued
Representative compounds of the invention[A, B, C, D]
| Number | Structure | Activity |
|---|---|---|
| 42 | 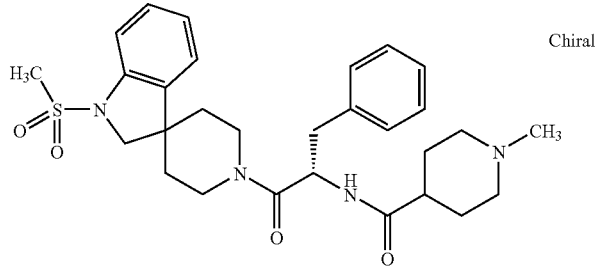 Chiral | C |
| 43 | 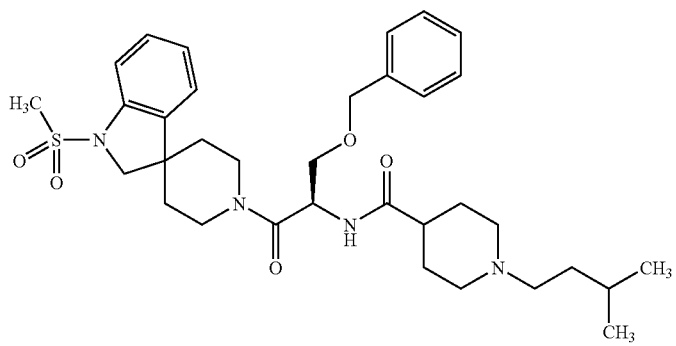 | C |
| 44 | 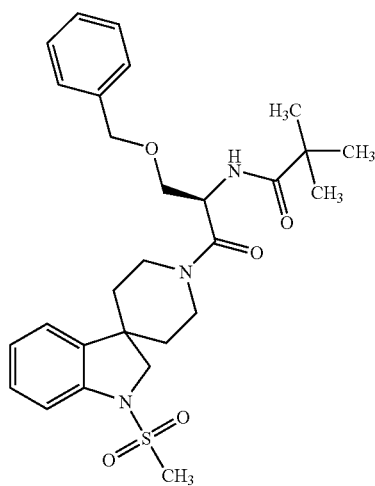 | C |
| 45 | 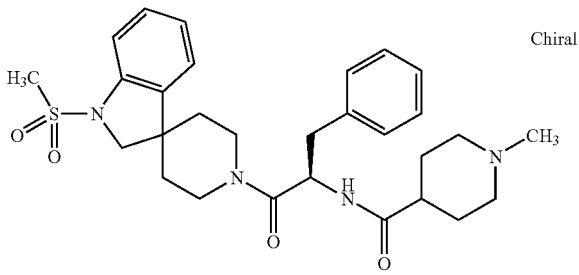 Chiral | C |

TABLE 1-continued
Representative compounds of the invention[A, B, C, D]
| Number | Structure | Activity |
|---|---|---|
| 46 | 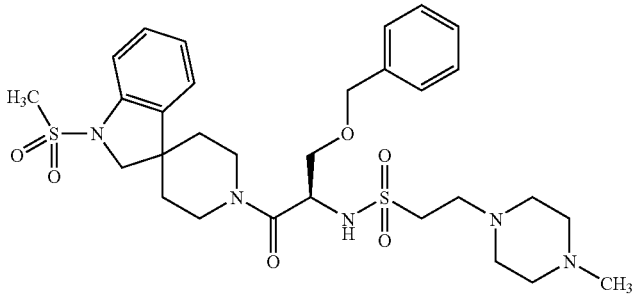 | C |
| 47 | 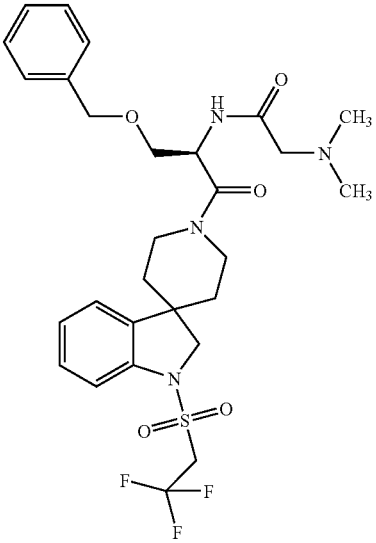 | C |
| 48 | 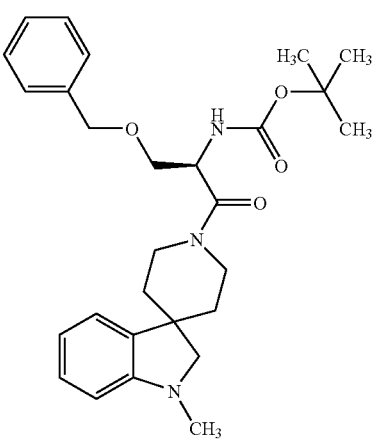 | C |

TABLE 1-continued

Representative compounds of the invention[A, B, C, D]

| Number | Structure | | Activity |
|---|---|---|---|
| 49 | 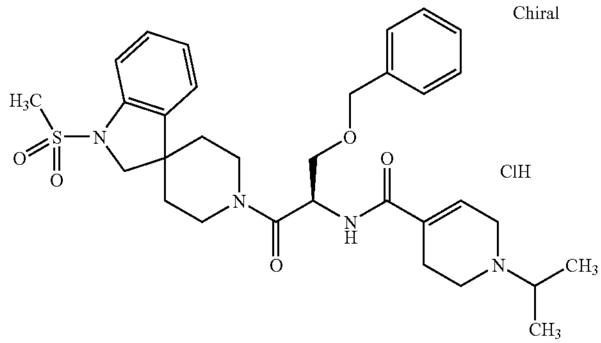 | Chiral ClH | C |
| 50 | 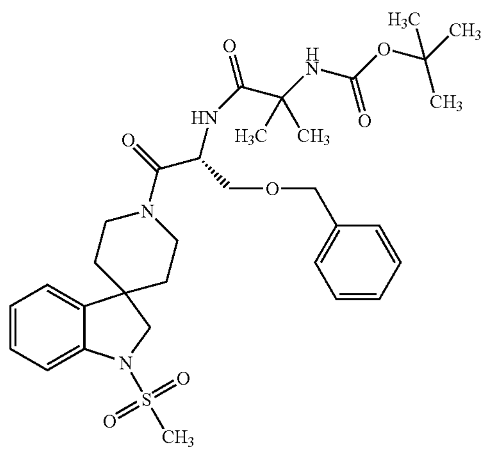 | Chiral | E |
| 51 | 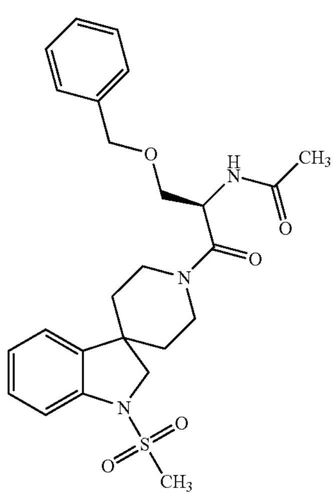 | | E |

TABLE 1-continued

Representative compounds of the invention[A, B, C, D]

| Number | Structure | Activity |
|---|---|---|
| 52 | 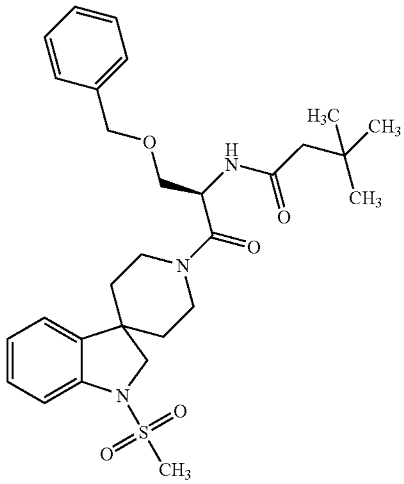 | E |
| 53 | 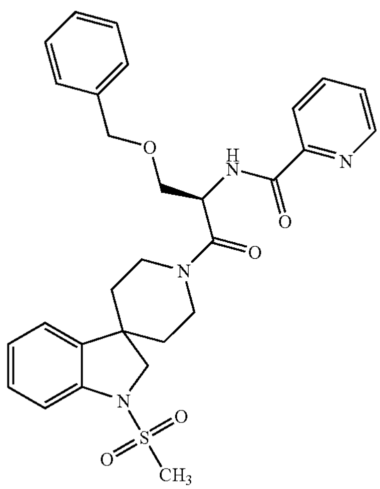 | E |
| 54 | 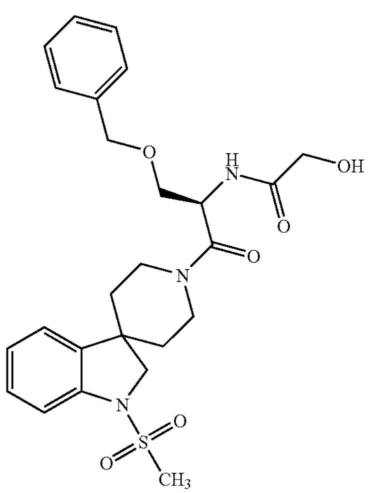 | E |

TABLE 1-continued

Representative compounds of the invention[A, B, C, D]

| Number | Structure | Activity |
|---|---|---|
| 55 | 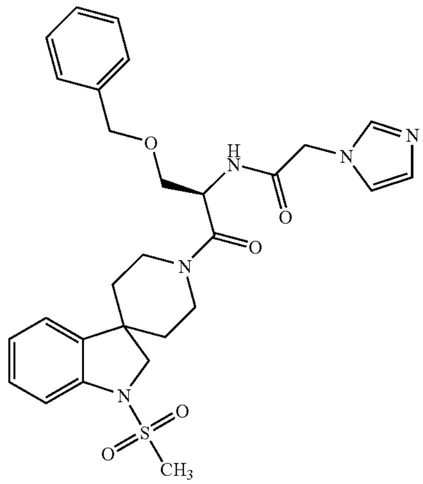 | E |
| 56 | 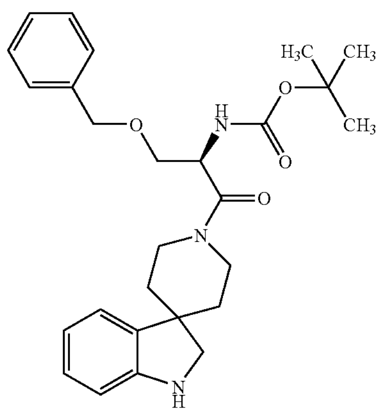 | E |
| 57 | 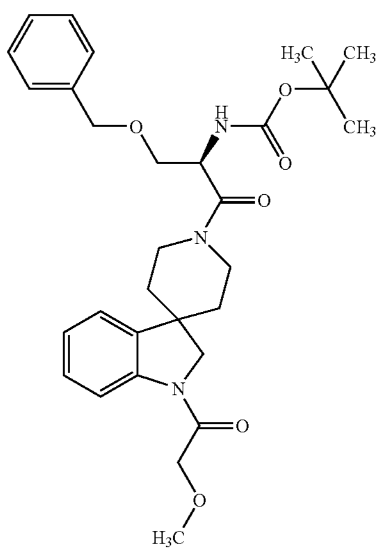 | E |

TABLE 1-continued
Representative compounds of the invention[A, B, C, D]
| Number | Structure | Activity |
|---|---|---|
| 58 | 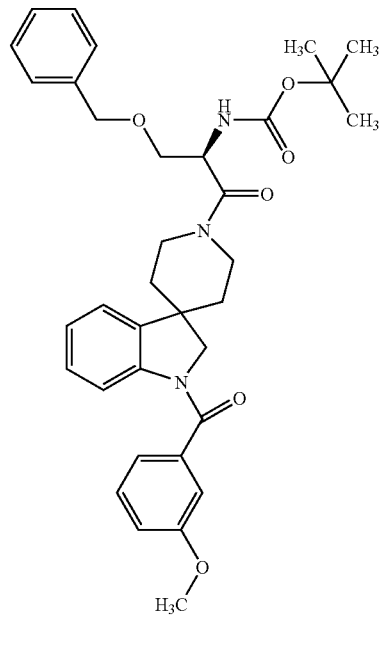 | E |
| 59 | 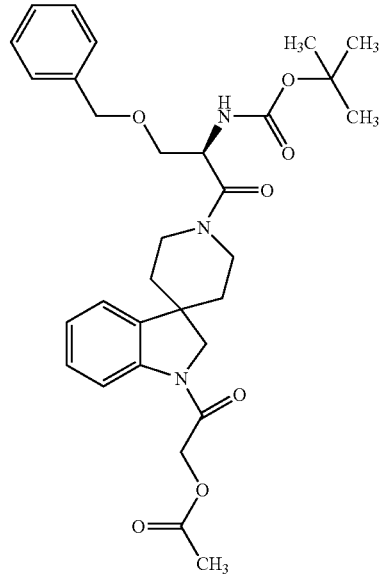 | E |

TABLE 1-continued
Representative compounds of the invention[A, B, C, D]
| Number | Structure | Activity |
|--------|-----------|----------|
| 60 | 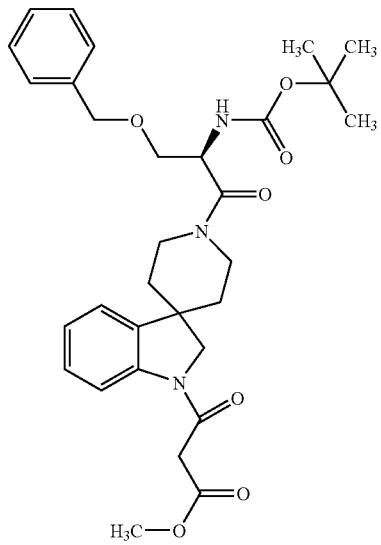 | E |
| 61 | 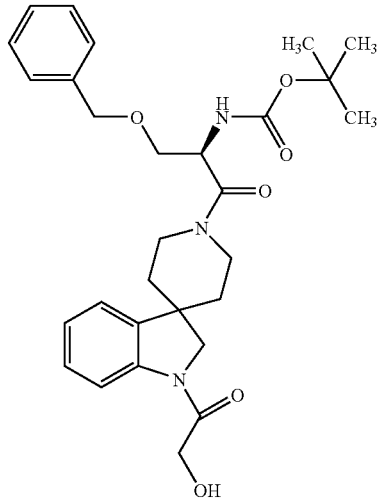 | E |

TABLE 1-continued

Representative compounds of the invention[A, B, C, D]

| Number | Structure | Activity |
|---|---|---|
| 62 | 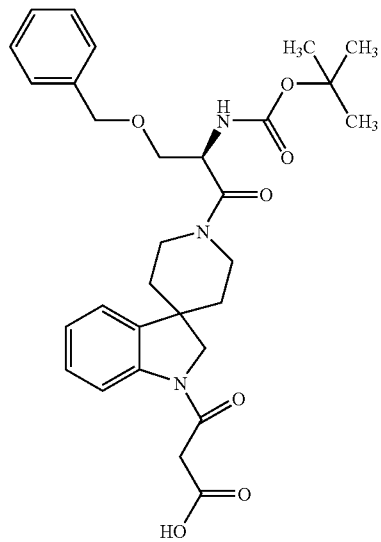 | E |
| 63 | 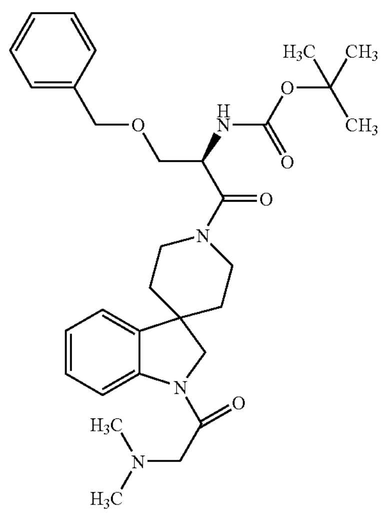 | E |
| 64 | 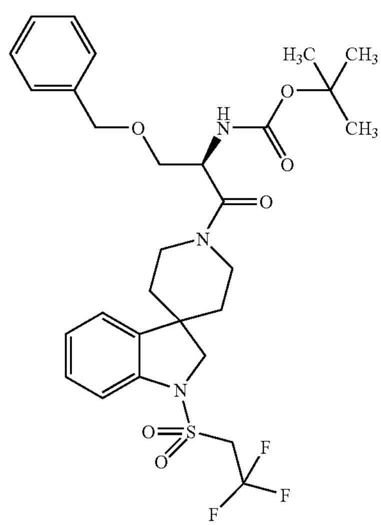 | E |

TABLE 1-continued
Representative compounds of the invention[A, B, C, D]
| Number | Structure | Activity |
|---|---|---|
| 65 | 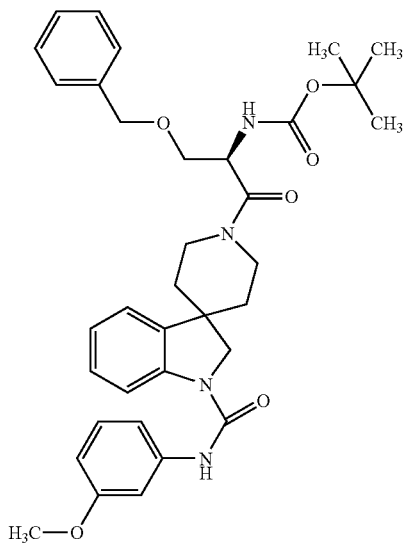 | E |
| 66 | 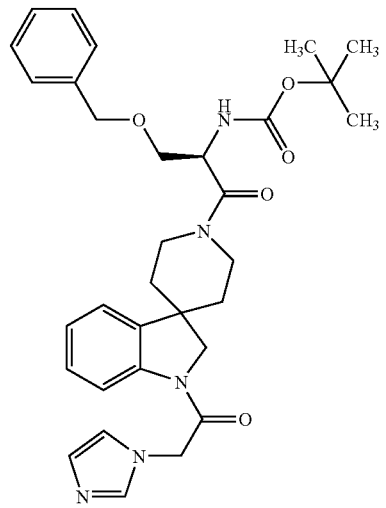 | E |

TABLE 1-continued
Representative compounds of the invention[A, B, C, D]
| Number | Structure | Activity |
|---|---|---|
| 67 | 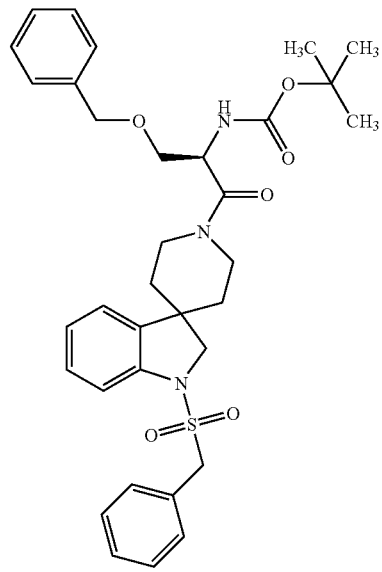 | E |
| 68 | 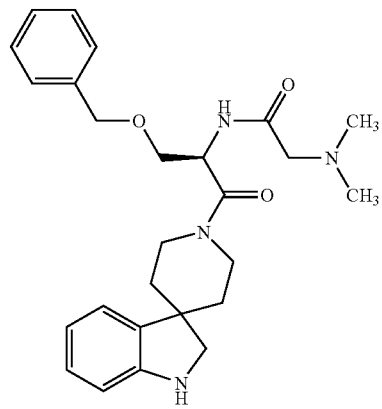 | E |

TABLE 1-continued
Representative compounds of the invention[A, B, C, D]
| Number | Structure | Activity |
|---|---|---|
| 69 | 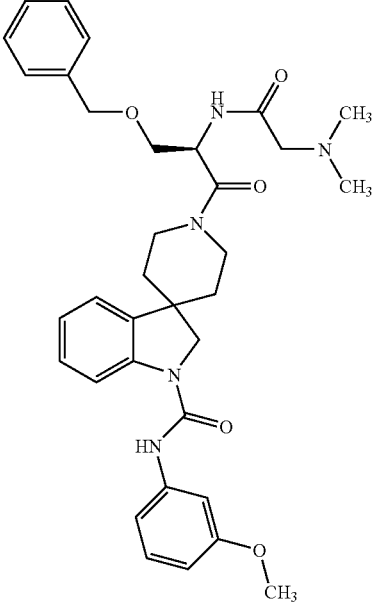 | E |
| 70 | 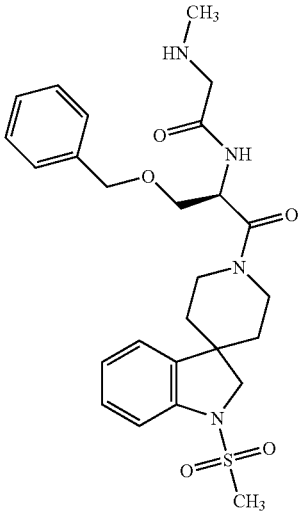 | E |

TABLE 1-continued
Representative compounds of the invention[A, B, C, D]
| Number | Structure | Activity |
|---|---|---|
| 71 | 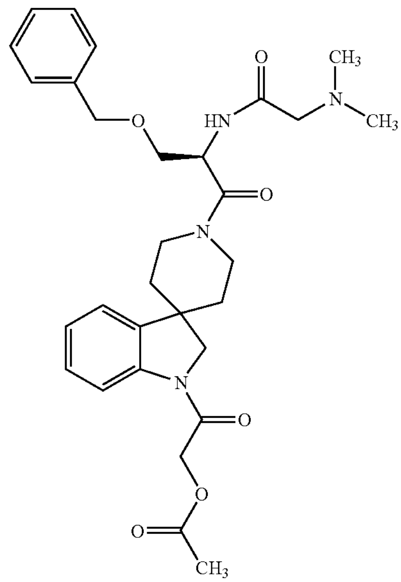 | E |
| 72 | 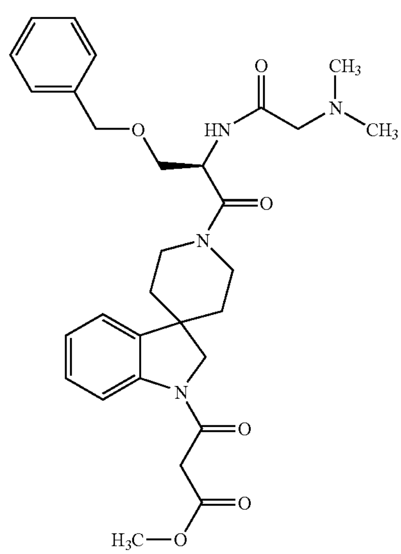 | E |
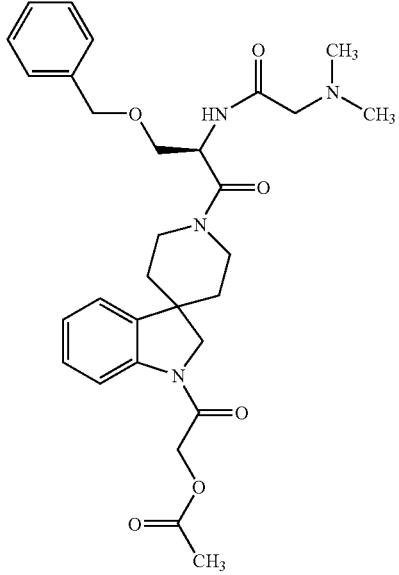

TABLE 1-continued
Representative compounds of the invention[A, B, C, D]
| Number | Structure | Activity |
|---|---|---|
| 73 | 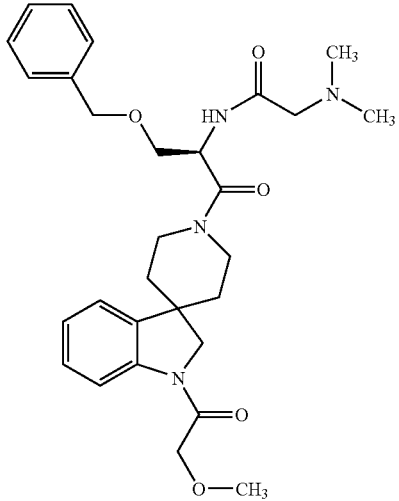 | E |
| 74 | 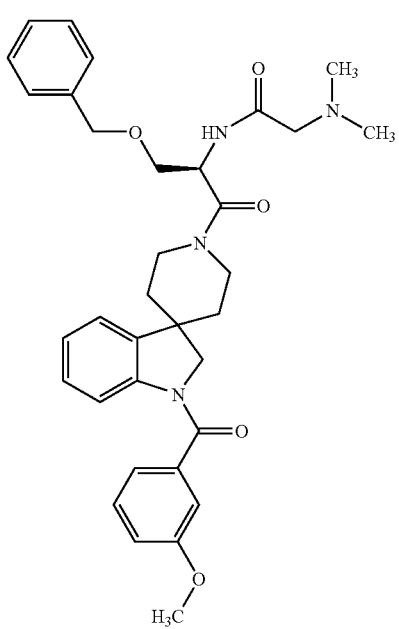 | E |

TABLE 1-continued

Representative compounds of the invention[A, B, C, D]

| Number | Structure | Activity |
|---|---|---|
| 75 | 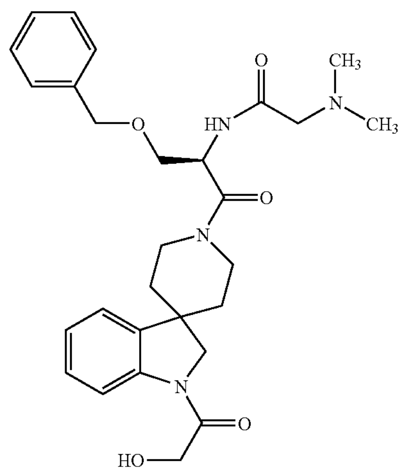 | E |
| 76 | 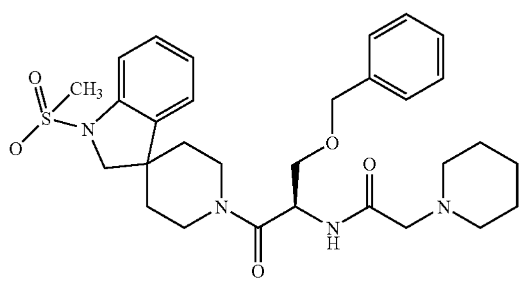 | E |
| 77 | 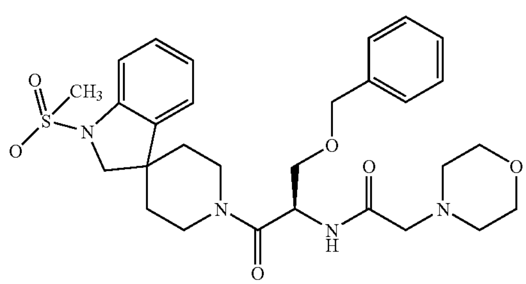 | E |
| 78 | 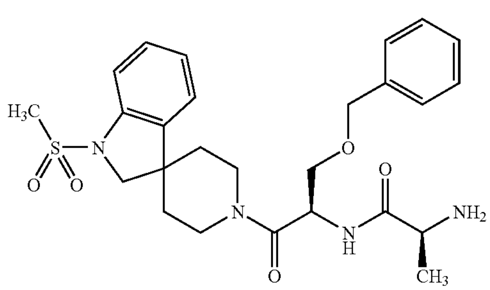 | E |

TABLE 1-continued

Representative compounds of the invention[A, B, C, D]

| Number | Structure | Activity |
|---|---|---|
| 79 | 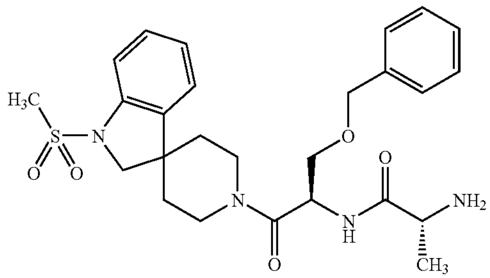 | E |
| 80 | 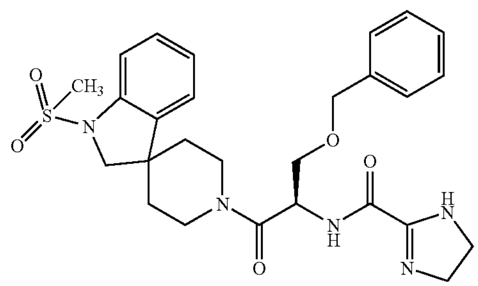 | E |
| 81 | 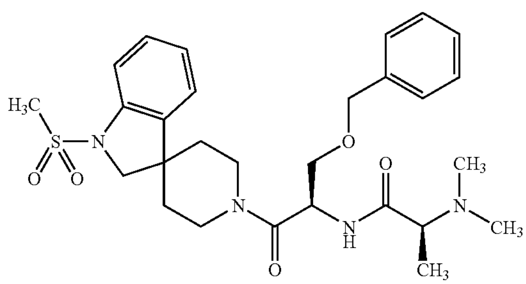 | E |
| 82 | 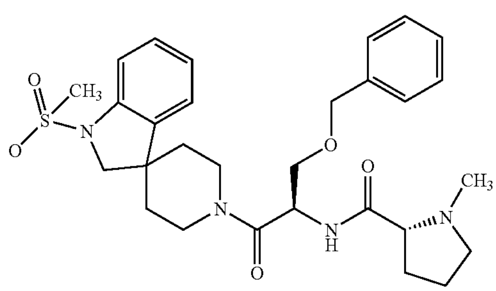 | E |
| 83 | 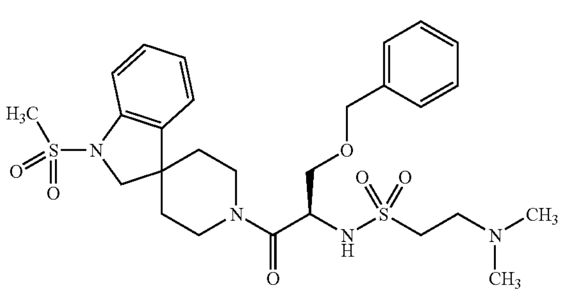 | E |

TABLE 1-continued

Representative compounds of the invention[A, B, C, D]

| Number | Structure | Activity |
|---|---|---|
| 84 | 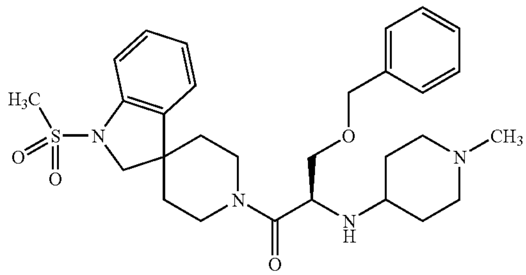 | E |
| 85 | 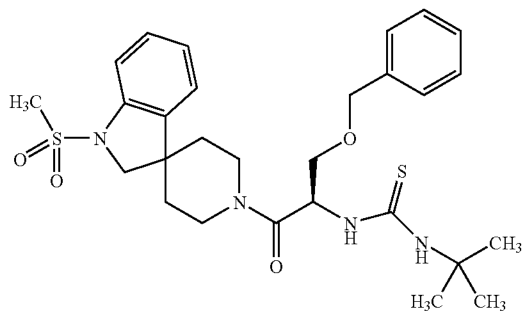 | E |
| 86 | 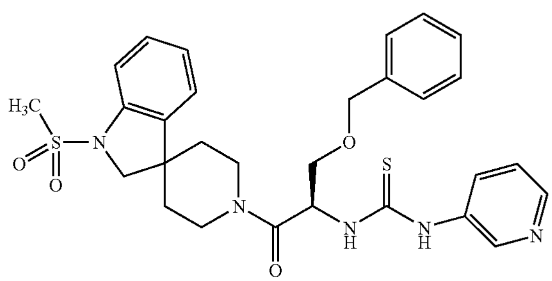 | E |
| 87 | 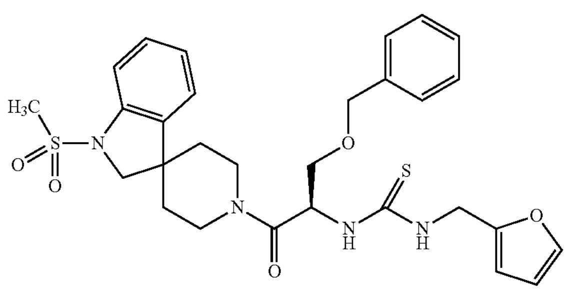 | E |
| 88 | 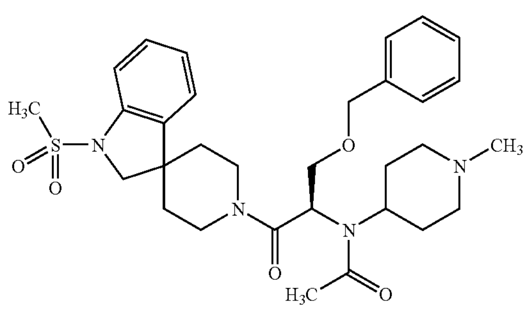 | E |

TABLE 1-continued

Representative compounds of the invention[A, B, C, D]

| Number | Structure | Activity |
|---|---|---|
| 89 | 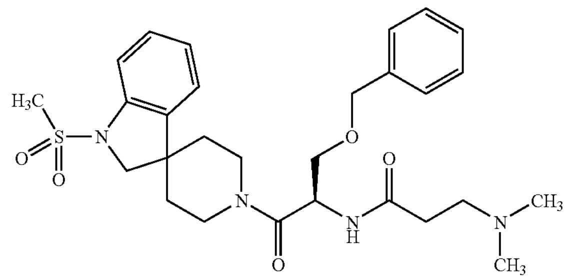 | E |
| 90 | 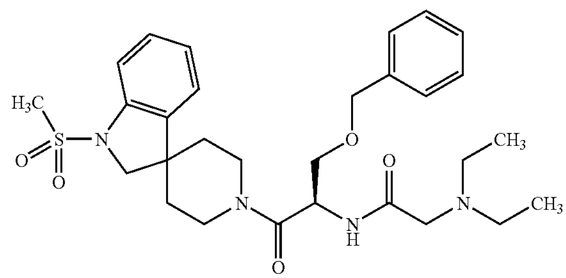 | E |
| 91 | 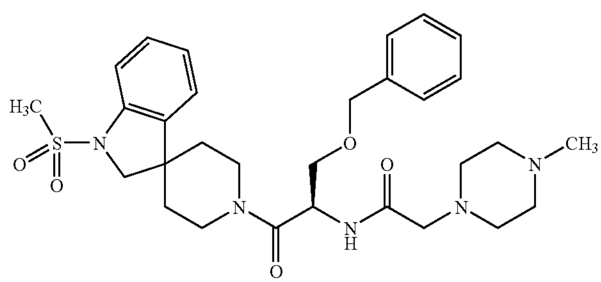 | E |
| 92 | 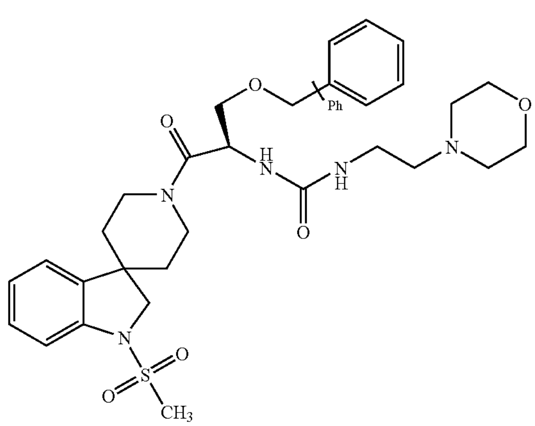 | E |

TABLE 1-continued
Representative compounds of the invention[A, B, C, D]
| Number | Structure | Activity |
|---|---|---|
| 93 | 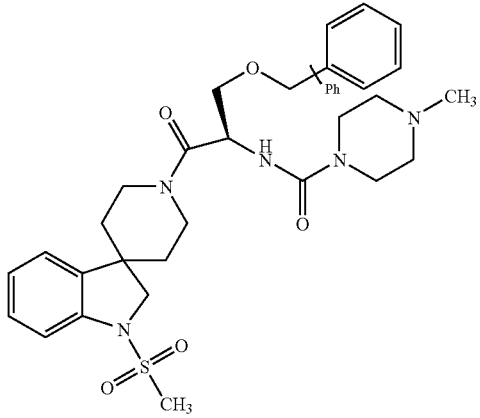 | E |
| 94 | 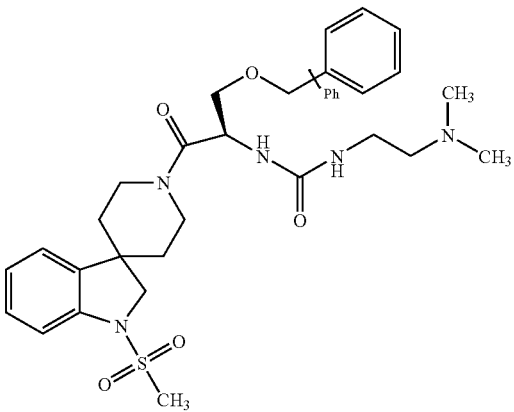 | E |
| 95 | 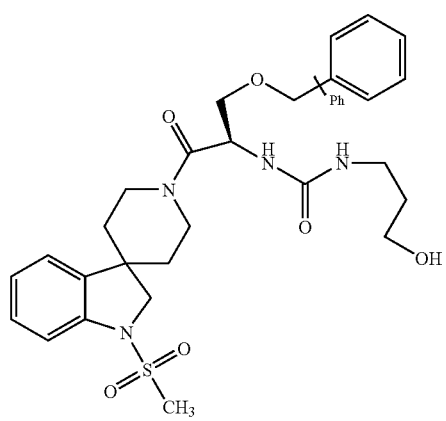 | E |

TABLE 1-continued

Representative compounds of the invention[A, B, C, D]

| Number | Structure | Activity |
|---|---|---|
| 96 | 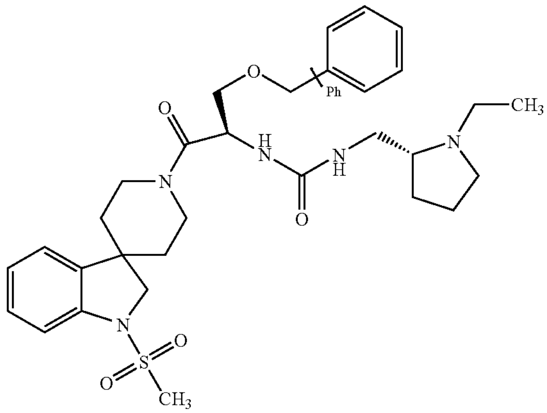 | E |
| 97 | 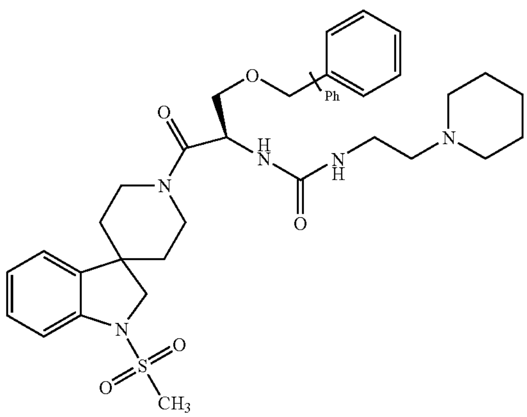 | E |
| 98 | 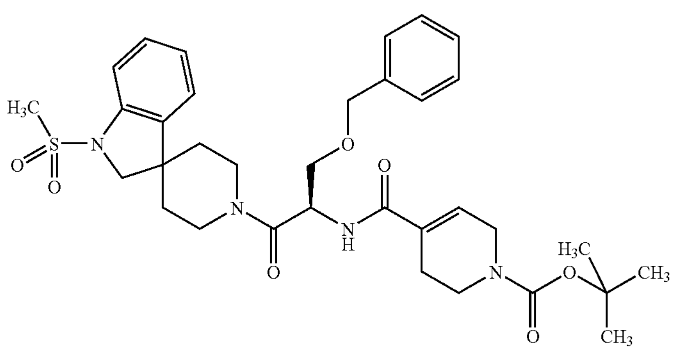 | E |
| 99 | 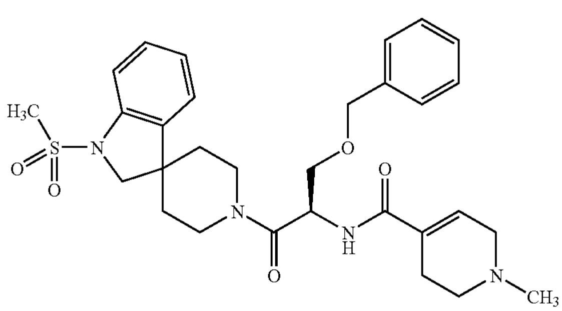 | E |

TABLE 1-continued
Representative compounds of the invention[A, B, C, D]
| Number | Structure | Activity |
|---|---|---|
| 100 | 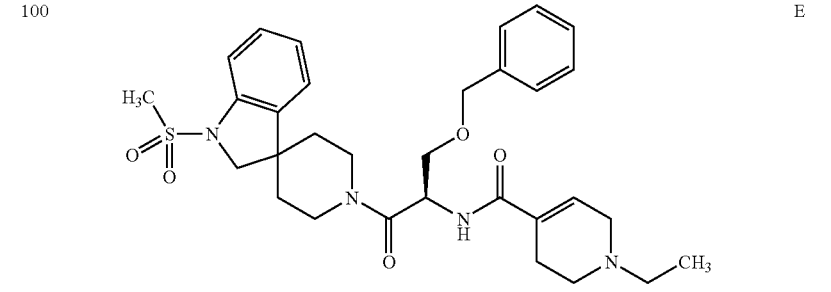 | E |
| 101 | 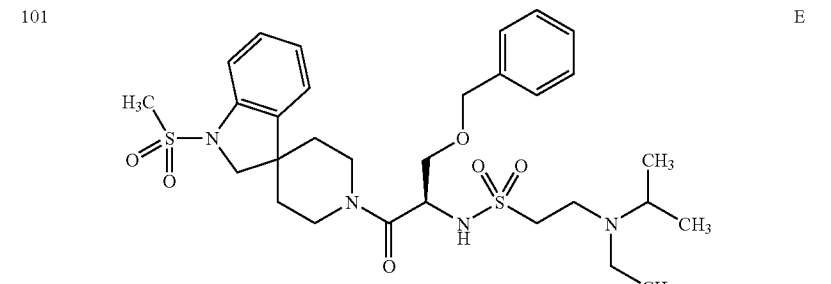 | E |
| 102 | 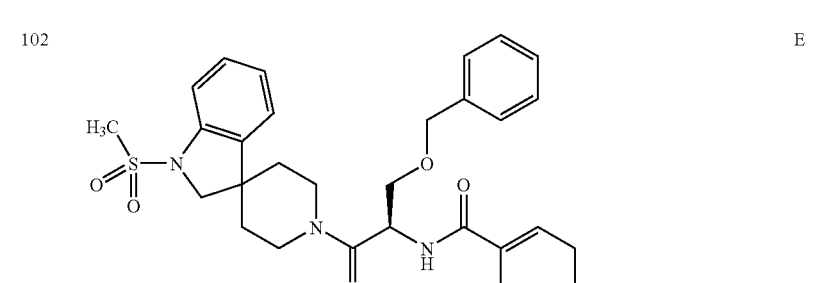 | E |
| 103 | 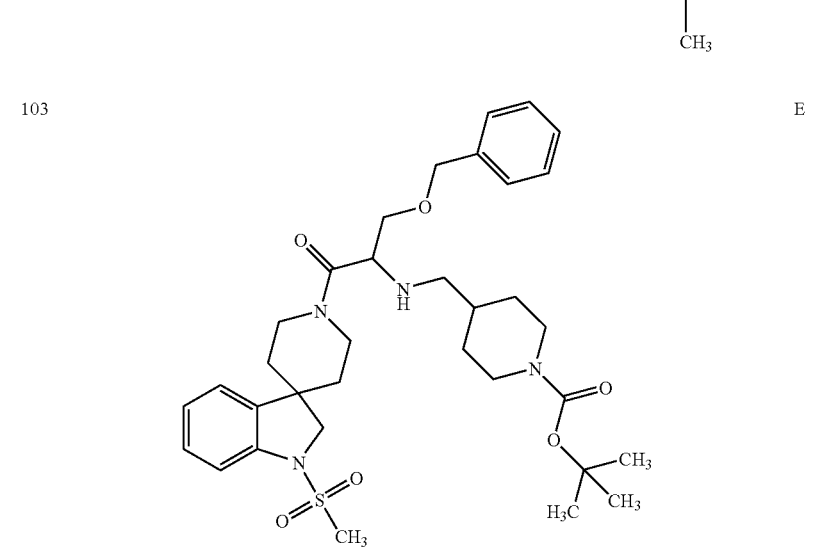 | E |

TABLE 1-continued

Representative compounds of the invention[A, B, C, D]

| Number | Structure | Activity |
|---|---|---|
| 104 | 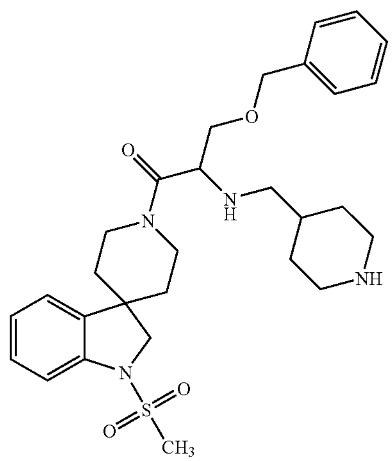 | E |
| 105 | Chiral | E |
| 106 | Chiral | E |
| 107 | Chiral | E |

TABLE 1-continued

Representative compounds of the invention[A, B, C, D]

| Number | Structure | | Activity |
|---|---|---|---|
| 108 | 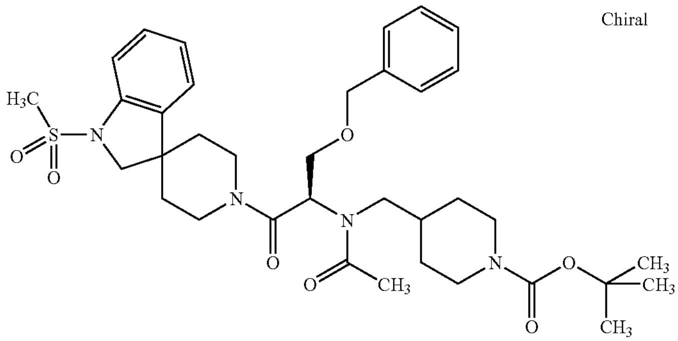 | Chiral | E |
| 109 | 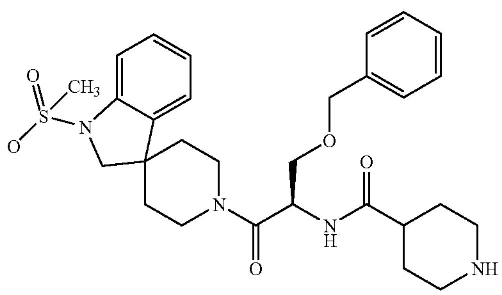 | | E |
| 110 | 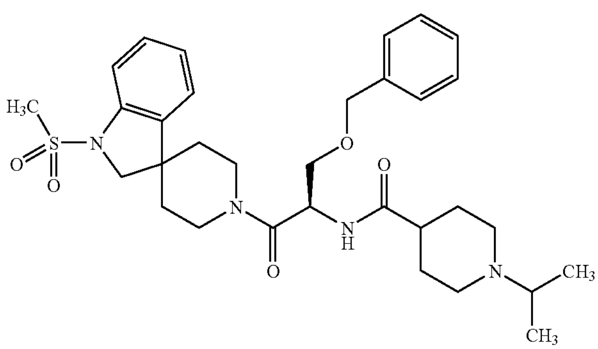 | | E |
| 111 | 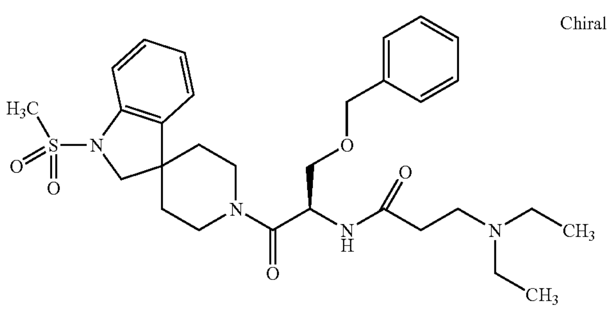 | Chiral | E |

TABLE 1-continued

Representative compounds of the invention[A, B, C, D]

| Number | Structure | Activity |
|---|---|---|
| 112 | Chiral | E |
| 113 | Chiral | E |
| 114 | Chiral | E |
| 115 | Chiral | E |

TABLE 1-continued

Representative compounds of the invention[A, B, C, D]

| Number | Structure | Activity |
|---|---|---|
| 116 | Chiral | E |
| 117 | Chiral | E |
| 118 | Chiral | E |
| 119 | Chiral | E |
| 120 | Chiral | E |

TABLE 1-continued

Representative compounds of the invention[A, B, C, D]

| Number | Structure | Activity |
|---|---|---|
| 121 | Chiral | E |
| 122 | Chiral | E |
| 123 | Chiral | E |
| 124 | Chiral | E |

TABLE 1-continued
Representative compounds of the invention[A, B, C, D]
| Number | Structure | | Activity |
|---|---|---|---|
| 125 | 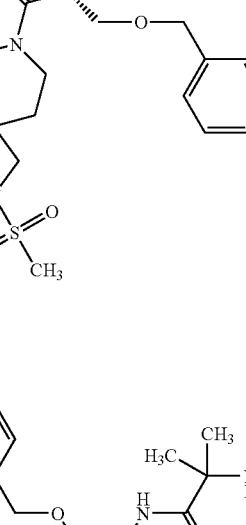 | Chiral | B |
| 126 | 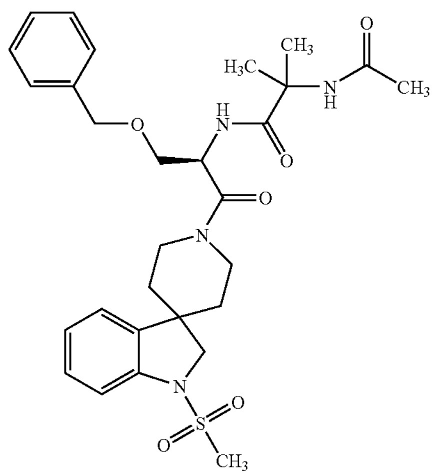 | Chiral | B |
| 127 | 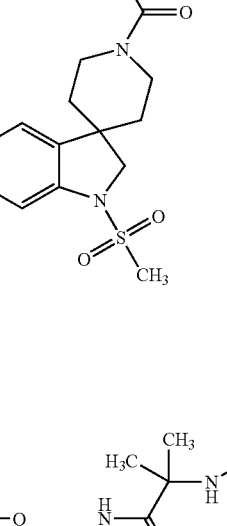 | Chiral | B |

TABLE 1-continued

Representative compounds of the invention[A, B, C, D]

| Number | Structure | Activity |
|---|---|---|
| 128 | 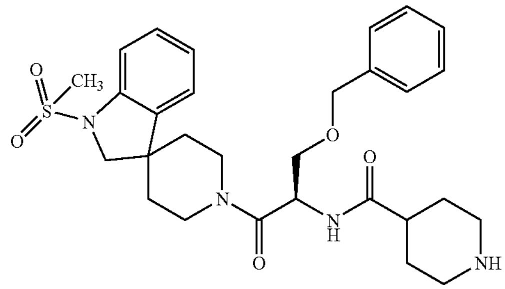 | B |
| 129 | 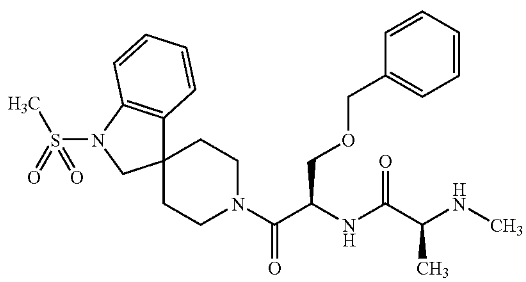 | B |
| 130 | 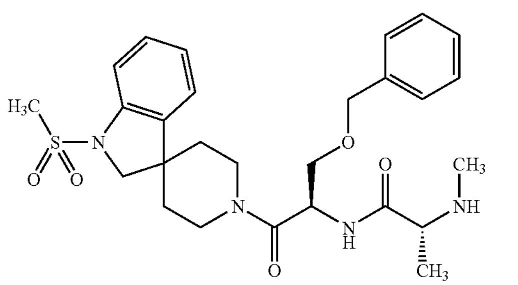 | B |
| 131 | 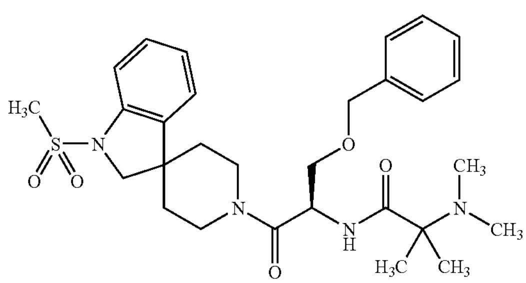 | B |
| 132 | 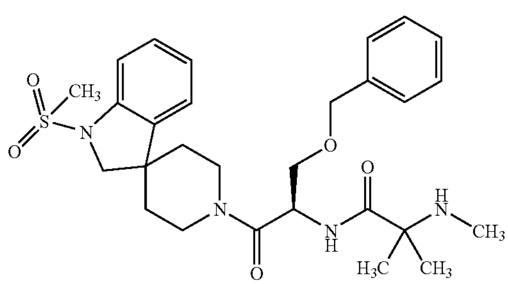 | B |

TABLE 1-continued

Representative compounds of the invention[A, B, C, D]

| Number | Structure | | Activity |
|---|---|---|---|
| 133 | 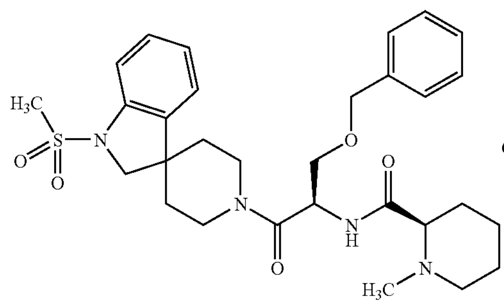 | Chiral ClH | B |
| 134 | 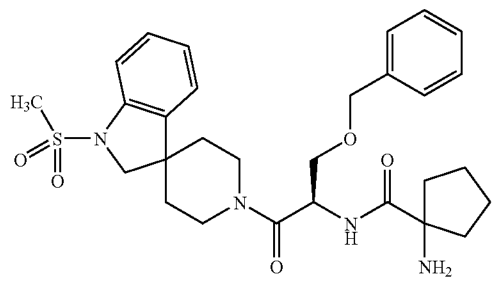 | Chiral | B |
| 135 | 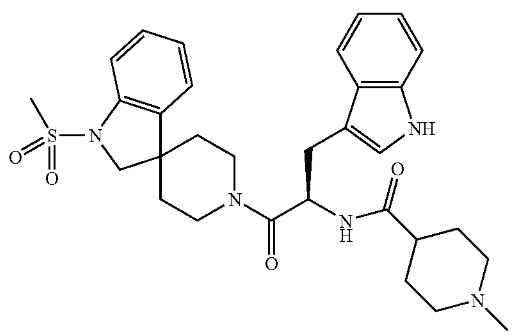 | | E |
| 136 | 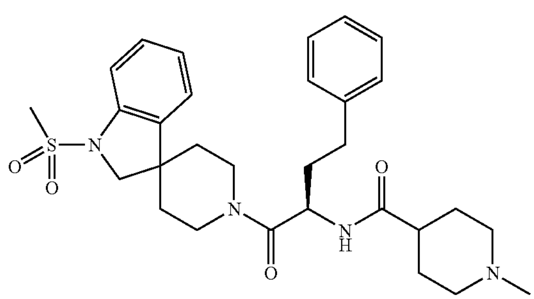 | | E |
| 137 | 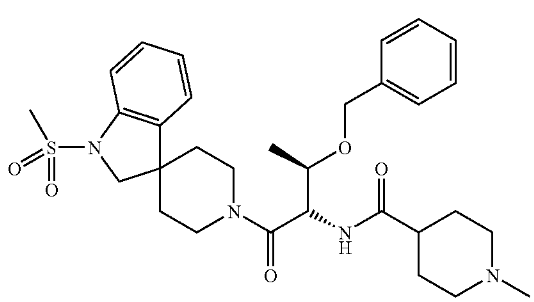 | | E |

TABLE 1-continued

Representative compounds of the invention[A, B, C, D]

| Number | Structure | Activity |
|--------|-----------|----------|
| 138 | 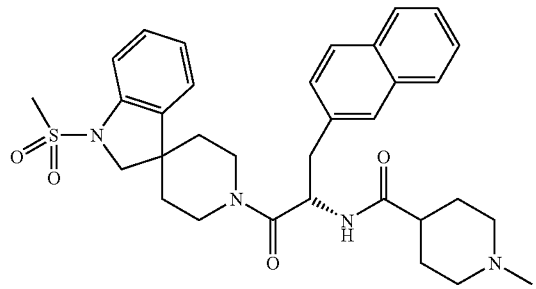 | E |
| 139 | 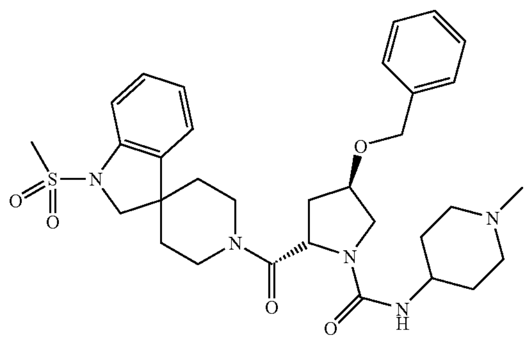 | E |
| 140 | 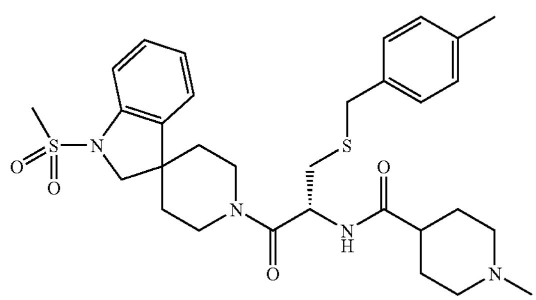 | E |
| 141 | 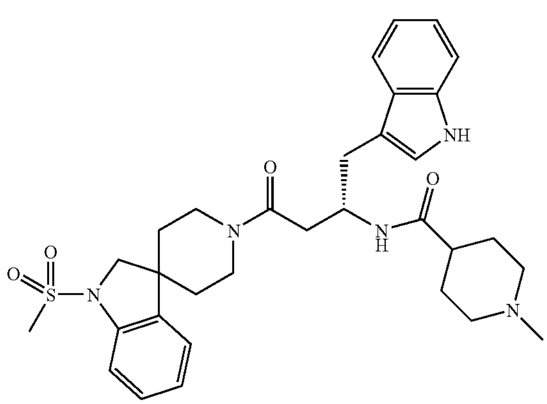 | E |

TABLE 1-continued

Representative compounds of the invention[A, B, C, D]

| Number | Structure | Activity |
|---|---|---|
| 142 | 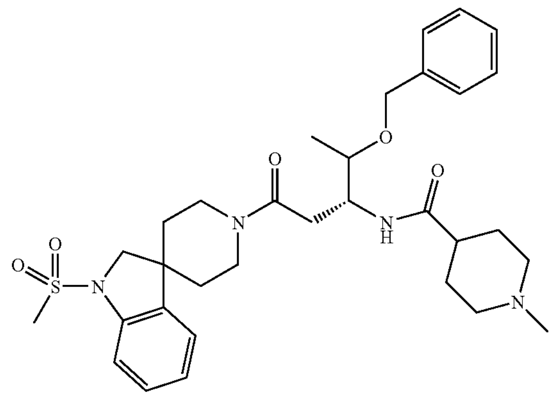 | E |
| 143 | 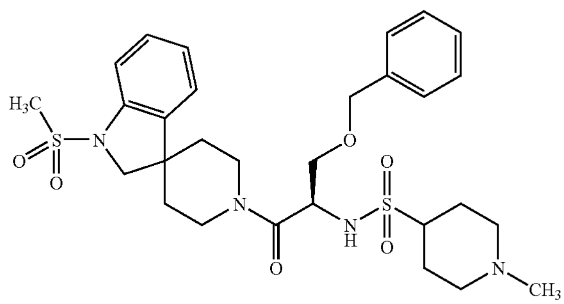 | A |
| 144 | 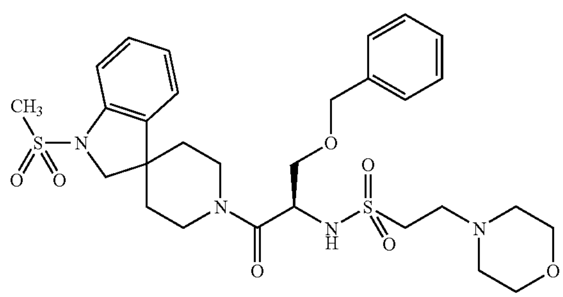 | E |
| 145 | 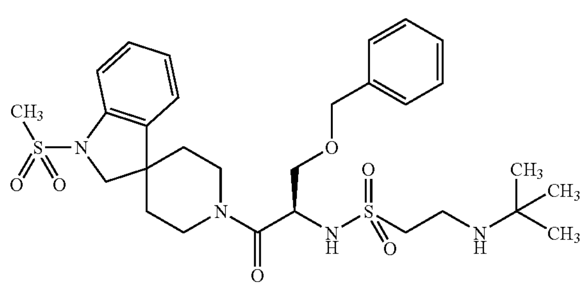 | E |

TABLE 1-continued

Representative compounds of the invention[A, B, C, D]

| Number | Structure | Activity |
|---|---|---|
| 146 | 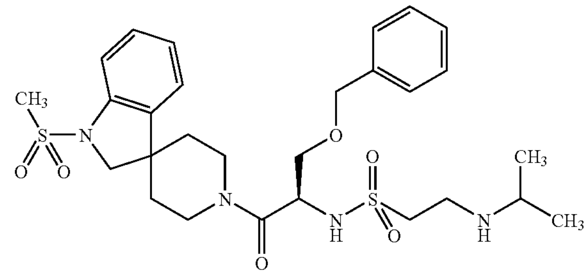 | C |
| 147 | 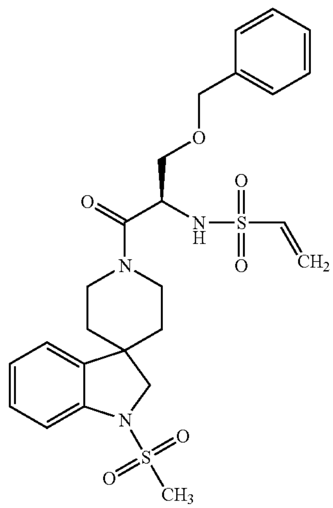 | E |
| 148 | 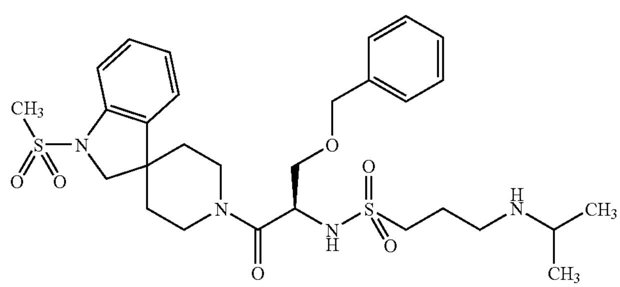 | A |
| 149 | 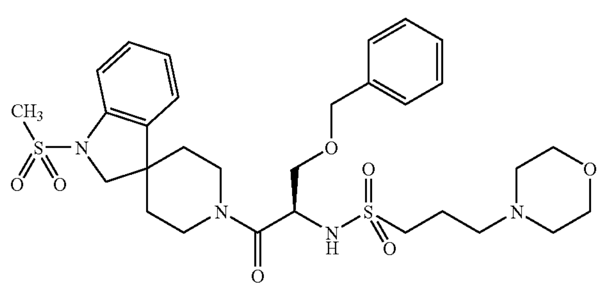 | E |

TABLE 1-continued

Representative compounds of the invention[A, B, C, D]

| Number | Structure | Activity |
|---|---|---|
| 150 | 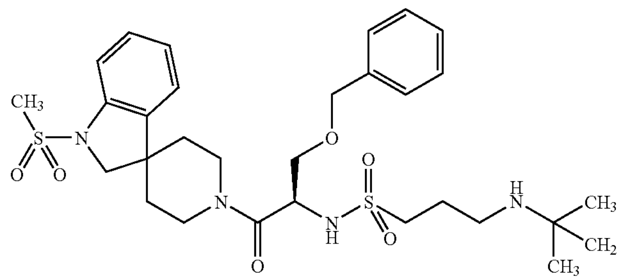 | A |
| 151 | 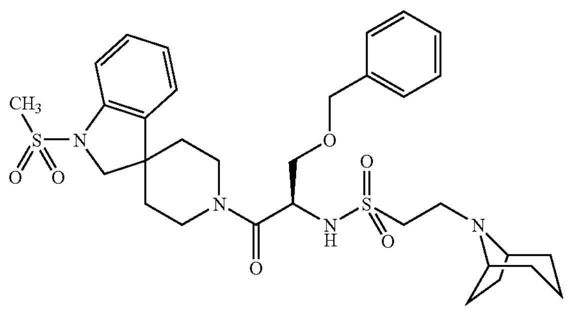 | C |
| 152 | 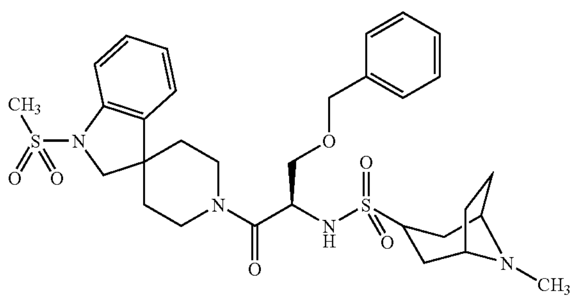 | C |
| 153 | 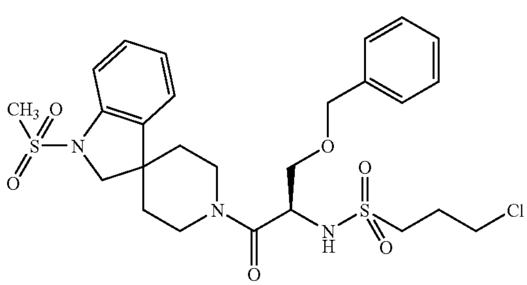 | A |
| 154 | 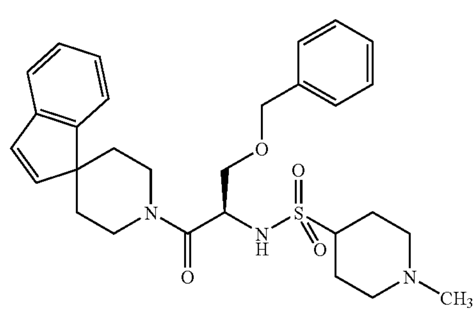 | C |

TABLE 1-continued

Representative compounds of the invention[A, B, C, D]

| Number | Structure | Activity |
|---|---|---|
| 155 | 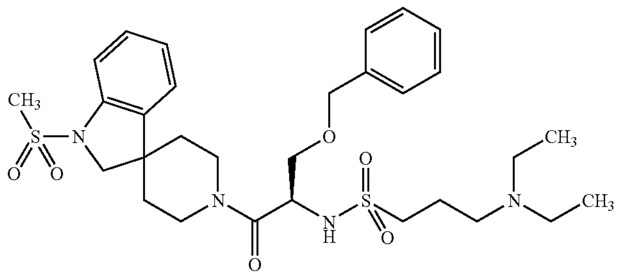 | A |
| 156 | 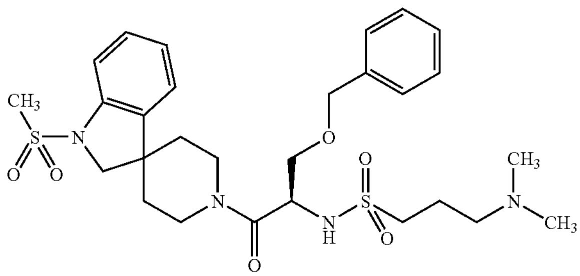 | E |
| 157 | 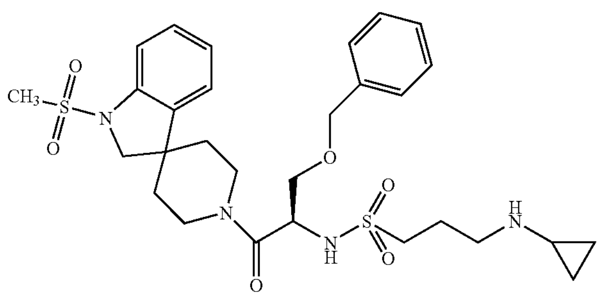 | E |
| 158 | 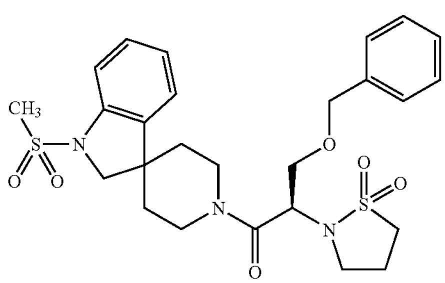 | E |
| 159 | 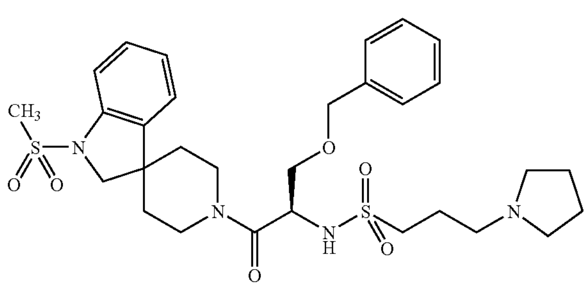 | A |

TABLE 1-continued

Representative compounds of the invention[A, B, C, D]

| Number | Structure | Activity |
|---|---|---|
| 160 | 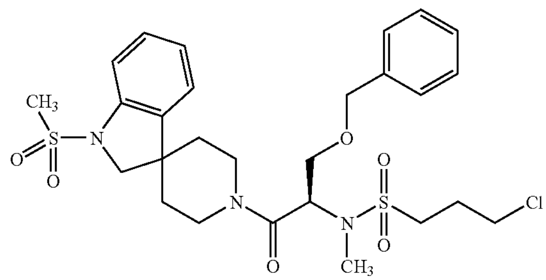 | E |
| 161 | 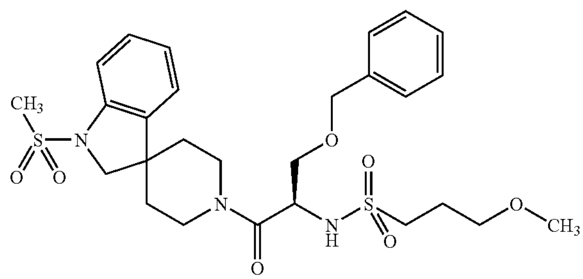 | E |
| 162 | 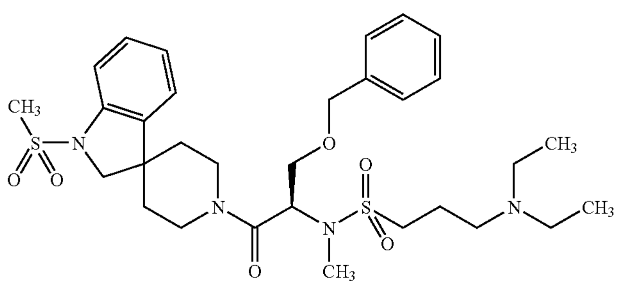 | A |
| 163 | 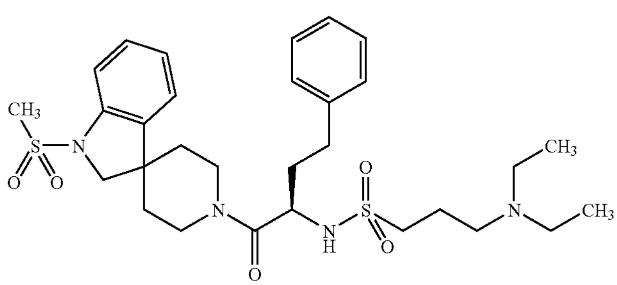 | A |
| 164 | 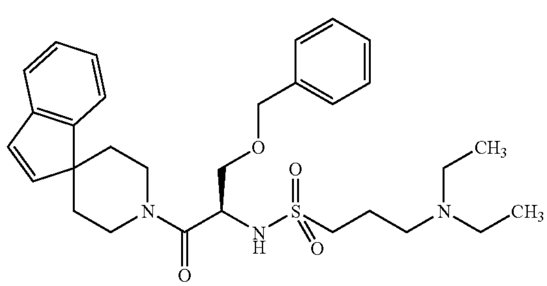 | A |

A refers to a compound having antagonist activity with $K_i$<100 nM in a cell based assay.

B refers to a compound having agonist activity with $EC_{50}$<100 nM in a cell based assay.

C refers to a compound having antagonist activity of $K_i$>100 nM and <1500 nM in a cell based assay.

D refers to a compound having antagonist activity with $K_i$, <100 nM and agonist activity with $EC_{50}$<100 nM in a cell-based assay.

E refers to other exemplary compounds.

Other aspects of this invention relate to a composition having a compound of any of the formulae described herein and a pharmaceutically acceptable carrier; or a compound of any of the formulae described herein, an additional therapeutic compound (e.g., an anti-hypertensive compound or a cholesterol lowering compound), and a pharmaceutically acceptable carrier; or a compound of any of the formulae described herein, an additional therapeutic compound, and a pharmaceutically acceptable carrier.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Synthesis of Ghrelin Receptor-Modulating Compounds

Compounds of formula (X), a subset of formula (I), are prepared by treating the compound of formulae (VI) and (VII) with trifluoroacetic acid followed by sodium borohydride to provide the compound of formula (VIII). (Variables for all formulae are as defined herein, e.g., as defined in formula (I).)

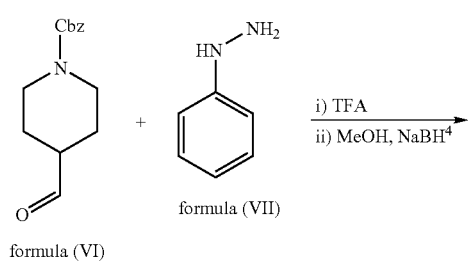

formula (VI)    formula (VII)

formula (VIII)

The compound of formula (VIII) was then treated with mesyl chloride followed by treatment with palladium, and coupling with a Boc protected amino acid (Boc-AA-OH) (e.g., Boc-protected Serine) to provide a compound of formula (IX).

formula (VIII)
i) MsCl
ii) HCOONH₄Pd/C, Pd(OH)₂, AcOH
iii) Boc-Amino Acid-OH formula (IX)

The compound of formula (IX) was subsequently deprotected with acid and coupled with a coupling agent (e.g., with an acid chloride) to provide a compound of formula (X).

formula (IX)
i) H⁺ deprotection
ii) coupling formula (X)

In other instances, the compound of formula (VIII) is treated under reducing conditions with hydrogen and palladium prior to coupling with a Boc protected amino acid to provide a compound of formula (XI), allowing a variety of substitutions (e.g., alkyl or amide) to occur at the ring nitrogen.

formula (VIII)
i) H2 Pd/C
ii) Boc-Amino Acid-OH

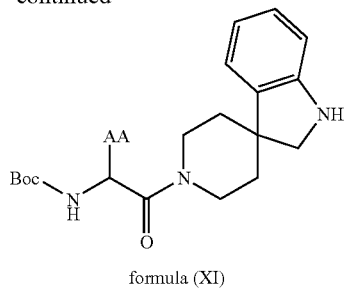

formula (XI)

In some instances, the compound of formula (IX) was subsequently deprotected with acid and coupled with a sulfonyl chloride to provide a sulfonamide compound (e.g, as below).

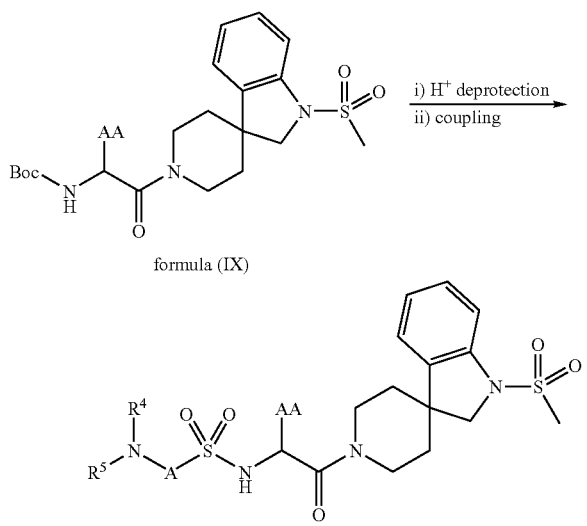

formula (IX)

The term "Boc" means N-tert-Butoxycarbonyl.

The term "Cbz" means carbobenzyloxy.

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Additionally, the compounds disclosed herein can be prepared on a solid support or using a solid phase peptide synthesis.

The term "solid support" refers a material to which a compound is attached to facilitate identification, isolation, purification, or chemical reaction selectivity of the compound. Such materials are known in the art and include, for example, beads, pellets, disks, fibers, gels, or particles such as cellulose beads, pore-glass beads, silica gels, polystyrene beads optionally cross-linked with divinylbenzene and optionally grafted with polyethylene glycol, poly-acrylamide beads, latex beads, dimethylacrylamide beads optionally cross-linked with N,N'-bis-acryloyl ethylene diamine, glass particles coated with hydrophobic polymer, and material having a rigid or semi-rigid surface. The solid supports optionally have functional groups such as amino, hydroxy, carboxy, or halo groups, (see, Obrecht, D. and Villalgrodo, J. M., *Solid-Supported Combinatorial and Parallel Synthesis of Small-Molecular-Weight Compound Libraries*, Pergamon-Elsevier Science Limited (1998)), and include those useful in techniques such as the "split and pool" or "parallel" synthesis techniques, solid-phase and solution-phase techniques, and encoding techniques (see, for example, Czamik, A. W., *Curr. Opin. Chem. Bio.*, (1997) 1, 60).

The term "solid phase peptide" refers to an amino acid, which is chemically bonded to a resin (e.g., a solid support). Resins are generally commercially available (e.g., from SigmaAldrich). Some examples of resins include Rink-resins, Tentagel S RAM, MBHA, and BHA-resins.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

Evaluating Compounds

A variety of methods can be used to evaluate a compound for ability to modulate GHS-R activity. Evaluation methods include in vitro binding assays, in vitro cell-based signalling assays, and in vivo methods. The evaluation methods can evaluate binding activity, or an activity downstream of GHS-R, e.g., a signaling activity downstream of GHS-R such as inositol phosphate production, Ca$^{2+}$ mobilization, or gene transcription (e.g., CREB-mediated gene transcription).

Binding assays. Generally, the compounds can be evaluated to determine if they bind to GHS-R and if they compete with one or more known compounds that interact with GHS-R, and the extent of such interactions. For example, the compounds can be evaluated to determine if they compete with ghrelin, ipamorelin, L-692,400 or L-692,492.

One exemplary binding assay is as follows: GHS-R expressing COS-7 cells cultured at a density of 1×10$^5$ cells per well so that binding is assayed in the range of about 5-8% binding of the radioactive ligand. For example, the cells can express an endogenous nucleic acid encoding GHS-R or an exogenous nucleic acid encoding GHS-R. Cells transfected with an exogenous nucleic acid encoding GHS-R can be used, e.g., two days, after transfection. Competition binding experiments are performed for 3 hours at 4° C. using 25 pM of $^{125}$I-ghrelin in 0.5 ml of 50 mM HEPES buffer, pH 7.4, supplemented with 1 mM CaCl$_2$, 5 mM MgCl$_2$, and 0.1% (w/v) bovine serum albumin, 40 mg/ml bacitracin. Non-specific binding can be determined as the binding in the presence of 1 mM of unlabeled ghrelin. Cells are washed twice in 0.5 ml of ice-cold buffer and then lysed with 0.5-1 ml of lysis buffer (8 M Urea, 2% NP40 in 3 M acetic acid). After washing and lysis, the bound radioactivity is counted. Assays can be run in duplicate or triplicate, e.g., to provide statistical power.

Values of the dissociation and inhibition constants (Kd and Ki) can be estimated from competition binding experiments using the equation:

$$Kd=IC50-L \text{ and } Ki=IC50/(1+L/Kd),$$

where L is the concentration of radioactive ligand. Bmax values can be estimated from competition binding experiments using the equation Bmax=B0 IC50/[ligand], where B0 is the specifically bound radioligand.

Cell-Based Activity Assays. For example, the ability of the compound to modulate accumulation of a second messenger signaling component downstream of GHS-R can be evaluated. For example, inositol phosphates (IP), as a result of Gq signaling in a mammalian cell, e.g., a Cos-7 cells. Other tissue culture cells, Xenopus oocytes, and primary cells can also be used.

Phosphatidylinositol turnover assay. One day after transfection COS-7 cells are incubated for 24 hours with 5 μCi of [$^3$H]-myo-inositol in 1 ml medium supplemented with 10% fetal calf serum, 2 mM glutamine and 0.01 mg/ml gentamicin per well. Cells are then washed twice in buffer, 20 mM HEPES, pH 7.4, supplemented with 140 mM NaCl, 5 mM KCl, 1 mM MgSO$_4$, 1 mM CaCl$_2$, mM glucose, 0.05% (w/v) bovine serum; and incubated in 0.5 ml buffer supplemented with 10 mM LiCl at 37° C. for 30 min. For some assays, it is also useful to incubate the cells with adenosine deaminase ADA (200 U/mg, Boehringer Mannheim, Germany) for 30 min in a concentration of 1 U/ml.

After incubation with the compound of interest for 45 min at 37° C., cells are extracted with 10% ice-cold perchloric acid and placed on ice for 30 min. The resulting supernatants are neutralized with KOH in HEPES buffer, and [$^3$H]-inositol phosphate is purified on Bio-Rad AG 1-X8 anion exchange resin as described. Assays can be run in duplicate, triplicate, etc.

Other second messenger assays. Another second messenger that can be evaluated is Ca$^{2+}$. Ca$^{2+}$ mobilization can be evaluated using a calcium sensitive detector, such as aequorin protein or a dye, e.g., FURA-2. In an exemplary assay, calcium mobilization is evaluated in a recombinant cell that expresses GHS-R and aequorin.

Gene expression assay. HEK293 cells (30 000 cells/well) seeded in 96-well plates are transiently transfected with a mixture of pFA2-CREB and pFR-Luc reporter plasmid (PathDetect™ CREB trans-Reporting System, Stratagene) and nucleic acid encoding GHS. One day after transfection, cells are treated with the compound of interest in an assay volume of 100 μl medium for 5 hrs. After treatment, cells are cultured in low serum (2.5%). After the incubation period, the assay is ended by washing the cells twice with PBS and adding 100 μl luciferase assay reagent (LucLite™, Packard Bioscience). Luminescence is measured (e.g., as relative light units (RLU)) using in a luminometer such as the TopCounter™ (Packard Bioscience) for 5 sec.

Other transcription based assays can include evaluating transcription of GHS-R regulated genes in primary cells that express GHS-R (e.g., cells from pituitary, brain, spinal cord, uterus, spleen, pancreas, kidney, adrenal gland, skeletal muscle, thyroid, liver, small intestine, and heart) or in recombinant cells that express GHS-R. mRNA levels can be evaluated by any method, e.g., microarray analysis, Northern blotting, or RT-PCR. Exemplary genes that are directly or indirectly regulated by GHS-R activity include leptin, resistin, and adiponectin. GHS-R activity may also affect insulin, IGF-1, and leptin levels in circulation.

IC$_{50}$ and EC$_{50}$ values can be determined by nonlinear regression, e.g., using the Prism 3.0 software (GraphPad Software, San Diego).

In vivo assays. Exemplary in vivo assays include the fast-refeeding assay described in Example 1 and as follows.

Prior to compound administration, mice are weighed and sorted into groups based on comparable body weight. Food is removed at 6 pm for an overnight (~16 hour) fast. Beginning at 10 am on the next morning, mice are administered with either vehicle (e.g., saline+acetic acid, pH=5) or the compound of interest. Mice are then returned to their home cages and pre-weighed food (approximately 90 grams) is immediately returned to the food hoppers in each cage. The weight of the food remaining in the food hoppers is measured at 30 minutes, 1 hour, 2 hours, and 4 hours post compound/vehicle administration. Final body weights are then recorded for the mice.

The compound of interest can also be evaluated in other experiments. For example, the compound can be administered to lean or obese mice (e.g., (ob/ob) C57BL/6J mice), or other experimental animals. The compound can be administered intraperitoneally or intracerebroventricularly. After administration, the animal is evaluated, e.g., for feeding behavior, anxiety, or one or more physiological parameters, e.g., a metabolic parameter.

ICV Administration. For intra-third cerebroventricular (ICV) administration, each drug can be diluted in 4 μl of artificial cerebrospinal fluid for injection. For ICV injection, mice are anaesthetised with sodium pentobarbital (80-85 mg/kg intraperitoneally) and placed in a stereotaxic instrument seven days before the experiments. A hole is made in each skull using a needle inserted 0.9 mm lateral to the central suture and 0.9 mm posterior to the bregma. A 24 gauge cannula bevelled at one end over a distance of 3 mm is implanted into the third cerebral ventricle for ICV injection.

Gastric emptying assessment. Another test for food consumption after administration of a compound of interest is the gastric emptying assessment. Before the gastric emptying assessment, mice are food deprived for 16 hours with free access to water. Fasted mice are given free access to pre-weighed pellets for one hour and then administered the compound of interest. The mice are again deprived of food for one or two hours after the compound administration. Food intake is measured by weighing uneaten pellets. Mice are killed by cervical dislocation two or three hours after the compound administration. Immediately after the stomach was exposed by laparotomy, quickly ligated at both the pylorus and cardia, removed, and the dry content is weighed. Gastric emptying is calculated according to the following formula: gastric emptying (%)=(1−(dry weight of food recovered from the stomach/weight of food intake))×100.

Anxiety tests. Anxiety can be assessed in the standard elevated plus maze, 50 cm above the ground. The four arms can be made 27 cm long and 6 cm wide. Two opposing arms are enclosed by walls 15 cm high (closed arms) while the other arms are devoid of walls (open arms). Each mouse is placed in the center of the maze facing one of the enclosed arms 10 minutes after injection with a compound. The cumulative time spent in each arm and the number of entries into the open or closed arms is recorded during a five minute test session. The time spent in the open arms is expressed as a percentage of total entry time (100·open/open+closed) and the number of entries in the open arms is expressed as a percentage of the total number of entries (100·open/total entries).

Parameter analysis. Mice or other animals provided with the test compound can be analyzed for one or more biological parameters, e.g., metabolic parameters. For mice, serum is obtained from blood from the orbital sinus under ether anaesthesia at the end of a treatment (e.g., eight hours after removal of food and the final intraperitoneal injection). Mice are killed by cervical dislocation. Immediately after, the epididymal fat pad mass can be assessed based on removal and weighing of the white adipose tissue (WAT) and the gastrocnemius muscle. Blood glucose can be measured by the glucose oxidase method. Serum insulin and free fatty acids (FFA) can be measured by enzyme immunoassay and an enzymatic method (Eiken Chemical Co., Ltd, Tokyo, Japan), respectively. Serum triglycerides and total cholesterol can be measured by an enzymatic method (Wako Pure Chemical Industries, Ltd, Tokyo, Japan).

mRNA analysis. RNA is isolated from the stomach, epididymal fat or other relevant tissues using the RNeasy Mini Kit (Qiagen, Tokyo, Japan). Total RNA is denatured with formaldehyde, electrophoresed in 1% agarose gel, and blotted onto a Hybond N+membrane. The membranes are hybridized with a labelled cDNA probe (e.g., radioactively, chemically, or fluorescently labelled) for the gene of interest. The total integrated densities of hybridization signals can be determined by densitometry. Data can be normalized to a glyceraldehyde 3-phosphate dehydrogenase mRNA abundance or to actin mRNA abundance and expressed as a percentage of controls. Exemplary genes that can be evaluated include ghrelin, leptin, resistin, and adiponectin. It is also possible to use a transgenic animal that includes a reporter construct with a regulatory region from the gene of interest or to use a recombinant cell with such a construct.

A compound described herein can have a $K_i$ (as an antagonist) of less than 200, 100, 80, 70, 60, or 50 nM, in one or more of the described assays. A compound described herein can have a $K_D$ as an agonist of greater than 20, 40, 50, 100, 200, 300, or 500 nM, in one or more of the described assays.

A compound described herein can also specifically interact with GHS-R, e.g., relative to other cell surface receptors. The motilin receptor, for example, is a homolog of GHS-R. A disclosed compound may preferentially interact with GHS-R relative to the motilin receptor, e.g., at least a 2, 5, 10, 20, 50, or 100 preference. In another embodiment, the disclosed compound may also interact with motilin receptor, and, e.g., alter motilin receptor activity.

In one embodiment, the compound may alter an intracellular signaling activity downstream of GHS-R, e.g., Gq signaling, phospholipase C signaling, and cAMP response element (CRE) driven gene transcription.

Compounds may also be evaluated for their therapeutic activity with respect to any disorder, e.g., a disorder described herein. Animal models for many disorders are well known in the art.

Cells and animals for evaluating the effect of a compound on ALS status include a mouse which has an altered SOD gene, e.g., a SOD1-G93A transgenic mouse which carries a variable number of copies of the human G93A SOD mutation driven by the endogenous promoter, a SOD1-G37R transgenic mouse (Wong et al., Neuron, 14(6):1105-16 (1995)); SOD1-G85R transgenic mouse (Bruijn et al., Neuron, 18(2): 327-38 (1997)); *C. elegans* strains expressing mutant human SOD1 (Oeda et al., Hum Mol. Genet., 10:2013-23 (2001)); and a *Drosophila* expressing mutations in Cu/Zn superoxide dismutase (SOD). (Phillips et al., Proc. Natl. Acad. Sci. U.S.A., 92:8574-78 (1995) and McCabe, Proc. Natl. Acad. Sci. U.S.A., 92:8533-34 (1995)).

Cells and animals for evaluating the effect of a compound on Alzheimer's disease are described, e.g., in U.S. Pat. No. 6,509,515 and U.S. Pat. Nos. 5,387,742; 5,877,399; 6,358, 752; and 6,187,992. In U.S. Pat. No. 6,509,515, the animal expresses an amyloid precursor protein (APP) sequence at a level in brain tissues such that the animal develops a progressive neurologic disorder. An exemplary animal model for evaluating polyglutamine-based aggregation is the transgenic mouse strain is the R6/2 line (Mangiarini et al. Cell 87: 493-506 (1996)).

Models for evaluating the effect of a test compound on muscle atrophy include, e.g.,: 1) rat medial gastrocnemius muscle mass loss resulting from denervation, e.g., by severing the right sciatic nerve at mid-thigh; 2) rat medial gastrocnemius muscle mass loss resulting from immobilization, e.g., by fixed the right ankle joint at 90 degrees of flexion; 3) rat medial gastrocnemius muscle mass loss resulting from hindlimb suspension; (see, e.g., U.S. 2003-0129686); 4) skeletal muscle atrophy resulting from treatment with the cachectic cytokine, interleukin-1 (IL-1) (R. N. Cooney, S. R. Kimball, T. C. Vary, Shock 7, 1-16 (1997)); and 5) skeletal muscle atrophy resulting from treatment with the glucocorticoid, dexamethasone (A. L. Goldberg, J Biol Chem 244, 3223-9 (1969).). Models 1, 2, and 3 induce muscle atrophy by altering the neural activity and/or external load a muscle experiences to various degrees. Models 4 and 5 induce atrophy without directly affecting those parameters.

Exemplary animal models for AMD (age-related macular degeneration) include: laser-induced mouse model simulating exudative (wet) macular degeneration Bora et al., Proc. Natl. Acad. Sci. USA., 100:2679-84 (2003); a transgenic mouse expressing a mutated form of cathepsin D resulting in features associated with the "geographic atrophy" form of AMD (Rakoczy et al., Am. J. Pathol., 161:1515-24 (2002)); and a transgenic mouse overexpressing VEGF in the retinal pigment epithelium resulting in CNV. Schwesinger et al., Am. J. Pathol. 158:1161-72 (2001).

Exemplary animal models of Parkinson's disease include primates rendered parkinsonian by treatment with the dopaminergic neurotoxin 1-methyl-4 phenyl 1,2,3,6-tetrahydropyridine (MPTP) (see, e.g., US Appl 20030055231 and Wichmann et al., Ann. N.Y. Acad. Sci., 991:199-213 (2003); 6-hydroxydopamine-lesioned rats (e.g., Lab. Anim. Sci., 49:363-71 (1999)); and transgenic invertebrate models (e.g., Lakso et al., J. Neurochem., 86:165-72 (2003) and Link, Mech. Ageing Dev., 122:1639-49 (2001)).

Exemplary molecular models of Type II diabetes include: a transgenic mouse having defective Nkx-2.2 or Nkx-6.1; (U.S. Pat. No. 6,127,598); Zucker Diabetic Fatty fa/fa (ZDF) rat. (U.S. Pat. No. 6,569,832); and Rhesus monkeys, which spontaneously develop obesity and subsequently frequently progress to overt type 2 diabetes (Hotta et al., Diabetes, 50:1126-33 (2001); and a transgenic mouse with a dominant-negative IGF-I receptor (KR-IGF-IR) having Type 2 diabetes-like insulin resistance.

Exemplary animal and cellular models for neuropathy include: vincristine induced sensory-motor neuropathy in mice (US Appl 5420112) or rabbits (Ogawa et al., Neurotoxicology, 21:501-11 (2000)); a streptozotocin (STZ)-diabetic rat for study of autonomic neuropathy (Schmidt et al., Am. J. Pathol., 163:21-8 (2003)); and a progressive motor neuropathy (pmn) mouse (Martin et al., Genomics, 75:9-16 (2001)).

With respect to neoplastic disorders, again, numerous animal and cellular models have been described. An exemplary in vivo system for evaluating a compound for its ability to limit the spread of primary tumors is described by Crowley et al., *Proc. Natl. Acad. Sci.,* 90:5021-5025 (1993). Nude mice are injected with tumor cells (PC3) engineered to express CAT (chloramphenicol acetyltransferase). Compounds to be tested for their ability to decrease tumor size and/or metastases are administered to the animals, and subsequent measurements of tumor size and/or metastatic growths are made. The level of CAT detected in various organs provides an indication of the ability of the compound to inhibit metastasis; detection of less CAT in tissues of a treated animal versus a control animal indicates less CAT-expressing cells have migrated to that tissue or have propagated within that tissue.

Administration of Compounds and Formulations Thereof

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.001 to about 100 mg/kg of body weight, e.g., between 0.001-1 mg/kg, 1-100 mg/kg, or 0.01-5 mg/kg, every 4 to 120 hours, e.g., about every 6, 8, 12, 24, 48, or 72 hours, or according to the requirements of the particular compound. The methods herein contemplate administration of an effective amount of compound or compound composition to achieve the desired or stated effect (e.g., reduction of feeding in a subject). Typically, the pharmaceutical compositions of this invention will be administered from about 1 to about 6 times per day, for example, the compounds can be administered about 1 to about 4 (e.g., 1, 2, 3, or 4) hours prior to meal time. Alternatively, the compounds can be administered as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Pharmaceutical compositions of this invention comprise a compound of the formulae described herein or a pharmaceutically acceptable salt thereof; an additional compound including for example, a steroid or an analgesic; and any pharmaceutically acceptable carrier, adjuvant or vehicle. Alternate compositions of this invention comprise a compound of the formulae described herein or a pharmaceutically acceptable salt thereof; and a pharmaceutically acceptable carrier, adjuvant or vehicle. The compositions delineated herein include the compounds of the formulae delineated herein, as well as additional therapeutic compounds 1f present, in amounts effective for achieving a modulation of disease or disease symptoms, including kinase mediated disorders or symptoms thereof. The compositions are made by methods including the steps of combining one or more compounds delineated herein with one or more carriers and, optionally, one or more additional therapeutic compounds delineated herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase which can be combined with emulsifying and/or suspending agents. If desired, certain sweetening and/or flavoring and/or coloring agents may be added.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

In some cases, the pH of the formulation may be adjusted with pharmaceutically acceptable acids, bases or buffers to enhance the stability of the formulated compound or its delivery form.

The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional compound should be present at dosage levels of between about 1 to 100%, and more preferably between about 5 to 95% of the dosage normally administered in a monotherapy regimen. The additional compounds may be administered separately, as part of a multiple dose regimen, from the compounds of this invention. Alternatively, those compounds may be part of a single dosage form, mixed together with the compounds of this invention in a single composition.

Treatments

The compounds described herein can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a disorder, or "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Many compounds described herein can be used to treat or prevent a metabolic disorder. A "metabolic disorder" is a disease or disorder characterized by an abnormality or malfunction of metabolism. One category of metabolic disorders are disorders of glucose or insulin metabolism. For example, the subject can be insulin resistant, e.g., have insulin-resistance diabetes. In one embodiment, compounds of class A or C are used to decrease insulin or glucose levels in a subject. In another embodiment, compounds of class B are used to alter (e.g., increase) insulin or glucose levels in a subject. Compounds of class D may also be used to alter insulin or glucose levels in a subject. Treatment with the compound may be in an amount effective to improve one or more symptoms of the metabolic disorder.

Many compounds described herein can be used to treat or prevent obesity, e.g., in a human subject, e.g. a child or adult subject. "Obesity" refers to a condition in which a subject has a body mass index (BMI) of greater than or equal to 30. Many compounds described herein can be used to treat or prevent an over-weight condition. "Over-weight" refers to a condition in which a subject has a body mass index of greater or equal to 25.0. The body mass index and other definitions are according to the "NIH Clinical Guidelines on the Identification and Evaluation, and Treatment of Overweight and Obesity in Adults" (1998). Treatment with the compound may be in an amount effective to alter the weight of the subject, e.g., by at least 2, 5, 7, 10, 12, 15, 20, 25, 30, 25, 40, 45, 50, or 55%. Treatment with the compound may be in an amount effective to reduce the body mass index of the subject, e.g., to less than 30, 28, 27, 25, 22, 20, or 18. The compounds can be used to treat or prevent aberrant or inappropriate weight gain, metabolic rate, or fat deposition, e.g., anorexia, bulimia, obesity, diabetes, or hyperlipidemia, as well as disorders of fat or lipid metabolism.

For example, agonists of GHS-R can be used to increase food intake or to treat disorders associated with weight loss, e.g., anorexia, bulimia, and so forth In one embodiment, a compound of class B is used to treat such disorders. In another embodiment, a compound of class D is used to treat such disorder.

Antagonists of GHS-R can be used to treat aberrant or inappropriate weight gain, metabolic rate, or fat deposition, e.g., obesity, diabetes, or hyperlipidemia, as well as disorders of fat or lipid metabolism that results in weight gain. In one embodiment, a compound of class A is used to treat such disorders. In another embodiment, a compound of class C is used to treat such disorders. In another embodiment, a compound of class D is used to treat such disorders. In one embodiment, a compound of class A, C, or D is used to treat hypothalamic obesity. For example, the compound can be administered to a subject identified as at risk for hypothalamic obesity or to a subject that has an abnormal (e.g., extreme) insulin response to glucose.

Many compounds described herein can be used to treat a neurological disorder. A "neurological disorder" is a disease or disorder characterized by an abnormality or malfunction of neuronal cells or neuronal support cells (e.g., glia or muscle). The disease or disorder can affect the central and/or peripheral nervous system. Exemplary neurological disorders include neuropathies, skeletal muscle atrophy, and neurodegenerative diseases, e.g., a neurodegenerative disease other than one caused at least in part by polyglutamine aggregation. Exemplary neurodegenerative diseases include: Alzheimer's, Amyotrophic Lateral Sclerosis (ALS), and Parkinson's disease. Another class of neurodegenerative diseases includes diseases caused at least in part by aggregation of polyglutamine. Diseases of this class include: Huntington's Diseases, Spinalbulbar Muscular Atrophy (SBMA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCA7), and Spinocerebellar Ataxia 12 (SCA12). Treatment with the compound may be in an amount effective to ameliorate at least one symptom of the neurological disorder. In one embodiment, a compound of class A or C can be used to treat the neurological disorder. In another embodiment, a compound of class D can be used to treat the neurological disorder.

Many compounds described herein can be used to modulate anxiety in a subject. In one embodiment, a compound of class A or C can be used to decrease anxiety. In another embodiment, a compound of class D can be used to decrease anxiety.

Many compounds described herein can be used to modulate memory retention in a subject. In one embodiment, a compound of class A or C can be used to decrease memory retention. For example, decreasing memory retention may aid recovery from traumatic stress. In one embodiment, a compound of class B is used to increase memory retention. In another embodiment, a compound of class D is used to modulate memory retention.

Many compounds described herein can be used to modulate sleep, sleep cycles (e.g., REM sleep), or wakefulness in a subject. In one embodiment, a compound of class B is used to promote sleep in the subject or to treat sleep apnea.

In one embodiment, a GHS-R agonist or antagonist (e.g., a compound described herein, is used to alter the circadian rhythm of a subject. For example, the compound can be delivered at particular times of day, e.g., regularly, e.g., in the evening and/or morning, to reset a circadian rhythm, e.g., prior to, during, or after traveling between timezones, or to a subject having a circadian disorder. The compounds can, e.g., modulate the pulsatility of GH secretion.

Many compounds described herein can be used to treat a cardiovascular disorder. A "cardiovascular disorder" is a disease or disorder characterized by an abnormality or malfunction of the cardiovascular system, e.g., heart, lung, or blood vessels. Exemplary cardiovascular disorders include: cardiac dysrhythmias, chronic congestive heart failure, ischemic stroke, coronary artery disease and cardiomyopathy. Treatment with the compound may be in an amount effective to ameliorate at least one symptom of the cardiovascular disorder. In one embodiment, a compound of class A, C, or D can be used to treat the cardiovascular disorder.

Many compounds described herein can be used to treat a dermatological disorder or a dermatological tissue condition. A "dermatological disorder" is a disease or disorder characterized by an abnormality or malfunction of the skin. A "dermatological tissue condition" refers to the skin and any underlying tissue (e.g., support tissue) which contributes to the skin's function and/or appearance, e.g., cosmetic appearance. Treatment with the compound may be in an amount effective to ameliorate at least one symptom of the dermatological disorder or the dermatological tissue condition. In one embodiment, a compound of class A, C, or D can be used to treat the dermatological disorder or dermatological tissue condition.

Many compounds described herein can be used to treat a geriatric disorder. A "geriatric disorder" is a disease or disorder whose incidence, at the time of filing of this application and in a selected population of greater than 100,000 individuals, is at least 70% among human individuals that are greater than 70 years of age. In one embodiment, the geriatric disorder is a disorder other than cancer or a cardio-pulmonary disorder. A preferred population is a United States population. A population can be restricted by gender and/or ethnicity.

Many compounds described herein can be used to treat or prevent a disorder characterized by excessive growth hormone activity. For example, the compounds can be used to reduce GH levels in the subject. In one embodiment, the subject is a human, e.g., a child (e.g., between 3-11 years), an adolescent (e.g., between 12-19 years), a young adult (e.g., between 20-25 years), or an adult. In one embodiment, a compound of class A, C, or D is used to treat the disorder characterized by excessive growth hormone activity.

Many compounds described herein can be used to modulate vagal tone. For example, a compound described herein or other modulator of GHS-R can be administered to a subject who has a vagotomy or other disorder which alters vagal afferent or efferent activity. In one embodiment, a subject is monitored for abnormalities in vagal nerve function, and, if a malfunction is detected, the subject is treated with a compound described herein or other modulator of GHS-R.

Exemplary diseases and disorders that are relevant to certain implementations include: cancer (e.g., breast cancer, colorectal cancer, CCL, CML, prostate cancer); skeletal muscle atrophy; adult-onset diabetes; diabetic nephropathy, neuropathy (e.g., sensory neuropathy, autonomic neuropathy, motor neuropathy, retinopathy); obesity; bone resorption; neurodegenerative disorders (Parkinson's disease, ALS, Alzheimer's, short-term and long-term memory loss), and disorders associated with protein aggregation (e.g., other than polyglutamine aggregation) or protein misfolding; age-related macular degeneration, Bell's Palsy; cardiovascular disorders (e.g., atherosclerosis, cardiac dysrhythmias, chronic congestive heart failure, ischemic stroke, coronary artery disease and cardiomyopathy), chronic renal failure, type 2 diabetes, ulceration, cataract, presbiopia, glomerulonephritis, Guillan-Barre syndrome, hemorrhagic stroke, rheumatoid arthritis, inflammatory bowel disease, multiple sclerosis, SLE, Crohn's disease, osteoarthritis, pneumonia, and urinary incontinence. Symptoms and diagnosis of diseases are well known to medical practitioners.

In certain embodiments, the compounds are directed locally to GHS-R in a target tissue of the organism. GHS-R is expressed in the hypothalamus, heart, lung, pancreas, intestine, brain (particularly in the arcuate nucleus (ARC)), and adipose tissue. A compound described herein can be targeted to one or more of the above tissues. For example, the compound can be formulated for inhalation for targeting to the lung. The compound can be formulated for ingestion, and passage to the intestine for targeting to the intestine. In other embodiments, treatment is directed systemically, and the compound is distributed to the target tissue.

Depending on the disorder and the compound, treatment may involve, in addition to use of a compound in a class specified above, using a compound in another class. For example, in subjects whose endogenous ghrelin levels are lower than normal generally or lower than normal in an affected region, a treatment may involve using a compound of class B or D. In other subjects whose endogenous ghrelin levels are higher than normal generally or higher than normal in an affected region, treatment may involve using a compound of class A, C, or D. The suitability of a particular compound can be evaluated, e.g., in an animal-based assay or by monitoring a subject.

Many compounds described herein can be used to modulate activity of a biological signal that controls energy balance. Such signals include peptide signals, such as NPY, AGRP, orexins, MCH, beacon (see, e.g., Collier et al. (2000) Diabetes 49:1766), mealoncyte-stimulating hormone, neuromedin U, corticotrophin-releasing factor, and leptin. For example, NPY is a 36-amino acid peptide that stimulates food intact and depresses metabolic rate. Many compounds described herein can be used to decrease NPY activity. Many compounds described herein can be used to increase activity or availability of an anorexigenic molecule, e.g., bombesin, IL-1β, leptin, and gastrin-releasing peptide. Accordingly, the compounds may increase the discharge rate of the gastric vagal afferent.

We have also found that substance P and derivatives thereof can modulated GHS-R activity. In particular, we found that substance P alters feeding activity of mice in the fast refeed assay. Accordingly, substance P and derivatives thereof can be used to modulating an eating or metabolic disorder as well as other disorders described herein.

Our investigation of GHS-R expression in human tissues has demonstrated that GHS-R is expressed in pituitary cells, brain, spinal cord, uterus, spleen, pancreas, kidney, adrenal gland, skeletal muscle, thyroid, liver, small intestine, and heart. Accordingly, compounds described herein can be used to treat diseases and disorders associated with undesired levels of ghrelin or ghrelin-mediated signalling activity in those tissues. For example, if the level of ghrelin or ghrelin-mediated signalling activity is undesirably low, a compound of class B or D can be used for treatment. If the level of ghrelin or ghrelin-mediated signalling activity is undesirably high, a compound of class A, C, or D can be used for treatment. For example, the level of desired ghrelin activity can vary from tissue to tissue. Ghrelin is secreted by the stomach and may be high in or near the stomach, but much lower in normal pancreatic tissue.

Neoplastic Disorders

Many compounds described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders (e.g., tumors arising from prostate, colon, lung, breast and liver origin), hematopoietic neoplastic disorders, e.g., leukemias, metastatic tumors. Prevalent cancers include: breast, prostate, colon, lung, liver, and pancreatic cancers. Treatment with the compound may be in an amount effective to ameliorate at least one symptom of the neoplastic disorder, e.g., reduced cell proliferation, reduced tumor mass, etc.

Whether a neoplastic disorder should be treated with a GHS-R agonist or antagonist can depend on the type of neoplasia. For example, Duxbury et al. (2003) Biochem. Biophys. Res. Comm. 309:464-468 report that certain neoplastic disorders are inhibited by GHS-R antagonists. These disorders include, e.g., pancreatic adenocarcinoma, and neoplasias in which GHS-R or GHS-R1b is expressed, e.g., prostate adenocarcinoma, pancreatic endocrine tumors, somatotroph tumors, and central nervous system tumors. Neoplasias that are attenuated, inhibited, or killed by a GHS-R antagonist are term, herein, "GHS-R antagonist-sensitive neoplastic disorders" and can be treated with a compound of class A, C, or D.

Duxbury et al. also report that certain other types of neoplasia, e.g., breast, lung, and thyroid adenocarcinomas can be inhibited by high levels ghrelin (>10 nM) and, accordingly, can be treated with a GHS-R agonist, e.g., a GHS-R agonist described herein or another known GHS-R agonist. Neoplasias that are attenuated, inhibited, or killed by ghrelin or a GHS-R agonist are term, herein, "ghrelin-sensitive neoplastic disorders" and can be treated with a compound of class B or D.

Whether a neoplastic cell is sensitive to a ghrelin agonist or antagonist (i.e., whether the neoplastic cell is a ghrelin-sensitive or GHS-R antagonist sensitive neoplastic disorder) can be determined by a proliferation assay in the presence of a GHS-R agonist, e.g., ghrelin, or antagonist, e.g., D-Lys-GHRP6. Duxbury et al. disclose an exemplary proliferation assay. In one such assay, cells are seeded into 96 well plates with about $10^4$ cell per well. The cells are cultured for 3 days in medium, then contacted with ghrelin or D-Lys-GHRP6, or a control medium. Cells are then evaluated using the MTT assay (3-(4,5-dimethylthiazolyl-2-yl)-2,5-diphenyltetrazolium) (from Trevigen, Gaithersburg, Md.) for viability. Other assays that can be performed are invasion and migration assays. The affect of a particular compound may also depend on concentration which can also be varied in the assay.

In addition to the above-mentioned neoplastic disorders, compounds described herein can be used to treat other neoplasias and hyperplasias including "tumors," which may be benign, premalignant or malignant.

Further examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), and genitourinary tract (e.g., renal, urothelial cells), pharynx, prostate, ovary as well as adenocarcinomas which include malignancies such as most colon cancers, rectal cancer, renal-cell carcinoma, liver cancer, non-small cell carcinoma of the lung, cancer of the small intestine and so forth. Metastatic lesions of the aforementioned cancers can also be treated or prevented using the methods and compositions of the invention.

A compound described herein can be useful in treating malignancies of the various organ systems, such as those affecting lung, breast, lymphoid, gastrointestinal (e.g., colon), and genitourinary tract, prostate, ovary, pharynx, as well as adenocarcinomas which include malignancies such as most colon cancers, renal-cell carcinoma, prostate cancer and/or testicular tumors, non-small cell carcinoma of the lung, cancer of the small intestine and cancer of the esophagus. Exemplary solid tumors that can be treated include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The term "carcinoma" is recognized by those skilled in the art and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary.

The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is recognized by those skilled in the art and refers to malignant tumors of mesenchymal derivation.

The subject method can also be used to inhibit the proliferation of hyperplastic/neoplastic cells of hematopoietic origin, e.g., arising from myeloid, lymphoid or erythroid lineages, or precursor cells thereof. For instance, the invention contemplates the treatment of various myeloid disorders including, but not limited to, acute promyeloid leukemia (APML), acute myelogenous leukemia (AML) and chronic myelogenous leukemia (CML) (reviewed in Vaickus, L. (1991) *Crit. Rev. in Oncol./Hemotol.* 11:267-97). Lymphoid malignancies which may be treated by the subject method include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas contemplated by the treatment method of the invention include, but are not limited to, non-Hodgkin's lymphoma and variants thereof, peripheral T-cell lymphomas, adult T-cell leukemia/lymphoma (ATL), cutaneous T-cell lymphoma (CTCL), large granular lymphocytic leukemia (LGF) and Hodgkin's disease.

Metabolic Syndrome

The invention provides a method of treating metabolic syndrome, including administering to a subject an effective amount of a compound described herein.

The metabolic syndrome (e.g., Syndrome X) is characterized by a group of metabolic risk factors in one person. They include: central obesity (excessive fat tissue in and around the abdomen), atherogenic dyslipidemia (blood fat disorders—mainly high triglycerides and low HDL cholesterol—that foster plaque buildups in artery walls); insulin resistance or glucose intolerance (the body can't properly use insulin or blood sugar); prothrombotic state (e.g., high fibrinogen or plasminogen activator inhibitor [−1] in the blood); raised blood pressure (i.e., hypertension) (130/85 mmHg or higher); and proinflammatory state (e.g., elevated high-sensitivity C-reactive protein in the blood).

The underlying causes of this syndrome are overweight/obesity, physical inactivity and genetic factors. People with metabolic syndrome are at increased risk of coronary heart disease, other diseases related to plaque buildups in artery walls (e.g., stroke and peripheral vascular disease) and type 2 diabetes. Metabolic syndrome is closely associated with a generalized metabolic disorder called insulin resistance, in which the body can't use insulin efficiently.

Agonizing GHS-R

Compounds of class B (e.g., GHS-R agonists) or D can be used to treat a disorder in which a subject has less than a desired or less than a normal level of GHS-R activity, e.g., in a particular tissue. Such compounds can be used to treat one or more of the following disorders: cachexia, wasting, stimulating growth hormone release in elderly humans; treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treating obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia; treatment of hypercortisonism and Cushing's syndrome; treatment of peripheral neuropathies; treatment of osteochondrody-splasias, Noonans syndrome, sleep disorders, schizophrenia, depression, Alzheimer's disease, delayed wound healing, and psychosocial deprivation; treatment of pulmonary dysfunction and ventilator dependency; prevention or treatment of congestive heart failure, improving pulmonary function, restoring systolic and diastolic function, increasing myocardial contractility, decreasing peripheral total vascular resistance, diminishing or preventing loss of body weight and enhancing recovery following congestive heart failure; increasing appetite; attenuation of protein catabolic response after a major operation; treating malabsorption syndromes; reducing protein loss due to chronic illness such as cancer or AIDS; accelerating weight gain and protein accretion in patients on TPN (total parenteral nutrition); treatment of hyperinsulinemia; treatment of gastric and duodenal ulcers; stimulation of thymic development; adjunctive therapy for patients on chronic hemodialysis; treatment of immunosuppressed patients; enhancement of an antibody response, e.g., following vaccination; increasing the total lymphocyte count of a human; treatment of syndromes manifested by non-restorative sleep and musculoskeletal pain, including fibromyalgia syndrome or chronic fatigue syndrome; improvement in muscle strength, mobility, maintenance of skin thickness, metabolic homeostasis, renal hemeostasis in the frail elderly; stimulation of osteoblasts, bone remodelling, and cartilage growth; prevention and treatment of congestive heart failure; protection of cardiac structure and/or cardiac function; enhancing of recovery of a mammal following congestive heart failure; enhancing and/or improving sleep quality as well as the prevention and treatment of sleep disturbances; enhancing or improving sleep quality by increasing sleep efficiency and augmenting sleep maintenance; prevention and treatment of mood disorders, in particular depression; improving mood and subjective well being in a subject suffering from depression; reducing insulin resistance; stimulation of the immune system; and increasing growth. The compounds can be used to treat a human or an animal, e.g., livestock, a pet, etc.

In some instances, a compound described herein is used in the treatment or prevention of ileus. Ileus (paralytic ileus, adynamic ileus) is temporary absence of the normal contractile movements of the intestinal wall. Like an obstruction of the intestines, ileus prevents the passage of intestinal contents. Unlike a mechanical obstruction, though, ileus rarely leads to rupture. Ileus commonly occurs for 24 to 72 hours after abdominal surgery. It may also be caused by an infection or a blood clot inside the abdomen, atherosclerosis that reduces the blood supply to the intestine, or an injury to an intestinal artery or vein. Disorders outside the intestine may cause ileus, such as kidney failure or abnormal levels of blood electrolytes, low potassium or high calcium levels, for example. Other causes of ileus are use of certain drugs (especially opioid analgesics and anticholinergic drugs) and an underactive thyroid gland. The symptoms of ileus are abdominal bloating, vomiting, severe constipation, loss of appetite, and cramps.

In some instances, a compound described herein is used in the treatment of gastroparesis. Gastroparesis, also called delayed gastric emptying, is a disorder in which the stomach takes too long to empty its contents. It often occurs in people with type 1 diabetes or type 2 diabetes. Gastroparesis happens when nerves to the stomach are damaged or stop working. The vagus nerve controls the movement of food through the digestive tract. If the vagus nerve is damaged, the muscles of the stomach and intestines do not work normally, and the movement of food is slowed or stopped. Diabetes can damage the vagus nerve if blood glucose levels remain high over a long period of time. High blood glucose causes chemical changes in nerves and damages the blood vessels that carry oxygen and nutrients to the nerves.

In some instances, a compound described herein is used in the treatment of cachexia. Cachexia is a condition of severe malnutrition characterized by anorexia, weight loss and muscle wasting that occurs as a consequence of chronic conditions such as cystic fibrosis, cerebral palsy, cancer, AIDS, congestive heart failure, failure to thrive in older populations, end-stage organ failure, neurological degenerative diseases, chronic obstructive lung disease, chronic liver disease, and chronic renal disease. Cachexia has repeatedly been associated with adverse clinical outcomes, and increased morbidity and mortality. Some symptoms of cachexia include the appearance of widespread of wasting of the body, pale color, dry wrinkled skin and mental depression, which can be a clinical sign of serious chronic disease, especially cancer. Severe cachexia occurs in most patients with advanced cancer or AIDS. The physiological, metabolic, and behavioral changes in cachexia are associated with patient complaints of weakness, fatigue, gastrointestinal distress, sleep/wake disturbances, pain, listlessness, shortness of breath, lethargy, depression, malaise and the fear of being a burden on family and friends. Although cachexia has been classically associated with chronic infections and malignant conditions, it has also been identified in patients after extensive traumatic injury and sepsis, and in aging persons with failure to thrive syndrome.

In some instances the compounds can be administered with another agent useful in the treatment of cachexia, such as a corticosteroid, a progestational agent, or a prokinetic agent.

In some instances, a compound described herein is used in the treatment of lipodystrophy. Lipodystrophy is a complicated disorder of adipose (fat) tissue. There are two main classes of lipodystrophy, inherited lipodystrophies (genetically determined), and acquired lipodystrophies (for example HIV-associated).

Examples of inherited lipodystrophies, which are very rare, occurring, for example in less than 1 in 10,000 people, include Congenital Generalized Lipodystrophy (CGL), Famililal Partial Lipodystrophy Dunnigan variety (FPLD), FPL Mandibuloacral Dysplasia, Kobberling, Multiple Symmetric Lipomatosis (MSL, Madelung's disease), SHORT Syndrome, and Neonatal Progeroid Syndrome (Wiedemann-Rautenstrauch Syndrome).

In general, about 30% to about 50% of HIV patients on highly active antiretroviral therapy (HAART) develop some form of lipodystrophic disorder. HIV-associated lipodystrophy is a disorder that generally includes subcutaneous fat loss in the face and limbs of HIV-positive patients after treatment with a protease inhibitor. In some instances, HIV lipodystrophy includes both fat loss and fat accumulation in various regions of the body, including the thighs/legs, breast, face, abdomen, and back. Other factors observed in patients with HIV-associated lipodystrophy syndrome include increased triglyceride levels, increased LDL and VLDL cholesterol, low HDL cholesterol and insulin resistance. In general, HIV treatment with a protease inhibitor (e.g., Crixivan, Viracept, etc) is a causative factor of HIV lipodystrophy. However, it has also been determined that treatment with a nucleoside reverse transcriptase inhibitor can also contribute to HIV lipodystrophy. Other risk factors that may contribute to lipodystrophy (e.g., HIV lipodystrophy) include age (e.g. older patients are more likely to develop HIV lipodystrophy), gender (e.g., in some instances women are more likely to develop HIV lipodystrophy than men), race, and dietary practices.

In some instances, the compounds can be used in combination treatment for HIV lipodystrophy with other therapeutic agents such as narcotics, growth hormones, anabolic steroids, and/or insulin senitizers.

Kits

A compound described herein can be provided in a kit. The kit includes (a) a composition that includes an compound described herein, and, optionally (b) informational material. The informational material can be descriptive, instructional, marketing or other material that relates to the methods described herein and/or the use of the compound described herein for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to use of the compound described herein to treat a disorder described herein.

In one embodiment, the informational material can include instructions to administer the compound described herein in a suitable manner to perform the methods described herein, e.g., in a suitable dose, dosage form, or mode of administration (e.g., a dose, dosage form, or mode of administration described herein). Preferred doses, dosage forms, or modes of administration are parenteral, e.g., intravenous, intramuscular, or subcutaneous. In another embodiment, the informational material can include instructions to administer the compound described herein to a suitable subject, e.g., a human, e.g., a human having or at risk for a disorder described herein. For example, the material can include instructions to administer the compound described herein to a such a subject.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about an compound described herein and/or its use in the methods described herein. Of course, the informational material can also be provided in any combination of formats.

In addition to a compound described herein, the composition of the kit can include other ingredients, such as a solvent or buffer, a stabilizer, a preservative, and/or a second compound for treating a condition or disorder described herein. Alternatively, the other ingredients can be included in the kit, but in different compositions or containers than the compound described herein. In such embodiments, the kit can include instructions for admixing the compound described herein and the other ingredients, or for using an compound described herein together with the other ingredients.

The compound described herein can be provided in any form, e.g., liquid, dried or lyophilized form. It is preferred that the compound described herein be substantially pure and/or sterile. When the compound described herein is provided in a liquid solution, the liquid solution preferably is an aqueous solution, with a sterile aqueous solution being preferred. When the compound described herein is provided as a dried form, reconstitution generally is by the addition of a suitable solvent. The solvent, e.g., sterile water or buffer, can optionally be provided in the kit.

The kit can include one or more containers for the composition containing the compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an compound described herein. For example, the kit includes a plurality of syringes, ampules, foil packets, or blister packs, each containing a single unit dose of an compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is an implantable delivery device.

EXAMPLES

Synthesis of Advanced Intermediate E

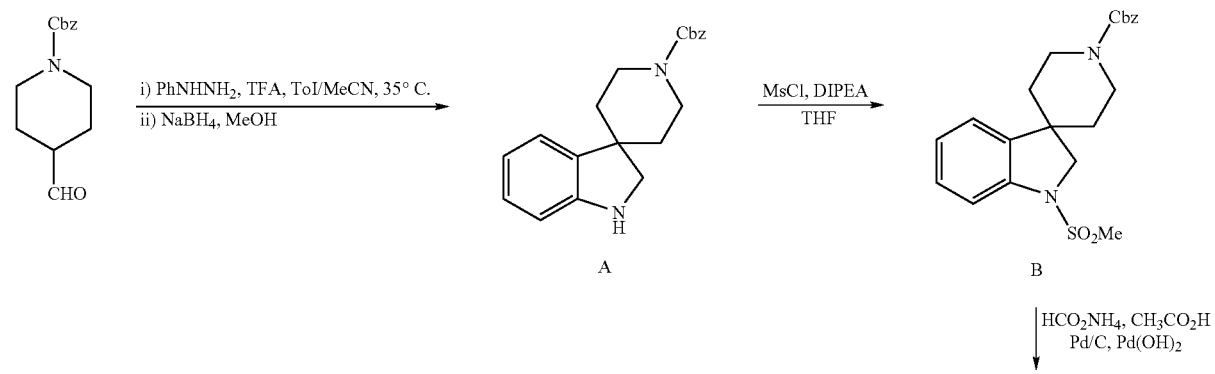

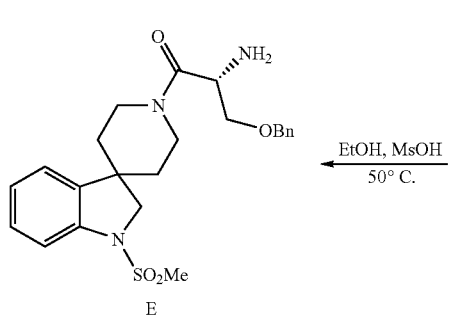
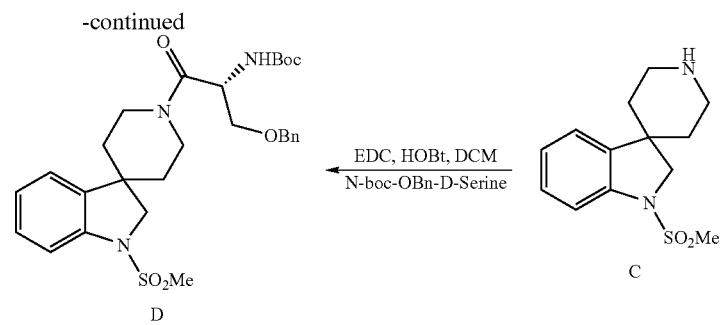

Synthesis of A:

A solution of phenylhydrazine (2.38 g, 22 mmol) and trifluoroacetic acid (5 mL) in Toluene/acetonitrile (49/1) (100 mL) was heated at 35° C. N-benzyloxycarbonyl 4-formylpiperidine (4.94 g, 20 mmol) was dissolved in 20 mL of toluene/acetonitrile (49/1) and added dropwise to the mixture, which was stirred at 35° C. overnight. The resulting solution was then cooled to 0° C., and methanol (10 mL) was added. NaBH$_4$ (1.13 g, 30 mmol) was added very slowly to the solution which was stirred for a further 45 min. The reaction mixture was washed with aqueous NH$_4$OH 6% (40 mL). Methanol (2 mL) was added and the organic layer was washed with brine (40 mL) then dried over Na$_2$SO$_4$ and evaporated. The crude material was purified by column chromatography on silica gel, eluting with ethyl acetate/cyclohexane (1/1) to give 4.85 g (75%) of A as a pale yellow solid.

Synthesis of B:

Compound A (3.03 g, 9.4 mmol) was dissolved in tetrahydrofuran (30 mL) and cooled to 0° C. diisopropylethylamine (1.8 mL, 10.3 mmol) and methanesulfonyl chloride (0.8 mL, 10.3 mmol) were added slowly. The reaction was stirred over night at room temperature. The solvent was removed under vacuum and the crude material was dissolved in dichloromethane, washed successively with aqueous HCl (1N), saturated aqueous NaHCO$_3$ and brine. The organic layer was dried over Na$_2$SO$_4$. The dichloromethane was removed by evaporation and the crude material was crystallised from hot ethanol and a drop of acetic acid to give 3.06 g (81%) of B as a beige solid.

Synthesis of C:

A mixture of B (3.06 g, 7.6 mmol), Pd(OH)$_2$/C (20% Pd, Degussa type, 300 mg), Pd/C (10% Pd, 300 mg) and ammonium formate (7.23 g, 115 mmol) in acetic acid (30 mL) was degassed and then stirred at 50° C. for 3 hours under inert atmosphere. Methanol (30 mL) was added, and the mixture was filtered. The solution was concentrated in vacuo, and aqueous NaOH (5N, 10 mL) was added. The solution was extracted with ethyl acetate (2×30 mL), dried over Na$_2$SO$_4$ and evaporated to give 1.89 g (93%) of C as a white solid.

Synthesis of D:

N-Boc-OBn-D-Serine (0.69 g, 2.34 mmol) was added to a solution of C (0.57 g, 2.13 mmol), 1-(3-dimethylaminopropyl)-3-ethylcarbodiimide hydrochloride (0.45 g, 2.34 mmol) and 1-hydroxybenzotriazole (0.32 g, 2.34 mmol) in dichloromethane (5 mL) and the resulting solution was stirred over night at room temperature. The reaction was then washed with a saturated solution of citric acid (5 mL) and then a saturated solution of NaHCO$_3$ (5 mL), dried over Na$_2$SO$_4$, filtered and evaporated in vacuo. The product was purified by silica gel chromatography eluting with ethyl acetate/cyclohexane (1/1) to give 0.77 g (67%) of D as a white solid.

Synthesis of E:

Methanesulfonic acid (1.25 mL, 19.31 mmol) was added slowly to a solution of compound D (0.70 g, 1.29 mmol) in ethanol (8 ml) which was then stirred for 1 h at 50° C. The pH adjusted to pH 9 with aqueous NaOH (2N) and the ethanol was removed in vacuo. The solution was extracted with dichloromethane, dried over Na$_2$SO$_4$ and evaporated in vacuo to give 493 mg (86%) of E.

Synthesis of 8

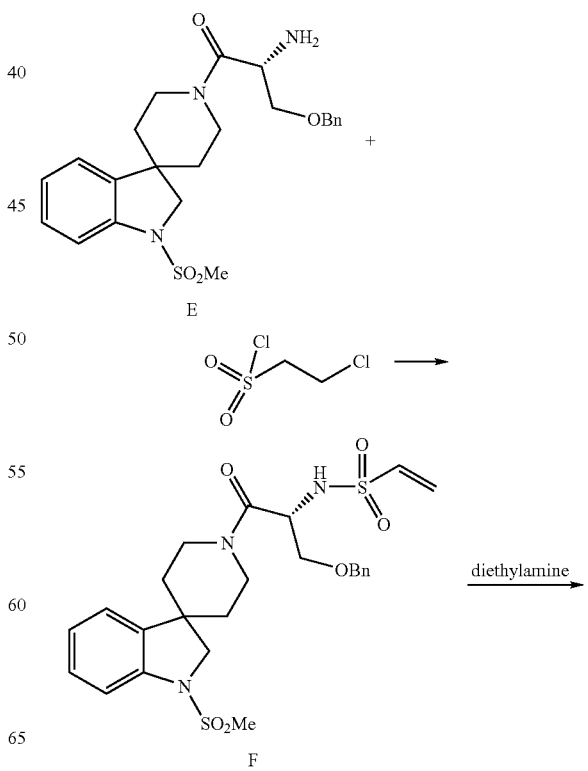

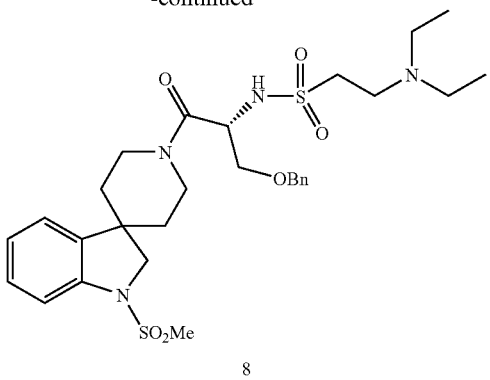

8

Sulfonamide (F) Formation:

Intermediate E (0.44 g, 1 mmol) and diisopropylethylamine (0.26 mL, 1.5 mmol) were dissolved in dichloromethane. 2-Chloroethanesulfonyl chloride (0.24 g, 1.5 mmol) was added to the solution, which was stirred at room temperature overnight. The organic layer was washed with a 10% citric acid solution then saturated aqueous $NaHCO_3$, dried over $MgSO_4$ and filtered. The solvent was removed in vacuo and the crude material purified by column chromatography eluting with ethyl acetate/heptane(3/2) to give 0.38 g (72%) of F as a colorless oil.

Formation of Compound 8:

Sulfonamide F (100 mg, 0.19 mmol) was dissolved in tetrahydrofuran (5 mL). Diethylamine (0.19 mL, 1.8 mmol) was added to the mixture, which was heated at 60° C. overnight. The solvent was then removed in vacuo and the crude material was purified by silica gel chromatography eluting with ethyl acetate to give 36 mg of a yellow oil.

Synthesis of 1-methyl piperidine-4-sulfonyl chloride

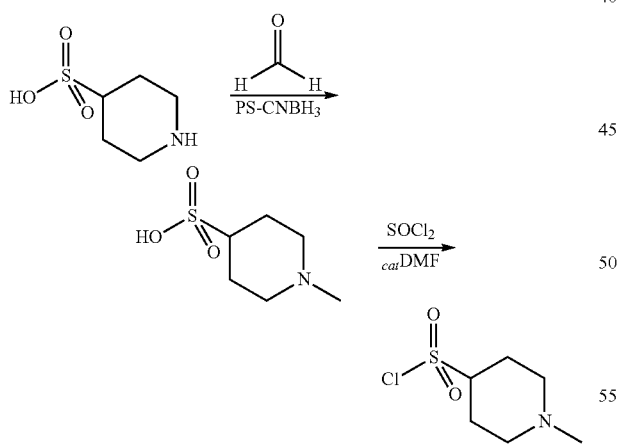

Cyanoborohydride resin (1 g, 2.50 mmol) was added followed by formaldehyde (68 µl, 0.91 mmol, 37% in aqueous solution) to a solution of the piperidine-4-sulfonic acid (200 mg, 1.21 mmol) in 10 ml of water and shaken overnight at ambient temperature. The solution was then filtered and evaporated in vacuo to give the sulfonic acid which was taken through to the next step without further purification. Yield, 177 mg (82%). $^1$H NMR (400 MHz, $D_2O$); 1.6 (m, 2H), 2.0 (m, 2H), 2.4 (s, 3H), 2.5 (m, 2H), 2.8 (m, 1H), 3.15 (m, 2H)

DMF (100 µl) was added slowly to a suspension of the crude 1-methyl piperidine-4-sulfonic acid in thionyl chloride (10 ml) and heated to reflux for 16 h. The solvent was then removed in vacuo to give the sulfonyl chloride which was taken through to the next step without further purification.

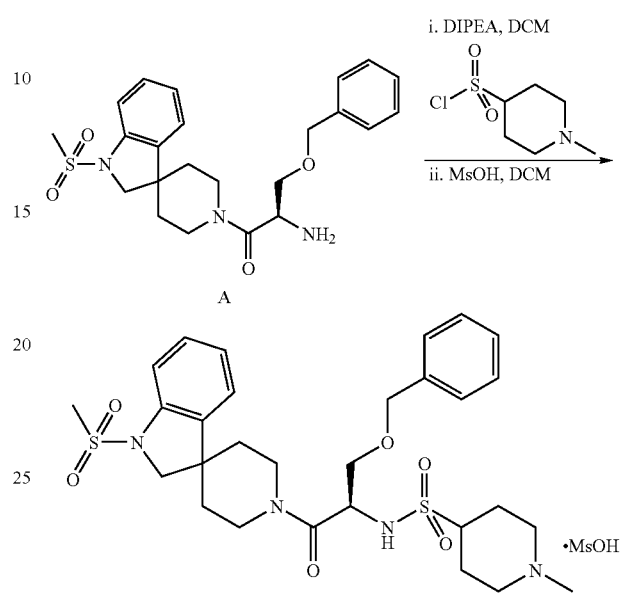

1-Methyl piperidine-4-sulfonyl chloride dissolved in DCM (5 ml) was added to a solution of A (248 mg, 0.56 mmol) and DIPEA (488 µL, 2.80 mmol) in DCM (5 ml) and stirred overnight at ambient temperature. This was washed with a saturated solution of citric acid (10 ml) followed by saturated sodium bicarbonate solution (10 ml), dried over $MgSO_4$ and evaporated in vacuo. The crude product was purified by prep LC. The product was dissolved in DCM, 1 eq MsOH was added and stirred for 30 min at ambient temperatures and then the solvent was removed in vacuo to afford 19 mg of the title compound.

$^1$H NMR (400 MHz, $CD_3OD$) 1.6 (m, 3H), 1.8 (m, 3H), 2.0-2.3 (m, 3H), 2.6 (s, 3H), 2.7-2.8 (m, 5H), 2.9 (m, 3H), 3.1 (m, 1H), 3.2-3.6 (m, 3H), 3.7 (m, 2H), 3.8 (s, 2H), 4.0 (m, 1H), 4.4-4.5 (m, 3H), 4.7 (m, 1H), 6.7 (m, 0.5H), 6.9 (m, 0.5H), 6.95 (m, 0.5H), 7.15 (m, 1.5H), 7.2-7.35 (m, 6H).

General method for 1-(3-dimethylaminopropyl)-3-ethylcarbodiimide hydrochloride, 1-hydroxybenzotriazole coupling

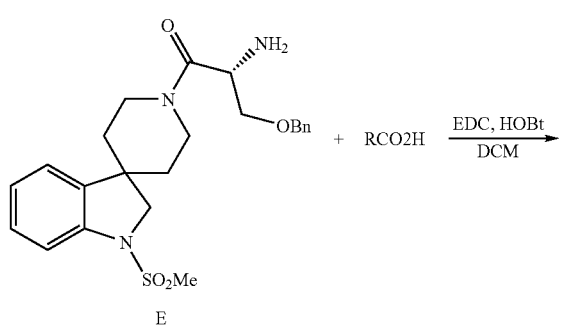

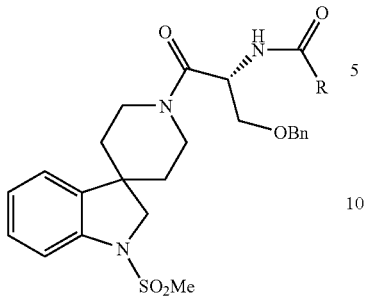

The acid (1.2 eq.), 1-(3-dimethylaminopropyl)-3-ethylcarbodiimide hydrochloride (1.2 eq.) and 1-hydroxybenzotriazole (1.2 eq.) were dissolved in 20 volumes of dichloromethane and the solution stirred for 5 min at room temperature. A solution of the amine E (1 eq.) in 10 volumes dichloromethane was added to the mixture, which was stirred at room temperature overnight. The solution was washed with saturated aqueous $NaHCO_3$, dried over $Na_2SO_4$ and filtered. The dichloromethane was removed in vacuo to give the products which were purified with appropriate eluants as shown below.

Formation of Compound 1

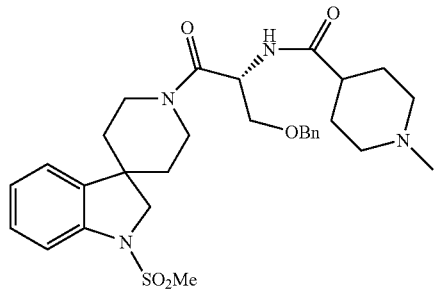

N-Methylpiperidine-4-carboxylic acid hydrochloride was used in the coupling following the general procedure. 195 mg (0.44 mmol) of the amine E was used. The crude material was then purified by column chromatography on silica gel eluting with dichloromethane/MeOH (8/2) to give 160 mg (65%) of compound 1.

Formation of Compound 128

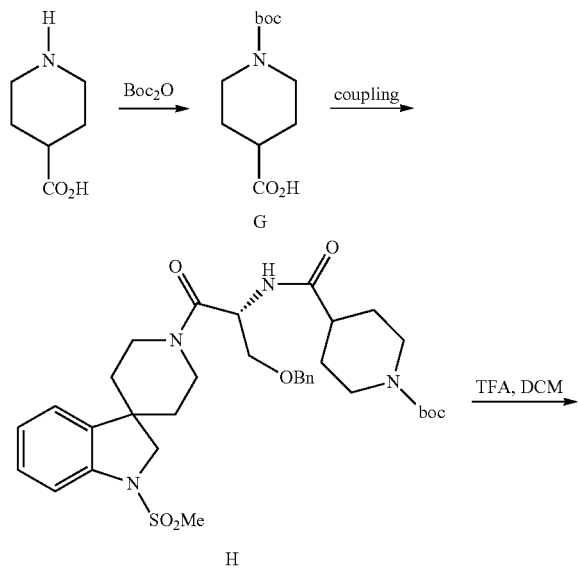

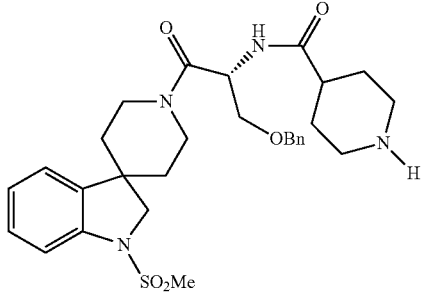

Isonipecotic acid (3 g, 23.2 mmol) was dissolved in dioxane/NaOH (1M) (1/1) (70 mL). Boc-anhydride (5.57 g, 25.5 mmol) was added to the solution at 0° C., which was then allowed to warm up to room temperature and stirred for 1 h. The solution was concentrated in vacuo and ethyl acetate (10 mL) was added. The mixture was acidified to pH 2 using saturated aqueous $KHSO_4$. The organic layer was dried over $Na_2SO_4$ and evaporated to give 4.7 g (89%) of N-Boc isonipecotic acid G as a colorless solid. G was used in the coupling step with the amine E (100 mg, 0.22 mmol) following the general method. The intermediate H was purified by column chromatography eluting with ethyl acetate/cyclohexane (1/1). H was treated with dichloromethane/trifluoroacetic acid (8/2) (2 mL) for 2 h at room temperature. Saturated aqueous $NaHCO_3$ was then added carefully until pH 9 was reached and the dichloromethane layer was separated, dried over $Na_2SO_4$, filtered and the solvent removed in vacuo to give the free amine 99 mg (81% over two steps).

Formation of Compound 7

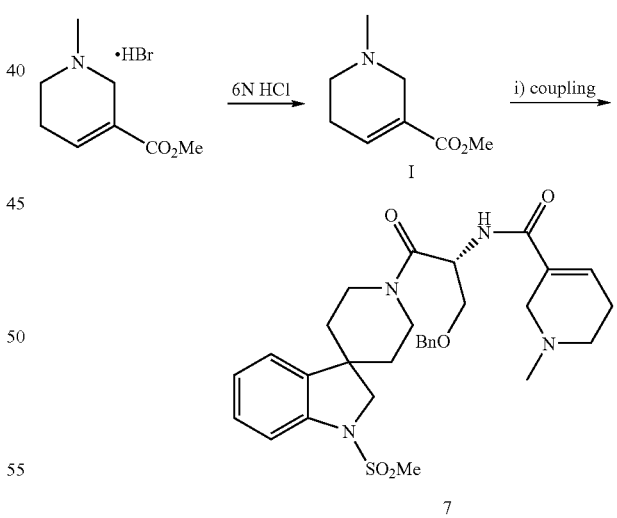

6N HCl (6 mL) was added to arecoline hydrobromide (300 mg, 1.27 mmol) and the resulting solution was heated to reflux overnight. The solvent was then removed in vacuo to afford the compound I which was used in the coupling step without further purification following the general coupling procedure using 100 mg (0.22 mmol) of the amine E. Compound 7 was purified by column chromatography eluting with 2.5% methanol in dichloromethane to give 40 mg (32%) of a colorless solid.

Formation of Compound 2

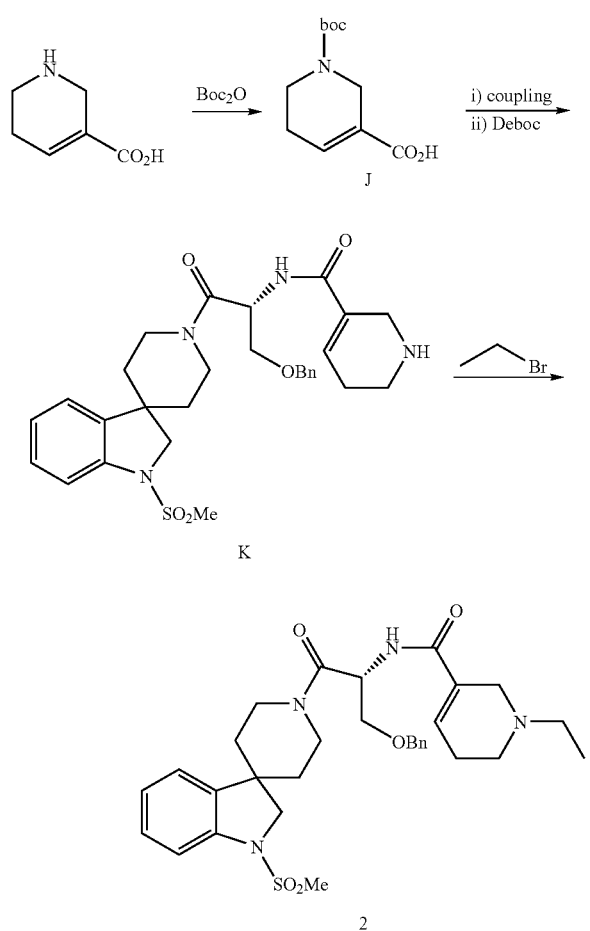

| Procedure used for High pH method for prep LC: | | | |
|---|---|---|---|
| Column: Xterra-prep MS C18 column | | | |
| 5 uM particle size | | | |
| 19 × 50 mm | | | |
| Mobile phase: | | | |
| Aqueous - 10 mM Ammonium bicarbonate pH 10 | | | |
| Organic - Acetonitrile | | | |
| Gradient: | 0.4 mins | 95% aq | 5% org |
| | 4 mins | 5% aq | 95% org |
| | 4.5 mins | 5% aq | 95% org |
| | 5 mins | 0% aq | 100% org |
| | 6 mins | 0% aq | 100% org |
| | 7 mins | 95% aq | 5% org |

Formation of Compound 6

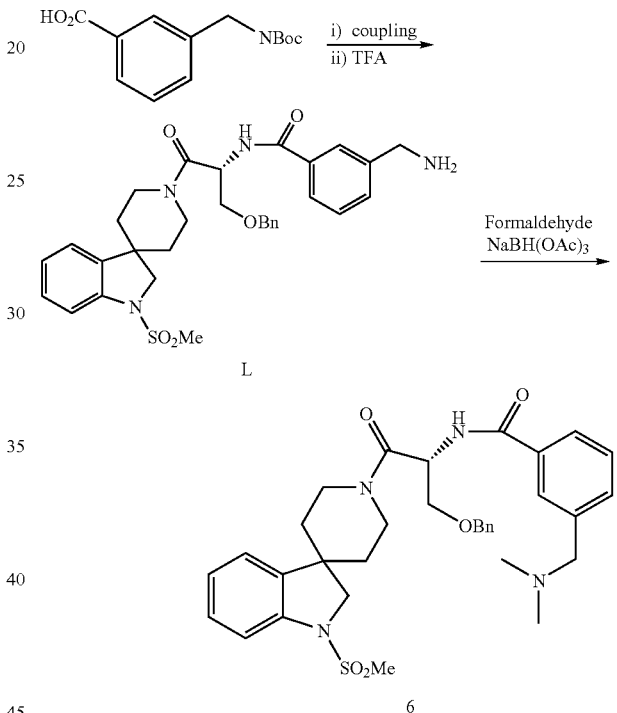

Guvacine (190 mg, 1.5 mmol) was dissolved in dioxane/NaOH (1M) (1/1) (6 mL). Boc-anhydride (370 mg, 1.7 mmol) was then added to the solution at 0° C., which was then allowed to reach room temperature and stir overnight. The solution was concentrated in vacuo and ethyl acetate (2 mL) was added. The mixture was washed with saturated aqueous $KHSO_4$. The organic layer was separated, dried over $Na_2SO_4$, filtered and the solvent removed in vacuo to give a colorless solid. J was used in the next step using the general method for coupling with 270 mg (0.60 mmol) of amine E. The Boc protected intermediate was purified by column chromatography eluting with ethyl acetate/cyclohexane (1/1) (300 mg, 76%). This intermediate was treated with dichloromethane/trifluoroacetic acid (8/2) (2 mL) for 2 h at room temperature. Saturated aqueous $NaHCO_3$ was then added until basic pH and the dichloromethane layer was separated, dried over $Na_2SO_4$ and evaporated to give the free amine K (230 mg, 89%). This amine K (110 mg, 0.2 mmol) was then dissolved in DMF (1 mL). $K_2CO_3$ (30 mg, 0.22 mmol) and bromoethane (16 μL, 0.22 mmol) were added to the mixture. The mixture was reacted in a focussed microwave at 90° C., 200 Watts, 150 Psi (max) for 15 min. The DMF was evaporated under reduced pressure and the crude material was purified by prep LC (high pH method) to give 12 mg (10%) of a colorless oil.

3-(Boc-aminomethyl)benzoic acid (93 mg, 0.37 mmol) was coupled with amine E (150 mg, 0.34 mmol) following the general coupling method. The product was purified by silica gel chromatography eluting with ethyl acetate/Heptanes (6/4) to give 181 mg of a white solid. This was then treated with a mixture of dichloromethane/trifluoroacetic acid (8/2) (3 mL) for 2 hr at room temperature. Saturated aqueous $NaHCO_3$ was then added until pH 9 and the dichloromethane layer was separated, dried over $Na_2SO_4$ and evaporated to give the free amine L (139 mg).

L (128 mg, 0.22 mmol) was dissolved in tetrahydrofuran/trimethylothoformate (1/1) (2 mL). $NaBH(OAc)_3$ (235 mg, 1.11 mmol) and formaldehyde (37% in water, 80 μL, 1.11 mmol) were added to the mixture, which was stirred at room temperature overnight. The solvent was removed in vacuo. The crude material was dissolved in dichloromethane, washed with saturated aqueous $NaHCO_3$ and brine. The organic layer was dried over $Na_2SO_4$ and evaporated. The product was purified by silica gel chromatography eluting with a mixture dichloromethane/MeOH/$NH_{3(aq)}$ (94/5/1) to give 23 mg (12%) of a white solid.

Formation of Compound 11

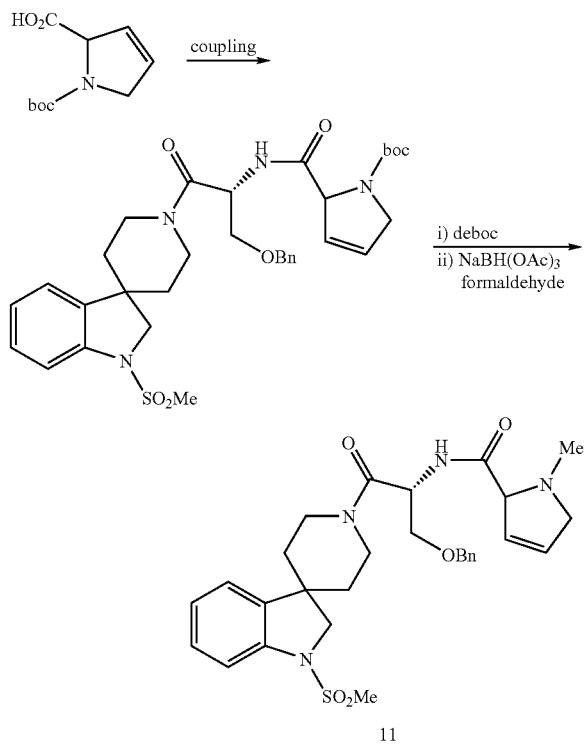

100 mg (63%) of a white solid, was prepared according to the procedure described for compound 11.

Refeeding Assays

Animals: For this particular experiment, male C57BL/6J mice (Vendor: Taconic; Age: 7 weeks; Weight Range: 19-25 g) were used. The animals were housed individually during acclimation to facility (3-5 days) and throughout the study. The housing included a fixed light cycle: Lights on at 6 am, Lights off at 6 pm. Thirty mice were used in this particular study.

Study Groups were as follows (i.p.=intraperitoneal injection; s.c.=subcutaneous injection)
  Control: saline+acetic acid (pH=5), i.p. (n=6)
  2 mpk Compound 1, i.p. (n=6) (vehicle, saline+acetic acid (pH=5)
  20 mpk Compound 1, i.p. (n=6) (vehicle, saline+acetic acid (pH=5)
  2 mpk Compound 1, s.c. (n=6) (vehicle, saline+acetic acid (pH=5)
  20 mpk Compound 1, s.c. (n=6) (vehicle, saline+acetic acid (pH=5)

All solutions were prepared (in saline+acetic acid) and coded by a first person and administered by a second person. So that the second person was unaware of the compound being assayed at the time of the assay. Tubes were labeled 1-6 and decoded following termination of the study.

Procedure:

1. Day 0:
  Mice were weighed and sorted into groups based on Body Weight.
  Food was removed at 6 pm for an overnight (~16 hour) fast.

2. Day 1:
  Beginning at 10 am, mice were injected 30 seconds-1 minute apart (i.p. or s.c.) with either vehicle (saline+ acetic acid, pH=5) or Compound 1. See above for details. After injections mice were returned to their home cages.
  Following each injection, pre-weighed food was immediately returned to the food hoppers.
    Note: food was weighed the morning injections were administered.
    Mouse weighed
    Food weighed (approx. 90 g)
    Mouse injected
    Pre-weighed food returned to hopper
  Food Weights were measured at 30 min, 1 hr, 2 hr, and 4 hrs post injection.
  Final body weights were recorded and mice were euthanized via $CO_2$ asphyxiation.

Results:

Compound 1 was administered intraperitoneally. Substantially decreased food intake was observed for the duration of the 4 hour test. Subcutaneous administration of Compound 1 is equally effective up to 1 hour, but shows little or no effect after 2 hours.

Using certain in vivo conditions and one formulation, the compound Compound 1 was found to have poor oral bioavailability. However, Compound 1 has potent results in the fast-refeed assay, when administered by injection.

The same procedure was used again in another experiment in which compounds 1, 2, and 6 were evaluated. Results are as follows:

Experimental Groups: 6 mice/group x 5 groups (total mice=30)
  1 Control: saline(ip)
  2 Compound 1: 20 mg/kg(ip) 5 mg/ml (vehicle, saline+ acetic acid (pH=5)
  3 Compound 2: 20 mg/kg(ip) 5 mg/ml (vehicle, saline+ acetic acid (pH=5)
  4 Compound 6: 20 mg/kg(ip) 5 mg/ml ((vehicle, saline+ acetic acid (pH=5)

The same procedure was used again to evaluate compounds 7 and 8 and Substance P.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

What is claimed is:

1. A compound of formula (I) or a pharmaceutically acceptable salt thereof:

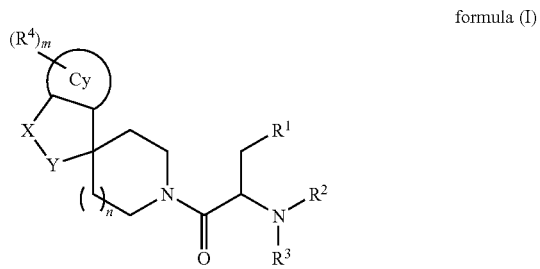

formula (I)

wherein, $R^1$ is H, $C_1$-$C_{10}$ alkyl, aryl, aryl($C_1$-$C_6$ alkyl), heteroaryl, heteroaryl($C_1$-$C_6$ alkyl), cycloalkyl, cycloalkyl($C_1$-$C_6$ alkyl), heterocyclyl, heterocyclyl($C_1$-$C_6$ alkyl), ($C_1$-$C_6$ alkyl)-K-($C_0$-$C_6$ alkyl), aryl($C_0$-$C_6$ alkyl)-K-($C_0$-$C_6$ alkyl), heteroaryl($C_0$-$C_6$ alkyl)-K-($C_0$-$C_6$ alkyl), cycloalkyl($C_0$-$C_6$ alkyl)-K-($C_0$-$C_6$ alkyl), or heterocyclyl($C_0$-$C_6$ alkyl)-K-($C_0$-$C_6$ alkyl); wherein $R^1$ can be taken together with one or both of $R^2$ and $R^3$ and the carbon to which it is attached to form a heterocyclyl or heteroaryl ring structure; wherein K is O, S, SO, $SO_2$, $N(R^5)C(O)$, $C(O)N(R^5)$, OC(O), C(O)O, $CR^5$=$CR^5$, or C≡C; wherein each alkyl can be independently substituted with at least one halo, $C_1$-$C_6$ alkyl, acetyl, $SO_2R^6$, $OR^6$, $CO_2R^6$; and wherein each aryl, heteroaryl, cycloalkyl or heterocyclyl can be independently substituted with aryl, aryloxy, $C_1$-$C_6$ alkyl, halo, $OR^6$, $SO_2R^6$, $CF_3$, $OCF_3$, $NO_2$, $N(R^5)_2$, $N(R^5)C(O)(R^5)$, $C(O)OR^6$, $OC(O)R^5$, $C(O)N(R^5)_2$, $SO_2N(R^5)_2$, or $N(R^5)SO_2(R^5)$;

$R^2$ is $SO_2R^8$; and wherein $R^2$ can be taken together with one or both of $R^1$ and $R^3$ and the nitrogen to which it is attached to form a heterocyclyl or heteroaryl ring structure;

$R^3$ is H, $C_1$-$C_6$ alkyl, acetyl, or aryl ($C_1$-$C_6$ alkyl), wherein aryl can be optionally substituted with $R^6$ or $OR^6$; and wherein $R^3$ can be taken together with one or both of $R^1$ and $R^2$ and the nitrogen to which it is attached to form a heterocyclyl or heteroaryl ring structure;

each $R^4$ is independently halo, $C_1$-$C_6$ alkyl, alkoxy, CN, $N(R^6)_2$, acetyl, $CF_3$ or $OCF_3$, $OCH_2CF_3$;

each $R^5$ is independently H, $C_1$-$C_6$ alkyl, acetyl, cycloalkyl, aryl, aryl ($C_1$-$C_6$ alkyl), heteroaryl, or heteroaryl ($C_1$-$C_6$ alkyl); each of which is substituted with one or more $R^4$;

each $R^6$ is independently H or $C_1$-$C_6$ alkyl;

each $R^8$ is independently cycloalkyl, cycloalkyl ($C_1$-$C_6$ alkyl), heterocyclyl, heterocyclyl ($C_1$-$C_6$ alkyl), aryl, aryl ($C_1$-$C_6$ alkyl), heteroaryl, heteroaryl ($C_1$-$C_6$ alkyl), $C_1$-$C_6$ alkyl, $C_2$-$C_6$ alkenyl, $C_2$-$C_6$ alkynyl; each of which is independently substituted with $R^9$, halo, $C_1$-$C_6$ alkyl, $OR^5$, CN, $NO_2$, $N(R^5)_2$, $C(O)R^5$, $C(O)OR^5$, $OC(O)R^5$, $N(R^5)C(O)R^5$, $N(R^5)C(O)OR^5$, $C(O)N(R^5)_2$, $SR^5$, $SO_2R^5$, $S(O)R^5$, or $SO_2N(R^5)_2$;

X is $CHC(O)OR^9$, $CHC(O)R^9$, $CHC(O)N(R^9)_2$, $CHN(R^9)_2$, CO, $CHN(R^9)SO_2R^9$, $CHCH_2OR^9$, $CHR^9$, or when taken together with Y is $CR^9$=$CR^9$;

Y is $(CH_2)_p$, $CHC_1$-$C_8$ alkyl, CO, or when taken together with X is $CR^9$=$CR^9$;

each $R^9$ is independently H, $C_1$-$C_6$ alkyl, aryl ($C_1$-$C_6$)alkyl, cycloalkyl ($C_0$-$C_6$)alkyl, heterocyclyl ($C_0$-$C_6$)alkyl, aryl ($C_0$-$C_6$)alkyl, or heteroaryl ($C_0$-$C_6$)alkyl; each of which can be independently substituted with one or more $R^{10}$;

each $R^{10}$ is independently H, $C_1$-$C_6$ alkyl, aryl ($C_1$-$C_6$) alkyl, cycloalkyl ($C_0$-$C_6$)alkyl, heterocyclyl ($C_0$-$C_6$) alkyl, aryl ($C_0$-$C_6$)alkyl, or heteroaryl ($C_0$-$C_6$)alkyl, halo, $OR^5$, $NR^4SO_2R^5$, $N(R^5)_2$, CN, $C(O)OR^5$, $OC(O)R^5$, $COR^5$, $NO_2$, $SO_2N(R^5)_2$, $SO_2R^5$, $S(O)R^5$, $SR^5$, $CF_3$, $CH_2CF_3$ or $OCF_3$;

Cy is aryl;

m is 0-6;

n is 1; and p is 1;

wherein $R^8$ is not di-chlorophenyl when $R^1$ is benzyloxy.

2. The compound of claim 1, wherein $R^1$ is aryl, aryl($C_1$-$C_6$ alkyl), heteroaryl($C_1$-$C_6$ alkyl), heteroaryl, aryl($C_0$-$C_6$ alkyl)-K-($C_1$-$C_6$ alkyl), or heteroaryl($C_0$-$C_6$ alkyl)-K-($C_0$-$C_6$ alkyl); wherein K is O, N, or S; wherein each alkyl can be independently substituted with at least one halo, $C_1$-$C_6$ alkyl, acetyl, $SO_2R^6$, $OR^6$, $CO_2R^6$; and wherein each aryl, heteroaryl, cycloalkyl or heterocyclyl can be independently substituted with aryl, aryloxy, $C_1$-$C_6$ alkyl, halo, $OR^6$, $SO_2R^6$, $CF_3$, $OCF_3$, $NO_2$, $N(R^5)_2$, $N(R^5)C(O)(R^5)$, $C(O)OR^6$, $OC(O)R^5$, $C(O)N(R^5)_2$, $SO_2N(R^5)_2$, or $N(R^5)SO_2(R^5)$.

3. The compound of claim 2, wherein $R^1$ is aryl($C_0$-$C_6$ alkyl)-K-($C_1$-$C_6$ alkyl).

4. The compound of claim 3, wherein $R^1$ is benzyloxy.

5. The compound of claim 2, wherein $R^1$ is aryl($C_1$-$C_6$ alkyl).

6. The compound of claim 5, wherein $R^1$ is benzyl.

7. The compound of claim 1, wherein $R^8$ is $C_1$-$C_6$ alkyl substituted with $R^9$ or $N(R^5)_2$.

8. The compound of claim 7, wherein $R^9$ is heterocyclyl.

9. The compound of claim 8, wherein $R^9$ is a nitrogen containing heterocyclyl.

10. The compound of claim 9, wherein the nitrogen containing heterocyclyl is substituted with $C_1$-$C_4$ alkyl.

11. The compound of claim 8, wherein $R^9$ is pyrrolidyl, piperidyl, piperizinyl, or morpholinyl.

12. The compound of claim 7, wherein $R^8$ is substituted with $N(R^5)_2$, and each $R^5$ is independently H or $C_1$-$C_6$ alkyl.

13. The compound of claim 12, wherein each $R^5$ is independently H, methyl, ethyl, isopropyl, or t-butyl.

14. The compound of claim 13, wherein $N(R^5)_2$ is selected from the group consisting of

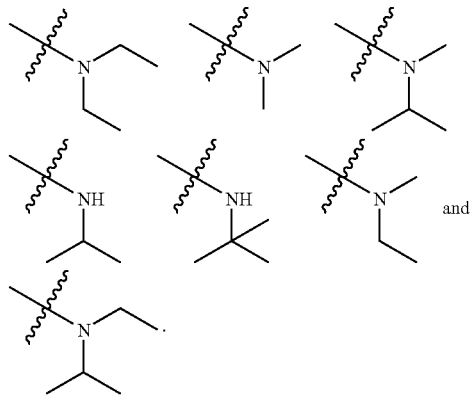

15. The compound of claim 9, wherein the nitrogen containing heterocyclyl is a bridged heterocyclyl.

16. The compound of claim 1, wherein $R_8$ is $C_2$ or $C_3$ alkyl substituted with $R^9$ or $N(R^5)_2$.

17. The compound of claim 16, wherein $N(R^5)_2$ is selected from the group consisting of

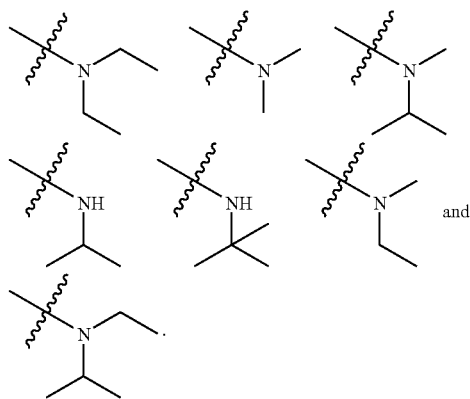

18. The compound of claim 1, wherein X and Y taken together are $CR^9$=$CR^9$.

19. The compound of claim 1, where Cy is phenyl.

20. The compound of claim 1, wherein Y is $CH_2$.

21. The compound of claim 1, wherein Y is $CH_2$, Cy is phenyl, m is 0, and n is 1.

22. The compound of claim 1, wherein X and Y taken together are $CR^9$=$CR^9$, Cy is phenyl, m is 0, and n is 1.

23. The compound of claim 1, wherein $R^3$ is H or methyl.

24. The compound of claim 1, wherein;
$R^1$ is aryl($C_0$-$C_6$ alkyl)-K-($C_1$-$C_6$ alkyl), aryl($C_1$-$C_6$ alkyl), or heteroaryl;
$R^2$ is $R^8$ is $C_1$-$C_6$ alkyl substituted with $R^9$ or $N(R^5)_2$;
$R^3$ is H or Me;
X taken together with Y is $CR^9$=$CR^9$;
Y taken together with x is $CR^9$=$CR^9$;
Cy is phenyl; and
n is 1.

25. The compound of claim 24, wherein $R_8$ is $C_2$ or $C_3$ alkyl substituted with $R^9$ or $N(R^5)_2$.

26. The compound of claim 25, wherein $R^8$ is substituted with a nitrogen containing heterocyclyl, or a substituent selected from the group consisting of

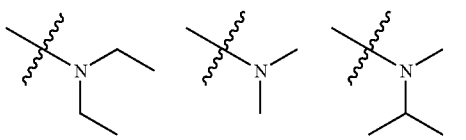

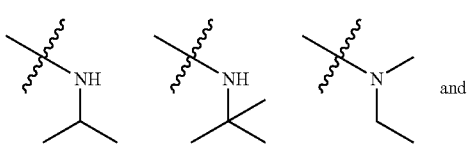

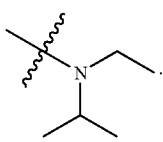

27. The compound of claim 24, wherein $R^1$ is benzyloxy or benzyl.

28. The compound of claim 24, wherein m is 0.

29. The compound of claim 1, wherein
$R^1$ is benzyloxy;
$R^8$ is $C_1$-$C_6$ alkyl substituted with $R^9$ or $N(R^5)_2$;
$R^3$ is H or Me;
X taken together with Y is $CR^9$=$CR^9$;
Y taken together with x is $CR^9$=$CR^9$;
Cy is phenyl; and
n is 1.

30. The compound of claim 1, wherein;
$R^1$ is aryl($C_0$-$C_6$ alkyl)-K-($C_1$-$C_6$ alkyl), aryl($C_1$-$C_6$ alkyl), or heteroaryl;
$R^8$ is $C_2$-$C_3$ alkyl substituted with heterocyclyl or $N(R^5)_2$;
$R^3$ is H or Me;
X taken together with Y is $CR^9$=$CR^9$;
Y taken together with x is $CR^9$=$CR^9$;
Cy is phenyl; and
n is 1.

31. The compound of claim 30, wherein $R^8$ is substituted with $N(R^5)_2$ or a nitrogen containing heterocyclyl.

32. The compound of claim 31, wherein $N(R^5)_2$ is selected from the group consisting of

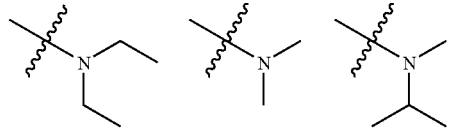

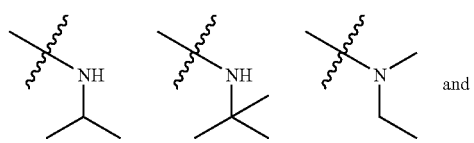

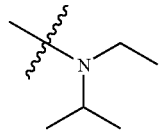

33. The compound of claim 1, wherein;
$R^1$ is aryl($C_0$-$C_6$ alkyl)-K-($C_1$-$C_6$ alkyl), aryl($C_1$-$C_6$ alkyl), or heteroaryl;
$R^8$ is $C_1$-$C_6$ alkyl substituted with $R^9$ or $N(R^5)_2$;
$R^3$ is H or Me;
X and Y taken together are $CR^9$=$CR^9$;
Cy is phenyl;
$R^9$ is H; and
n is 1.

34. The compound of claim 1, wherein;
$R^1$ is aryl($C_0$-$C_6$ alkyl)-K-($C_1$-$C_6$ alkyl), aryl($C_1$-$C_6$ alkyl), or heteroaryl;
$R^8$ is $C_2$-$C_3$ alkyl substituted with heterocyclyl or $N(R^5)_2$;
$R^3$ is H or Me;
X taken together with Y is $CR^9$=$CR^9$;
Y taken together with x is $CR^9$=$CR^9$;
Cy is phenyl;
m is 0; and
n is 1.

35. A compound selected from the group consisting of:

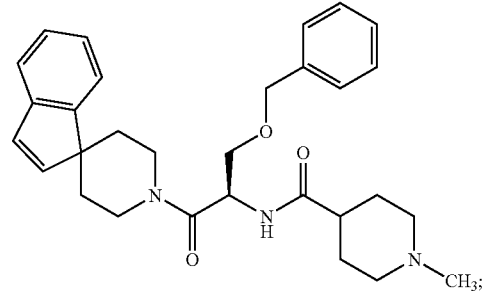

145
-continued
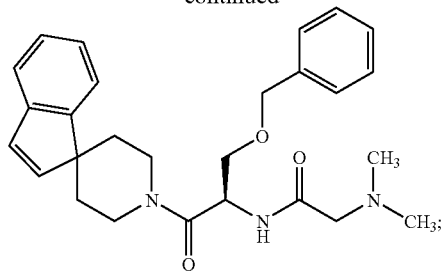
146
-continued
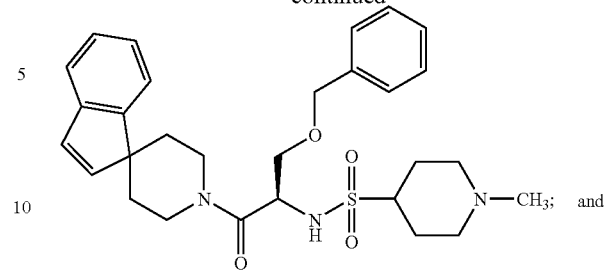
* * * * *